(12) United States Patent
Yonemitsu et al.

(10) Patent No.: US 7,510,706 B2
(45) Date of Patent: Mar. 31, 2009

(54) PSEUDOTYPE RETROVIRAL VECTORS CONTAINING MEMBRANE PROTEINS HAVING HEMAGGLUTININ ACTIVITY

(75) Inventors: Yoshikazu Yonemitsu, Fukuoka (JP); Toshihiro Nakajima, Hyogo (JP); Kenji Nakamaru, Tokyo (JP); Masanori Kobayashi, Osaka (JP); Mamoru Hasegawa, Ibaraki (JP); Yasuji Ueda, Ibaraki (JP); Akihiro Iida, Ibaraki (JP); Hiroyuki Sakakibara, Ibaraki (JP)

(73) Assignee: DNAVEC Research Inc., Ibaraki (JP)

( * ) Notice: Subject to any disclaimer, the term of this patent is extended or adjusted under 35 U.S.C. 154(b) by 295 days.

(21) Appl. No.: 10/306,949

(22) Filed: Nov. 29, 2002

(65) Prior Publication Data

US 2003/0203489 A1 Oct. 30, 2003

Related U.S. Application Data

(63) Continuation-in-part of application No. PCT/JP01/04659, filed on Jun. 1, 2001.

(30) Foreign Application Priority Data

Jun. 1, 2000 (JP) ............................. 2000-169090

(51) Int. Cl.
*A01N 63/00* (2006.01)
*A61K 48/00* (2006.01)
*C12N 5/00* (2006.01)
*C12N 15/00* (2006.01)
*A61K 31/70* (2006.01)

(52) U.S. Cl. .................... 424/93.2; 435/320.1; 435/325; 435/455; 424/93.1; 514/44

(58) Field of Classification Search ................ 435/69.1, 435/320.1, 325, 455; 424/93.1; 514/44
See application file for complete search history.

(56) References Cited

U.S. PATENT DOCUMENTS

| | | |
|---|---|---|
| 6,645,760 B2 | 11/2003 | Nagai et al. |
| 6,723,532 B2 | 4/2004 | Nagai et al. |
| 6,743,620 B1 | 6/2004 | Iba et al. |
| 6,746,860 B1 | 6/2004 | Tokusumi et al. |
| 6,828,138 B1 | 12/2004 | Nagai et al. |
| 7,314,614 B1 | 1/2008 | Yonemitsu et al. |
| 2002/0002143 A1 | 1/2002 | Kano et al. |
| 2002/0098576 A1 | 7/2002 | Nagai et al. |
| 2003/0166252 A1 | 9/2003 | Kitazato et al. |
| 2003/0170210 A1 | 9/2003 | Masaki et al. |
| 2003/0170266 A1 | 9/2003 | Kitazato et al. |
| 2003/0170897 A1 | 9/2003 | Imai et al. |
| 2004/0005296 A1 | 1/2004 | Yonemitsu et al. |
| 2004/0053877 A1 | 3/2004 | Fukumura et al. |
| 2004/0101965 A1 | 5/2004 | Griesenbach et al. |
| 2004/0121308 A1 | 6/2004 | Nagai et al. |

FOREIGN PATENT DOCUMENTS

| | | |
|---|---|---|
| WO | WO 98/27217 A1 | 6/1998 |
| WO | WO 99/13905 A1 | 3/1999 |
| WO | WO 02/38726 A2 | 5/2002 |
| WO | WO 02/38726 A3 | 5/2002 |
| WO | WO 03/066868 A1 | 8/2003 |
| WO | WO 2004/022731 A1 | 3/2004 |

OTHER PUBLICATIONS

Spiegel et al, J Virol. 72(6):5296-5302, 1998.*
Peterson et al, PNAS 82:75207524, 1985.*
Goncalves, Bioessays. 27(5):506-517, 2005.*
Juengst, BMJ, 326:1410-11, 2003.*
Check Nature 422:7, 2003.*
Couzin et al, Science 307:1028, 2005.*
Rosenberg et al, Science 287:1751, 2000.*
Anderson, Nature 392:25-30, 1998.*
Touchette, Nat. Med. 2(1) 7-8, 1996.*
Jung et al, Biotechnol Bioeng. 99(4):1016-27, 2008.*
Kobayashi et al, J Virol. 77(4):2607-2614, 2003.*
Agrawal et al., "Cell-Cycle Kinetics and VSV-G Pseudotyped Retrovirus-Mediated Gene Transfer in Blood-Derived CD34+ Cells," *Exp. Hematol.* 24:738-747 (1996).
Dong et al., "A Chimeric Avian Retrovirus Containing the Influenza Virus Hemagglutinin Gene Has an Expanded Host Range," *J. Virol.* 66:7374-7382 (1992).
Hatziioannou et al., "Incorporation of Fowl Plague Virus Hemagglutinin into Murine Leukemia Virus Particles and Analysis of the Infectivity of the Pseudotyped Retroviruses," *J. Virol.* 72:5313-5317 (1998).
Morrison et al., "Complementation between Avirulent Newcastle Disease Virus and a Fusion Protein Gene Expressed from a Retrovirus Vector: Requirements for Membrane Fusion," *J. Virol.* 65:813-822 (1991).
Schnell et al., "Development of a Self-Inactivating, Minimal Lentivirus Vector Based on Simian Immunodeficiency Virus," *Human Gene Therapy* 11:439-447 (2000).
Spiegel et al., "Asialoglycoprotein (ASGP-R)-Restricted Gene Transfer by Retroviral Particles Pseudotyped with Sendai Virus F Protein," *Hepatology* (Abstract 1429) 28:520A (1998).

(Continued)

*Primary Examiner*—Sumesh Kaushal
(74) *Attorney, Agent, or Firm*—Clark & Elbing LLP

(57) ABSTRACT

The present invention provides a retroviral vector containing a membrane protein having a hemagglutinin activity. The present inventors constructed a retroviral vector pseudotyped by the membrane protein having a hemagglutinin activity. This viral vector showed gene transfer at a high efficiency into host cells. In particular, it was established that genes can be transferred thereby at a high efficiency into cells into which genes can hardly be transferred by the conventional techniques, for example, blood cells and hematopoietic cells including hematopoietic stem cells, and mucous cells including mucosa epithelial cells. The viral vector of the present invention is highly useful as a vector for gene therapy.

54 Claims, 26 Drawing Sheets

OTHER PUBLICATIONS

Spiegel et al., "Pseudotype Formation of Moloney Murine Leukemia Virus with Sendai Virus Glycoprotein F," *J. Virol.* 72:5296-5302 (1998).

Bosch et al., "Inhibition of Release of Lentivirus Particles With Incorporated Human Influenza Virus Haemagglutinin By Binding To Sialic Acid-Containing Cellular Receptors," *J. Gen. Virol.* 82(Pt. 10):2485-2494 (2001).

Compans et al., "Effect of Antibody to Neuraminidase on the Maturation and Hemagglutinating Activity of an Influenza $A_2$ Virus," *J. Virol.* 4(4):528-534 (1969).

Griffin et al., "Effects of Hexose Starvation and the Role of Sialic Acid in Influenza Virus Release," *Virology* 125(2):324-334 (1983).

Lin and Cannon, "Use of Pseudotyped Retroviral Vectors To Analyze the Receptor-Binding Pocket of Hemagglutinin From a Pathogenic Avian Influenza A Virus (H7 Subtype)," *Virus Res.* 83(1-2):43-56 (2002).

Liu et al., "Influenza Type A Virus Neuraminidase Does Not Play A Role in Viral Entry, Replication, Assembly, Or Budding," *J. Virol.* 69(2):1099-1106 (1995).

Morse et al., "Optimizing Influenza Hemagglutinin Pseudotyping of Equine Lentiviral Vectors," *Mol. Ther.* 5(5 Pt. 2):S38(Abstract110) (2002).

Négre et al., "Characterization of Novel Safe Lentiviral Vectors Derived From Simian Immunodeficiency Virus (SIVmac251) That Efficiently Transduce Mature Human Dendritic Cells," *Gene Ther.* 7(19):1613-1623 (2000).

Palese et al., "Characterization of Temperature Sensitive Influenza Virus Mutants Defective in Neuraminidase," *Virology* 61(2):397-410 (1974).

Sakurada et al., "Cloning, Expression, and Characterization of the *Micromonospore viridifaciens* Neuraminidase Gene in *Streptomyces lividans*," *J. Bacteriol.* 174(21):6896-6903 (1992).

Sun et al., "Neuraminidase From A Bacterial Source Enhances Both HIV-1-Mediated Syncytium Formation and the Virus Binding/Entry Process," *Virology* 284(1):26-36 (2001).

Yang et al., "Hemagglutinin Specificity and Neuraminidase Coding Capacity of Neuraminidase-Deficient Influenza Viruses," *Virology* 229(1):155-165 (1997).

Vzorov and Compans, "Effect of the Cytoplasmic Domain of the Simian Immunodeficiency Virus Envelope Protein on Incorporation of Heterologous Envelope Proteins and Sensitivity to Neutralization," *J. Virol.* 74(18):8219-8225 (2000).

Burns et al., "Vesicular Stomatitis Virus G Glycoprotein Pseudotyped Retroviral Vectors: Concentration to Very High Titer and Efficient Gene Transfer into Mammalian and Nonmammalian Cells," *Proc. Natl. Acad. Sci. USA* 90(17):8033-8037 (1993).

Kobayashi et al., "Pseudotyped Lentivirus Vectors Derived from Simian Immunodeficiency Virus SIVagm with Envelope Glycoproteins from Paramyxovirus," *J. Virol.* 77(4):2607-2614 (2003).

Parks and Lamb, "Role of $NH_2$-terminal Positively Charged Residues in Establishing Membrane Protein Topology," *J. Biol. Chem.* 268:19101-19109 (1993).

\* cited by examiner

HA assay

Ampho-Retro
6:6:0
7:5:0
HN-Ampho-Retro
7:3:2
5.6:2.4:4
(MSCV:AMPHO:HN)

Dilution  2  4  8  16  20 a. SIVagm genome   SIVagm provirus genome   pSA212 b. Packaging vector   Packaging Vector
pCAG / SIVagm gag-tat / rev c. Gene transfer vector   Gene Transfer Vector
pGL3C / CMVL. U3G2 / RREc/s / CMVF β-gal / 3'LTRΔU3 d. VSV-G supplying vector  pVSV-G

SIVct/HN  WSELKTRSNDGGEGPEDANDPRGKGVQHIHIQPSLPVYGQRVRVR WLLILSFTQ

*XXX*: SIV cytoplasmic domain          XXX: HN protein transmembrane domain

Figure 15

| SIVct+HN | *WSELKIRSNDGGEGPEDANDPRGKGVQHIHIQPSLPVYGQRVRVR* DGDRGKRDS |

*XXX*: SIV cytoplasmic domain    XXX: HN protein cytoplasmic domain

Figure 16

F_ct 4    VVIIVIIIVLYRLRR
                        4

F_ct14   VVIIVIIIVLYRLRRSMLMGNPDDR
                                 14

F_ct27   VVIIVIIIVLYRLRRSMLMGNPDDRIPRDTYTLEPKIR
                                              27

XXX: F protein transmembrane   XXX: F protein cytoplasmic domain
         domain

Figure 17

```
F_ct /SIV_ct11      VVIIVIIIVL YRLRR RVRQGYVPLSP

F_ct14/SIV_ct11     VVIIVIIIVL YRLRRSMLMGNPDDR RVRQGYVPLSP

F_ct27/SIV_ct11     VVIIVIIIVL YRLRRSMLMGNPDDRIPRDTYTLEPKIR RVRQGYVPLSP

*XXX*: F protein transmembrane domain

XXX: F protein cytoplasmic          *XXX*: SIV cytoplasmic domain
            domain                                11 amino acids (SIV_ct11)
```

Figure 19

PSEUDOTYPE RETROVIRAL VECTORS CONTAINING MEMBRANE PROTEINS HAVING HEMAGGLUTININ ACTIVITY

CROSS REFERENCE TO RELATED APPLICATIONS

This application is a continuation-in-part of PCT/JP01/04659, filed Jun. 1, 2001, which, in turn, claims benefit of Japanese Application No. 2000-169090, filed Jun. 1, 2000.

TECHNICAL FIELD

The present invention relates to pseudotype viral vectors containing HN protein of paramyxovirus.

BACKGROUND ART

Retroviral vectors have been used to express foreign genes in target cells for research, gene therapy, etc. Retroviral vectors can be produced with a relatively simple method, and also have some advantages, such as, to introduce foreign genes into the chromosomes of the host. Normally, viral proteins localized in the viral envelope play a crucial role in retroviral vector infection. Much effort has been expended to widen the range of host cells to which the vectors can infect or to develop viral vectors which infect only specific cells by modifying the envelope proteins of retroviral vector.

For example, a system, where VSV-G protein is integrated into the retroviral vector envelope, has been developed to ensure the infectivity to a broader range of host cells (H. Yu et al., 1999, Gene Therapy, 6, 1876-1883). VSV-G is a protein expressed on the surface of envelope of vesicular stomatitis virus, which is infectious to a considerably broad range of host cells. In addition, for example, Sendai virus F protein has been used as an envelope protein by way of experiment. An F protein-pseudotyped retrovirus was found to exhibit specific infectivity to asialoglycoprotein receptor-positive cells (M. Spiegel et al., 1998, Hepatology, 28, 1429-1429; M. Spiegel et al., 1998, J. Virology, 72, 5296-5302).

However, these conventional pseudotype retroviruses have only insufficient infectivity to various tissues and cells. For example, a variety of stem cells including hematopoietic stem cell can be important target cells in gene therapy or the like (Y. Hanazono, Molecular Medicine, Vol. 36, No. 7, 1999), but most stem cells are in nondividing state (Abkowitz, J. L. et al., Nat Med, 2 (2), 190-7, 1996). In general, it is difficult to introduce genes using the retroviral vector exhibiting low infectivity against such nondividing cells. Further, the vector system using conventional techniques has failed to introduce genes into extracellular matrix-abundant cells such as lung airway mucosal epithelial cells. A method for introducing genes into these types of cells requires physically removing extracellular matrix, such as mucus, by welshing. However, this method is complicated and tissues can be damaged.

DISCLOSURE OF THE INVENTION

An objective of the present invention is to provide pseudotype retroviral vectors containing membrane proteins having hemagglutinin activity.

The present inventors selected proteins having hemagglutinin activity as proteins to pseudotype retrovirus. Hemagglutinin (HAin) is a protein that induces hemagglutination (HA; erythrocyte agglutination), and a number of viruses are known to have this activity. The present inventors considered that a retroviral vector capable of high efficiency gene transfer to various types of cells and tissues could be constructed based on a retrovirus with the envelope containing membrane proteins having hemagglutinin activity. In order to construct such a retrovirus, the present inventors used envelope proteins from paramyxovirus having a broad host range. First, based on a vector expressing the envelope protein of Sendai virus (SeV), a viral vector derived from a mouse retrovirus was pseudotyped by SeV F and/or HN protein. Specifically, using murine stem cell virus (MSCV) as starting material, a retrovirus was constructed to have SeV F and/or HN proteins in addition to the ecotropic envelope protein or amphotropic envelope protein; the resulting vector was tested for the efficiency of gene transfer to human cells (Examples 1 and 2).

When the packaging was carried out using the ecotropic envelope protein showing no infectivity to human cells, gene transfer to human cells was not achieved with the virus pseudotyped by F protein or HN protein alone. However, after being pseudotyped by co-expressing F protein and HN protein, the virus, which originally had no infectivity to human cells, could introduce genes into human cells (Eco in FIG. 1). This result showed that the host range for infection of the viral vector could be widened by pseudotyping a vector derived from viruses other than Sendai virus using F protein and HN protein from Sendai virus.

It was found that, when the packaging was carried out using the amphotropic envelope protein having infectivity to human cells, the efficiency of gene transfer was markedly improved by pseudotyping the virus either by expressing HN protein alone or by co-expressing F protein and HN protein (Ampho in FIG. 1). The result demonstrated that the retroviral vector could be pseudotyped by Sendai virus HN protein alone, and that the efficiency of gene transfer of retroviral vector could be improved either by pseudotyping using Sendai virus HN protein alone or by pseudotyping using Sendai virus F protein and HN protein.

The present inventors also prepared an amphotropic retroviral vector by pseudotyping with HN protein and determined the efficiency of gene transfer into human bone marrow cells including hematopoietic stem cells (Example 3). The vector pseudotyped by HN protein was infected to CD34-positive human bone marrow cells, and the cells containing the introduced gene were fractionated by flow cytometry using CD34 as a marker. The result demonstrated that the pseudotyping using HN protein markedly improved the efficiency of gene transfer into both CD34-positive and CD34-negative cells (FIG. 3). The CD34-positive cell fraction is believed to contain hematopoietic stem cells. Thus, the HN protein-based pseudotyping is also useful for gene transfer into hemocytes and hematopoietic cells including hematopoietic stem cells.

Then, using lentivirus which is expected to be more suitable as a vector for gene therapy as compared with various other types of retroviruses, the present inventors constructed a vector pseudotyped by paramyxovirus F protein and/or HN protein. The lentivirus used is simian immunodeficiency virus (SIV) (Example 5), which offers various advantages including a higher degree of safety when compared with human immunodeficiency virus (HIV) commonly used in gene therapy. SIV virus particles comprising Sendai virus (SeV) envelope protein were produced by preparing virosome containing the envelope reconstituted from SeV or inactivated Sendai virus and fusing them with SIV pseudotyped by VSV-G protein. The virus particles were incubated with human cells to assess the efficiency of vector infection (Examples 6 and 7). The result demonstrated that SIV comprising the envelope resulting from fusion with SeV envelope exhibited higher infectivity as compared with SIV pseudotyped by VSV-G protein (FIG. 8). The increased infectivity was attributable to the Sendai virus HN protein.

To precisely estimate the contribution of SeV envelope protein, the present inventors prepared FHN virosome, F virosome, and HN virosome, and prepared vectors by fusing VSV-G-pseudotyped SIV with each virosome. Then, the resulting vectors were assessed based on infection experiments (Example 7). The vector that is fused with FHN virosome showed significantly higher efficiency of gene transfer than that of SIV alone (FIG. 10). With HN virosome, the efficiency of gene transfer also improved. However, unlike FHN virosome, F virosome fusion did not result in any increase in the gene expression level. Thus, HN protein was demonstrated to be important to increase the efficiency of gene transfer.

Furthermore, using a SeV envelope protein expression vector, the present inventors produced a lentivirus vector which was pseudotyped by SeV envelope protein at the stage of packaging (Example 8). The SIV vector pseudotyped by F protein and HN protein in addition to VSV-G protein was produced at a higher titer. This viral vector could be further enriched by centrifugation. The present inventors tested the vector in in vivo gene transfer assay.

Since conventional viral vectors hardly transfer genes into mucosal cells of tracheal epithelium, a pre-treatment to remove physical barriers are required to achieve gene transfer; for example, without damaging cells by sulfur dioxide or the like, gene transfer at sufficiently high efficiency is not achieved by a gene transfer method using the VSV-G-pseudotyped HIV vector (L. G. Johnson et al., Gene Therapy, 7, 568-574, 2000). The present inventors tested whether the SIV vector pseudotyped by VSV-G protein, and Sendai virus F and HN protein allowed efficient gene transfer into mucosal cells of tracheal epithelium without inflicting such damage (Example 9). The above-mentioned pseudotype SIV vector for GFP expression was intranasally given to mice, and the expression of GFP protein was observed on tissue sections of trachea 3 days after administration; GFP fluorescence was detected in epithelial cells of the trachea (FIG. 11). Further, fluorescence signals resulted from GFP expression were also detectable in mucosal epithelium of septonasal mucus membrane and pseudostratified ciliated epithelium of the same individuals (FIG. 12). Thus, it was demonstrated that the viral vector of the present invention could introduce genes into cells having mucus, such as mucosal epithelial cells, without damaging the cells or tissues.

Furthermore, the present inventors constructed an expression vector for a modified HN protein in which the cytoplasmic domain had been altered. Using this vector, they produced a novel pseudotyped viral vector. Specifically, they constructed vectors to express a protein comprising the cytoplasmic domain of SIV envelope protein linked to SeV HN protein; a protein in which the cytoplasmic domain of SIV envelope protein had been substituted for the cytoplasmic domain of HN protein; and the SeV F protein in which the whole or a portion of the cytoplasmic domain had been deleted or replaced with the cytoplasmic domain of SIV envelope protein; then, they further constructed pseudotyped SIV vectors containing these proteins (Examples 11 and 12). It was shown that these vectors were capable of transferring genes into human cells, including 293T cells and BEAS-2B cells. Thus, HN pseudotyped vectors were found to be capable of transferring genes into human cells even in the absence of any other coexisting envelope proteins such as VSV-G. It was also shown that MSCV-based pseudotype retroviral vectors constructed using these expression plasmids for modified HN proteins were capable of transferring genes into human cells (Example 13). The pseudotyped SIV vector containing modified HN protein was prepared on a large scale, enriched, and then allowed to infect human bone marrow cells. According to this result, the vector could transfer genes into $CD34^+$ bone marrow cells with high efficiency (Example 14).

Furthermore, the present inventors prepared HA-pseudotyped lentivirus vector using the expression vector for the hemagglutinin (HA) protein of influenza virus. The resulting virus could introduce genes into human cells and be highly enriched by centrifugation (Example 16). In addition, they prepared HA/HN-pseudotyped lentivirus vector containing influenza virus HA protein and modified HN protein of Sendai virus, and confirmed that the vector could transfer genes into human cells (Example 17).

As described above, the present inventors succeeded in constructing viral vectors ensuring gene transfer at a high efficiency using retroviruses pseudotyped by membrane proteins having hemagglutinin activity. Additionally, they demonstrated that the viral vectors could transfer genes at a high efficiency into hemocytes and hematopoietic cells including hematopoietic stem cells, and cells having mucus such as mucosal epithelial cells, in ex vivo or in vivo administration.

More specifically, the present invention relates to:

(1) a substantially pure pseudotype retroviral vector that comprises a membrane protein having hemagglutinin activity;

(2) the pseudotype retroviral vector according to (1), wherein the membrane protein having hemagglutinin activity is derived from a protein having hemagglutinin activity which is contained in a single-stranded negative strand RNA virus;

(3) the pseudotype retroviral vector according to (2), wherein the membrane protein having hemagglutinin activity is derived from HN protein of paramyxovirus and/or HA protein of orthomyxovirus;

(4) the pseudotype retroviral vector according to (2), wherein the membrane protein having hemagglutinin activity is a portion or the whole of a cytoplasmic domain of a protein having hemagglutinin activity which is contained in a single-stranded negative strand RNA virus, and wherein the portion or the whole has been modified by substitution, deletion, and/or addition;

(5) the pseudotype retroviral vector according to any one of (1) to (3), further comprising F protein of paramyxovirus;

(6) the pseudotype retroviral vector according to (5), wherein a portion or the whole of a cytoplasmic domain of the F protein has been modified by deletion and/or addition;

(7) the pseudotype retroviral vector according to any one of (1) to (6), further comprising an envelope protein derived from a virus that is infectious to human cells;

(8) the pseudotype retroviral vector according to (7), wherein the vector comprises an amphotropic envelope protein derived from a retroviral;

(9) the pseudotype retroviral vector according to (7) or (8), wherein the vector comprises VSV-G protein derived from a vesicular stomatitis virus;

(10) the pseudotype retroviral vector according to any one of (1) to (9), wherein the retroviral vector is derived from oncovirus;

(11) the pseudotype retroviral vector according to any one of (1) to (9), wherein the retroviral vector is derived from lentivirus;

(12) the pseudotype retroviral vector according to (11), wherein the lentivirus is derived from simian immunodeficiency virus;

(13) the pseudotype retroviral vector according to (3) or (5), wherein the paramyxovirus is Sendai virus;

(14) the pseudotype retroviral vector according to any one of (1) to (13), wherein the vector comprises a foreign gene in an expressible manner;

(15) the pseudotype retroviral vector according to (14), wherein the vector is used for transferring genes into a cell having mucus;

(16) the pseudotype retroviral vector according to (15), wherein the cell having mucus is a mucosal epithelial cell;

(17) the pseudotype retroviral vector according to (16), wherein the mucosal epithelial cell is a mucosal epithelial cell of nasal cavity or pulmonary bronchial tube;

(18) the pseudotype retroviral vector according to (14), wherein the vector is used for transferring genes into a hemocyte or hematopoietic cell;

(19) the pseudotype retroviral vector according to (18), wherein the hemocyte or hematopoietic cell is a hematopoietic stem cell;

(20) a composition for gene transfer, the composition comprising the pseudotype retroviral vector according to any one of (14) to (19);

(21) the composition according to (20), wherein the composition is a pharmaceutical composition;

(22) a method for introducing a foreign gene into cells, the method comprising the step of contacting cells with the pseudotype retroviral vector according to any one of (14) to (19);

(23) a packaging cell for producing the pseudotype retroviral vector according to any one of (1) to (19), the cell comprising, in an expressible manner, a DNA encoding a protein having hemagglutinin activity; and

(24) a method for producing the pseudotype retroviral vector according to any one of (1) to (19), the method comprising the step of transcribing a retrovirus-derived gene transfer vector DNA in the packaging cell according to (23).

The retroviral vector of the present invention is a substantially pure pseudotype retroviral vector pseudotyped by a membrane protein having hemagglutinin activity. As used herein, the term "viral vector" refers to a viral particle capable of transferring nucleic acid molecules into a host. The term "retroviral vector" refers to a vector comprising the retrovirus backbone. The term "having the retrovirus backbone" means that nucleic acid molecules in the viral particle constituting the vector are based on the retrovirus genome. For example, a vector in which the nucleic acid molecules in the virus particle contain the packaging signal sequence derived from the retrovirus genome is one of the retroviral vectors of the present invention.

The term "retroviral vector pseudotyped by membrane proteins having hemagglutinin activity" refers to a retroviral vector containing one or more membrane proteins having hemagglutinin activity which are not contained in the natural counterpart. As used herein, the term "substantially pure pseudotype retroviral vector" refers to the pseudotype retroviral vector which does not substantially have a replicative virus having viral hemagglutinin activity except retroviral hemagglutinin activity. A preferred pseudotype retroviral vector of the present invention is a vector having substantially no replicative virus except retrovirus. The term "replicative" means that a virus replicates and produces infectious virus particles in a host cell where the viral vector has been infected. For example, in cells where the pseudotype retroviral vector has been infected, when the HA titer representing hemagglutinin activity (erythrocyte agglutination) after vector infection is not significantly elevated as compared with that at the early stage of infection, one can assess that the vector does not substantially have replicative virus containing membrane proteins having hemagglutinin activity.

The membrane protein having hemagglutinin activity may be a naturally occurring protein or an artificial protein; it is preferred that the protein has viral hemagglutinin activity. Various types of viruses have been reported to have hemagglutinin activity. The type of erythrocyte and the optimal reaction temperature to be used for detecting the hemagglutinin activity depends on the specific virus type. It has also been reported that in the case of rubella virus the reaction requires the presence of calcium ion. In the case of arbovirus, the optimal pH of the reaction falls within a very narrow range. The viral hemagglutinin is present in the virion itself in enterovirus or rubella virus, or present in smaller particles as well as in virion in arbovirus, adenovirus, etc. The poxvirus hemagglutinin is present as a non-virion particle containing lipids. The pseudotype retrovirus of the present invention may contain such proteins. Type-III adenoviruses partially agglutinate rat erythrocytes, which results in incomplete agglutination; such proteins can also be used as the membrane proteins having hemagglutinin activity.

The hemagglutinin activity (erythrocyte agglutination; HA titer) can be tested by a method known in the art (The society of research associates of The National Institute of Health, Eds., General Experimental Virology, 2nd Ed, pp. 214-225, MARUZEN CO.). The erythrocytes include, for example, those from chicken (including chick and fowl), goose, rat, guinea pig, rhesus monkey, green monkey and human. The reaction temperature may be 0° C., 4° C., room temperature, 37° C., or the like, depending an the type of protein. Exemplary conditions or erythrocyte agglutination reaction for the respective viruses are shown below:

TABLE 1

| | | | HA reaction | | |
| --- | --- | --- | --- | --- | --- |
| | Kind of virus | | Erythrocyte | Temp. | pH |
| Adeno | Type I | 3, 7, 11, 14, 16, 20, 21, 25, 28 | Rhesus monkey | 37° C. | Independent |
| | Type II | 8, 9, 10, 13, 15, 17, 19, 22, 23, 24 26, 27 | Rat | | |
| | Type III | 1, 2, 4, 5, 6 | Rat Incomplete agglutination | | |
| Entero | Coxsackle | A7 | Chicken | Room temperature | Independent |
| | | A 20, 21, 24 | Human | 4° C. | |
| | | B1 , 3, 5 | type O | 37° C. | |

TABLE 1-continued

|  | Kind of virus |  | HA reaction | | |
|---|---|---|---|---|---|
|  |  |  | Erythrocyte | Temp. | pH |
|  | Echo | 3, 6, 7, 11, 12, 13, 19, 20, 21, 24, 29 |  | 4° C. |  |
| Reo |  | 1 | Human type O | Room temperature | Independent |
|  |  | 2 |  |  |  |
|  |  | 3 | Cattle |  |  |
| Myxo | Influenze | A | Chicken, human or guinea pig | Room temperature | 7.2 |
|  |  | B |  |  |  |
|  |  | C | Chicken | 4° C. |  |
|  | Mumps |  | Chicken |  |  |
|  | Newcastle disease (NDV) |  |  | Room temperature |  |
|  | Para-influenza | 1 | Chicken or human | 4° C. | Independent |
|  |  | 2 | Chicken |  |  |
|  |  | 3 | Human or guinea pig | 4° C. or room temp. |  |
|  | Measles |  | Green monkey | 37° C. |  |
|  | Arbo |  | Goose or chick | 37° C. | Strictly acidic |
| Rhabdo | Rabies |  | Goose | 0° C. | 6.4 strictly |
|  | Vesicular stomantus (VSV) |  |  |  | 5.8 strictly |
| Pox | Vaccinia, Variola |  | Chicken | Room temp. or 37° C. | Independent |
|  | Rubella |  | Chick or goose | 4° C. | 6.2 or 7.2 |
|  | Polyoma |  | Guinea pig | 4° C. | 7.2 |
|  | Rat (RV) |  | Guinea pig | Room temperature | 7.2 |

Particularly preferred membrane proteins having hemagglutinin activity in the pseudotype retrovirus of the present invention are viral proteins; specifically, such proteins include HN proteins of Paramyxovirus; HA proteins of orthomyxovirus and influenza virus; togaviral E1 protein; A27L, H3L, and D8L proteins of vaccinia virus; M and E proteins of flavivirus; E1 and E2 proteins of coronavirus; G1 protein of bunyavirus, etc. Among others, proteins from single-stranded negative strand RNA viruses are preferred, and HN protein of paramyxovirus is particularly preferred, as a membrane protein having hemagglutinin activity to be contained in the pseudotype retrovirus of the present invention.

As used herein, the term "single-stranded negative strand RNA virus" refers to a virus whose genome comprises a single-stranded negative strand (namely, (−) strand) RNA. Such viruses include paramyxovirus (Paramyxoviridae; including the genus Paramyxovirus, the genus Morbillivirus, the genus Rubulavirus, the genus Pneumovirus, and such), rhabdovirus (Rhabdoviridae; including the genus Vesiculovirus, the genus Lyssavirus, the genus Ephemerovirus, and such), filovirus (Filoviridae), orthomyxovirus (Orthomyxoviridae; including influenza viruses A, B, and C, Thogoto-like viruses, and such), bunyavirus (Bunyaviridae; including the genus Bunyavirus, the genus Hantavirus, the genus Nairovirus, the genus Phlebovirus, and such), arenavirus (Arenaviridae), etc.

As used herein, the term "paramyxovirus" refers to a virus belonging to the family of paramyxovirus (Paramyxoviridae). The paramyxovirus includes, for example, Sendai virus, Newcastle disease virus, Mumps virus, Measles virus, RS virus (Respiratory syncytial virus), rinderpest virus, distemper virus, monkey parainfluenza virus (SV5), human parainfluenza viruses' type-1, -2, and -3, etc. Sendai virus includes wild-type strains, mutant strains, laboratory strains, artificially constructed strains, etc. Incomplete viruses such as DI particles (J. Virol. 68, 8413-8417(1994)), synthesized oligonucleotides, etc. can also be used as material to produce vaccines of the present invention. HN protein is a protein of paramyxovirus virus. Known genes encoding paramyxovirus viral proteins include NP, P, M, F, HN, and L genes. "NP, P, M, F, HN and L genes" of viruses belonging to the family Paramyxoviridae correspond to genes encoding nucleocapsid, phospho, matrix, fusion, hemagglutinin-neuraminidase and large proteins. Respective genes of viruses belonging to subfamilies of the family Paramyxoviridae are represented in general as follows. NP gene is generally described also as the "N gene".

| Genus Paramyxovirus | NP | P/C/V | M | F | HN | — | L |
| Genus Rubullavirus | NP | P/V | M | F | HN | (SH) | L |
| Genus Morbillivirus | NP | P/C/V | M | F | H | — | L |

Database accession numbers for nucleotide sequences of genes of the Sendai virus classified into Paramyxovirus of the family Paramyxoviridae are, M29343, M30202, M30203, M30204, M51331, M55565, M69046 and X17218 for NP gene, M30202, M30203, M30204, M55565, M69046, X00583, X17007 and X17008 for P gene, D11446, K02742, M30202, M30203, M30204, M69046, U31956, X00584 and X53056 for M gene, D00152, D11446, D17334, D17335, M30202, M30203, M30204, M69046, X00152 and X02131 for F gene, D26475, M12397, M30202, M30203, M30204, M69046, X00586, X02808 and X56131 for HN gene, and D00053, M30202, M30203, M30204, M69040, X00587 and X58886 for L gene.

As described herein in Examples, a retroviral vector pseudotyped by paramyxoviral envelope proteins can be produced by preparing inactivated paramyxovirus, virosome having the envelope protein of paramyxovirus, etc. and fusing it with retrovirus. The vector can also be produced by expressing an expression vector for the paramyxovirus envelope proteins in retrovirus packaging cells.

The pseudotype retroviral vector of the present invention can comprise, for example, F protein of paramyxovirus in addition to membrane proteins having hemagglutinin activity such as HN protein of paramyxovirus. The present invention demonstrated that the pseudotype retroviral vector containing HN and F proteins exhibited high efficiency of gene transfer. Pseudotype retroviral vectors containing the F and HN proteins are within the scope of the present invention. The pseudotype retroviral vector of the present invention may further contain M protein of paramyxovirus.

Furthermore, the pseudotype retroviral vector of the present invention can contain additionally envelope proteins derived from other viruses. For example, preferred envelope proteins include those derived from viruses infectious to human cells. Such proteins include, but not limited to, amphotropic envelope proteins of retrovirus, G protein of vesicular stomatitis virus (VSV), etc. Such proteins of viruses belonging to the herpes viridae include, for example, gB, gD, gH and gp85 proteins of herpes simplex virus, gp350 and gp220 proteins of EB virus, etc. Such proteins of viruses belonging to the hepadna viridae include S protein of hepatitis B virus, etc.

For example, a vector comprising retroviral amphotropic envelope (amphotropic env) protein and HN protein is preferred as a vector of the present invention. Alternatively, for example, the vector can contain VSV-G protein that is a surface glycoprotein of vesicular stomatitis virus (VSV). VSV-G has been believed to use phospholipid as a receptor, which exists in most animal cells, and thus, by using a vector containing VSV-G protein and HN protein, the variety of cells into which genes can be introduced is dramatically increased and the transfer efficiency is also elevated. Indeed, the vector containing VSV-G protein and HN protein exhibited higher efficiency of gene transfer than the vector containing VSV-G alone. Accordingly, the vector containing VSV-G protein and HN protein is a preferred vector of the present invention. Such vectors may further contain paramyxovirus F protein. In summary, both vector containing retroviral amphotropic envelope protein, F protein, and HN protein, and vector containing VSV-G protein, F protein, and HN protein are within the scope of the present invention. In addition, these vectors may further contain M protein of paramyxovirus. Specifically, both vector containing retroviral amphotropic envelope protein, F protein, HN protein, and M protein, and vector containing VSV-G protein, F protein, HN protein, and M protein are within the scope of the present invention. The vector containing paramyxoviral F and HN proteins, and the vector containing F, HN and M proteins, as described above, also transferred genes at a high efficiency into cells having mucus, cell fractions containing hematopoietic stem cells, or the like, into which genes were hardly transferred by the conventional techniques.

Since VSV-G protein is a glycoprotein and forms a stable homotrimer on the membrane, the vector particles are scarcely disrupted during purification; thus the particles can be concentrated to a high level by centrifugation (Yang, Y. et al., Hum Gene Ther: September, 6(9), 1203-13. 1995). The present inventors confirmed that the SIV vectors pseudotyped by VSV-G and by F and HN could be concentrated by centrifugation.

There is no limitation on the types of paramyxovirus HN, F, and M proteins to be used to prepare pseudotyped vectors. Particularly, the proteins of Respirovirus including Sendai virus are preferred. The HN, F, and M proteins of Sendai virus include, for example, those from Z strain. The retroviral amphotropic envelope proteins include, for example, the envelope proteins from mouse leukemia virus (MuLV) 4070A strain. The MuMLV 10A1-derived envelope proteins can also be used (for example, pCL-10A1 (Imgenex) (Naviaux, R. K. et al., J. Virol. 70: 5701-5705 (1996)). The ecotropic envelope proteins include, for example, the envelope proteins from Moloney murine leukemia virus (MoMULV). Vesicular stomatitis virus G protein (VSV-G) includes, for example, the protein derived from Indiana serotype strain (J. Virology 39: 519-528 (1981)). In addition to these, the proteins may be derived from desired strains.

The above-mentioned envelope proteins, including HN, F, M, VSV-G, and retroviral envelope proteins, may be intact proteins from wild-type viruses or mutated proteins spontaneously or artificially. For example, HN protein, which is a structural protein, has both hemagglutinin (which is erythrocyte agglutination) activity and neuraminidase activity. For example, the reduction of the former activity may increase viral stability in blood. For example, the efficiency of infection via HN protein can be controlled by modifying the latter activity. Alternatively, the fusion efficiency can be controlled by modifying F protein that participates in the membrane fusion. Further, for example, the antigen presenting epitopes of F protein and HN protein that can serve as cell-surface antigen molecules are analyzed, and based on the analysis result, pseudotype retroviruses of the present invention can be prepared by using the proteins whose antigen presenting ability has been impaired. In addition, it is possible to use the envelope proteins of attenuated strains of pathogenic paramyxoviruses.

For example, higher efficiency gene transfer vectors can be prepared by pseudotyping the retroviral vector of the present invention by using modified proteins that are the viral envelope proteins having hemagglutinin activity or other envelope proteins whose cytoplasmic domains have been modified by deletion, substitution and/or addition. The present invention relates to pseudotype retroviral vectors comprising proteins in which a portion or the whole of a cytoplasmic domain of wild-type membrane proteins having hemagglutinin activity has been modified by substitution, deletion, and/or addition. Specifically, for example, modified HN protein and/or F protein of paramyxovirus, in which the cytoplasmic domain has been deleted, or a cytoplasmic domain from another membrane protein (for example, the envelope protein of retrovirus including lentivirus) has been substituted for or added to the original one, can be used preferably to produce a viral vector with high infectivity. The present invention provides a membrane protein having hemagglutinin activity in which a portion or the whole of a cytoplasmic domain of the wild type of the membrane protein has been modified by substitution, deletion, and/or addition, and the nucleic acid encoding the protein (DNA, RNA, or the like). Particularly, the present invention provides a modified viral hemagglutinin protein whose cytoplasmic domain has been modified by substitution, deletion, and/or addition, and the nucleic acid encoding the protein. For example, a modified HN protein comprising the amino acid sequence of SEQ ID NO: 40 or 41 is preferred.

Such modified proteins and the nucleic acids encoding the proteins are useful to produce pseudotype viruses of the present invention.

Specifically, foreign genes can be introduced with high efficiency into a wide variety of cells including human cells, by using retrovirus pseudotyped with a modified paramyxovirus HN protein whose cytoplasmic domain has been replaced with the cytoplasmic domain of envelope protein of lentivirus such as SIV, or retrovirus (for example, the protein encoded by pCAGGS-SIVct/HN according to Example 11); or another modified protein in which the cytoplasmic domain of envelope protein of retrovirus such as lentivirus has been added to paramyxovirus HN protein (for example, pCAGGS-SIVct+HN according to Example 11). Arbitrary portions of the cytoplasmic domain of HN protein can be deleted; arbitrary portions of the cytoplasmic domain of retroviral envelope protein can be added; a portion or the whole of cytoplasmic domain may be deleted, substituted, and/or added.

Such a viral vector can contain additionally a modified F protein of paramyxovirus. For example, it is possible to use an F protein of paramyxovirus whose cytoplasmic domain has been deleted, or a protein obtained by adding the cytoplasmic domain of envelope protein of lentivirus such as SIV, or retrovirus to Such truncated protein. Specifically, for example, a plasmid in constructed to express an F protein whose cytoplasmic domain amino acids are deleted. Any portions of the domain can be deleted; a portion or the whole of cytoplasmic domain can be deleted. The pseudotype virus containing a truncated Sendai virus F protein (Fct4) that had only four amino acids of the cytoplasmic domain by deleting the remaining exhibited significantly high efficiency of gene transfer. Thus, the protein that contains none or only several amino acid residues of the cytoplasmic domain due to an artificial deletion can be preferred to produce a pseudotype virus of the present invention. A protein in which the cytoplasmic domain of F protein has been substituted with a distinct peptide can be produced by attaching a portion or the whole of cytoplasmic domain of envelope protein of another virus (for example, lentiviral envelope protein) to these truncated F proteins. For example, such proteins include the protein to which the first 11 amino acids of the cytoplasmic domain of SIV envelope protein from its 5' end (SIVct11) have been attached. Thus, the present invention provides a paramyxovirus F protein in which a portion or the whole of cytoplasmic domain of the wild type of the protein has been modified by substitution, deletion, and/or addition, and the nucleic acid encoding the protein. In particular, the present invention provides an F protein whose cytoplasmic domain has been replaced with a portion of or the whole of a cytoplasmic domain of the envelope protein from a retrovirus including lentivirus, and the nucleic acid encoding the protein. For example, a modified F protein comprising the amino acid sequence of SEQ ID NO: 42, 43, 44, 45, 46, or 47 is preferred. These modified proteins and the nucleic acids encoding the proteins can be used to produce pseudotype viruses of the present invention.

It is also preferred that HA protein of a virus belonging to the Orthomyxoviridae is used as the viral envelope protein having hemagglutinin activity. For example, a pseudotype virus produced by using an expression plasmid for influenza virus envelope protein is infectious to a wide variety of mammalian cells including human cells. The influenza virus envelope may be derived from a desired strain of isolated influenza virus. In the budding of influenza virus, neuraminidase in responsible for the cleavage of the linkage with sialic acid. Thus, infectious virus particles pseudotyped by HA can be prepared by the treatment with neuraminidase. Alternatively, the linkage with sialic acid can be cleaved automatically by using a viral vector that also encodes a protein having neuraminidase activity. In such cases, it is particularly preferred to use a viral envelope protein having neuraminidase activity, such as HN protein of paramyxovirus. Thus, the present invention provides retroviral vector pseudotyped by HA/HN protein.

The retroviral vector of the present invention also includes those derived from oncovirus. The term "oncovirus" refers to retroviruses belonging to the oncovirus subfamily (Oncovirus). The oncovirus includes retroviruses involved in canceration, such as sarcoma virus, leukemia virus, mammary tumor virus, etc. For example, Moloney murine leukemia virus (Mo-MLV) is one of the earliest developed retroviral vectors, which has a number of improvements and is widely used. A viral vector prepared by pseudotyping MoMLV with a protein having hemagglutinin activity, such as paramyxovirus HN protein, can be used preferably in the present invention. In addition, murine stem cell virus (MSCV) used in Example is a preferred gene-transfer vector particularly in transferring genes into hemocytes, hematopoietic cells, embryonic stem cells, etc.

The retroviral vector of the present invention also includes those derived from lentivirus The term "lentivirus" refers to a retrovirus belonging to the lentivirus subfamily (Lentivirus). The lentivirus includes human immunodeficiency virus (HIV) (e.g., HIV1 or HIV2), simian immunodeficiency virus (SIV), feline immunodeficiency virus (FIV), Maedi-Visna virus, equine infectious anemia virus (EIAV), caprine arthritis-encephalitis virus (CAEV), etc. The retroviral vector of the present invention can be derived from a desired strain or subtype. For example, HIV-1 includes those of every major (M) subtype (including A to J), N, and outlier (O) (Hu, D. J. et al, JAMA 1996; 275: 210-216; Zhu, T. et al., Nature 1998, 5; 391(6667): 594-7; Simon, F. et al., Nat. Med. 1998, 4-(9): 1032-7). Isolated SIV strains include, for example, SIVagm, SIVcpz, SIVmac, SIVmnd, SIVsnm, SIVsyk, etc.

Lentiviruses are infectious to nondividing cells and the virus genome can be integrated into host cell chromosome. The nuclear translocation signals encoded by gag and vpr are believed to be responsible for the integration. When, using this characteristic, a viral vector of the present invention is constructed based on a lentivirus, genes can be introduced into nondividing cells in living tissues and cells that hardly divide, such as stem cells in various tissues, which allows long-term gene expression.

Human immunodeficiency virus (HIV), before any other lentivirus, was used to construct a vector, which can also be used preferably in the present invention. Vectors have been developed based on feline immunodeficiency virus (FIV) (Poeschla, E. M. et al., Nature Medicine, 4(3), 354-7, 1998) and caprine arthritis-encephalitis virus (CAEV) (Mselli-Lakhal, L. et al., Arch. Virol., 143(4), 681-95, 1998). These vectors can be used to produce vectors of the present invention.

Simian immunodeficiency virus (SIV) was discovered as a monkey-derived HIV-like virus, which, along with HIV, forms the group of primate lentivirus (E. Ido and M. Hayamizu, "Gene, Infection and Pathogenicity of Simian Immunodeficiency Virus", Protein, Nucleic acid and Enzyme, Vol. 39, No. 8, 1994). This group is further divided roughly into four subgroups: (1) HIV-1 subgroup containing HIV-1 that is the causative virus for human acquired immune deficiency syndrome (AIDS) and SIVcpz isolated from chimpanzee; (2) HIV-2 subgroup containing SIVsmm isolated from Sooty Mangabey (*Cercocebus atys*) SIVmac isolated from rhesus monkey (*Macaca mulatta*), and HIV-2 that is less pathogenic in human (Jaffar, S. et al., J. Acquir. Immune Defic. Syndr. Hum. Retrovirol., 16(5), 327-32, 1997); (3) SIVagm subgroup represented by SIVagm isolated from African green monkey (*Cercopithecus aethiops*); and (4) SIVmnd subgroup represented by SIVmnd isolated from Mandrill (*Papio sphinx*).

There is no report suggesting the pathogenicity of SIVagm and SIVmnd in natural hosts (Ohta, Y. et al., Int. J. Cancer, 15, 41(1), 115-22, 1988; Miura, T. et al., J. Med. Primatol., 18(3-4), 255-9, 1989; M. Hayamizu, Nippon Rinsho, 47, 1, 1989). In particular, previous reports describe that, according to the results of infection experiments, the TYO-1 strain, which is one of SIVagm and was also used herein in the Examples, is not pathogenic in crab-eating monkey (*Macaca facicularis*), rhesus monkey (*Macaca mulatta*) as well as in natural hosts (Ali, M. et al, Gene Therapy, 1(6), 367-84, 1994; Honjo, S et al., J. Med. Primatol., 19(1), 9-20, 1990). There is no report on SIVagm infection to humans and the onset thereof, and thus it is believed that SIVagm may not be pathogenic to human. In general, lentiviruses in primate has strict species-specificity, and there are few reports on cases where cross-species infection with SIVagm from natural hosts and onset thereof; if any, normally the onset frequency is low and the disease progresses slowly (Novembre, F. J. et al., J. Virol., 71(5), 4086-91, 1997). Accordingly, a viral vector prepared based on SIVagm, particularly SIVagm TYO-1, is thought to be safer than vectors based on HIV-1 or other lentiviruses, and thus can be used preferably in the present invention.

Furthermore, the retroviral vector of the present invention includes those derived from spumavirus. The spumavirus includes, for example, foamyvirus (DE4318387; WO9607749; Virology (1995) 210, 1, 167-178; J. Virol. (1996) 70, 1, 217-22). Vectors of the present invention derived from foamyvirus can be utilized for introducing foreign genes into human cells, particularly in gene therapy and administration of recombinant vaccines.

In the retroviral vector of the present invention, LTR (long terminal repeat) may be modified. LTR is a retrovirus-specific sequence, which is present in the virus genome at both ends. 5' LTR serves as a promoter, which enhances the mRNA transcription from the provirus. Thus, a substitution of the portion exhibiting the 5' LTR promoter activity in the gene transfer vector with another promoter having stronger promoter activity can lead to increased levels of mRNA transcription of the gene transfer vector, which may improve the packaging efficiency and thus increase the vector titer. Furthermore, for example, in the case of lentivirus, the transcription activity of 5' LTR is known to be enhanced by viral tat protein, and therefore substitution of a tat protein-independent promoter for 5' LTR allows the exclusion of tat from the packaging vector. The intracellular RNA of virus infected to cells is reverse transcribed and forms a closed circular structure with a linkage between the LTRs at the two ends, and then integrated into the chromosome of cells through the interaction between the linkage site and viral integrase. The mRNA transcribed from the provirus corresponds to the region from the transcription initiation site in the 5' LTR to the 3' LTR polyA sequence that located downstream; the 5' LTR promoter portion is not packaged in the virus particle. Thus, even if the promoter is replaced with another sequence, the portion that is integrated into the chromosome of target cells has no alteration. Based on the facts described above, a substitution of 5' LTR promoter can provide a safer vector with a higher titer. Thus, a substitution of the promoter at the 5' end in a gene transfer vector can increase the titer of packagable vectors.

The safety can be improved with a self inactivating vector (SIN vector) which is prepared by partially eliminating the 3' LTR sequence to prevent the transcription of full-length vector mRNA in target cells thereof. The provirus for lentivirus, which is integrated into the chromosome of target cells, has the U3 portion of 3' LTR attached to the 5' end thereof. Thus, in the chromosome of target cells, the gene transfer vector contains U3 at the 5' end and accordingly the transcription of RNA covering the whole gene transfer vector starts there. If there were lentivirus or related proteins in the target cells, the gene transfer vector would be re-packaged and infect other cells. Furthermore, there is a possibility that a host gene located adjacent to the 3' end of virus genome may be expressed by the 3' LTR promoter (Rosenberg, N., Jolicoeur, P., Retroviral Pathogenesis. Retroviruses. Cold Spring Harbor Laboratory Press, 475-585, 1997). Such events are recognized as being problematic with retroviral vectors. Thus, the SIN vector was developed as a solution to overcome the problems (Yu, S. F. et al., Proc. Natl. Acad. Sci. USA, 83(10), 3194-8, 1986). When the U3 portion is deleted from the 3' LTR in the gene transfer vector, neither 5' LTR nor 3' LTR promoter is present in the target cells. In such cases, neither full-length viral RNA nor host gene is transcribed, while the transcription of genes of interest is achieved with internal promoters; such a vector can be an overexpression vector with higher safety, and thus is preferable in the present invention. SIN vectors can be constructed according to any of methods known in the art or the method as described in Example 5.

Retroviruses can be produced by transcribing a gene transfer vector DNA containing the packaging signal in host cells, and allowing virus particles formation in the presence of gag and pol proteins, and envelope proteins. The gene transfer vector DNA may be a DNA vector such as plasmid, or a DNA that has been integrated in the chromosome of packaging cells. While it is preferable to integrate the packaging signal sequence encoded by the gene transfer vector DNA as long as possible to maintain the structure formed based on the sequence, it is required to minimize the sequence homologous between the packaging signal in the vector DNA and another packaging vector for providing gag and pol proteins to reduce the frequency of wild-type virus formation due to recombination between the types of vectors. Accordingly, it is preferable to construct the gene transfer vector DNA using as short a sequence as possible comprising the sequence required for packaging to meet both criteria of packaging efficiency and safety.

There is no limitation on the type of packaging signal, as long as packaging is achieved in cells where the packaging vector has been introduced; those derived from retrovirus, lentivirus, immunodeficiency virus, and the like can be used depending on the type of packaging vector.

For example, in the case of SIVagm-derived packaging vector used in the Example, the type of virus from which the signal to be used is derived is limited to SIV because HIV vectors are not packaged. However, the SIV-derived gene transfer vector is also packagable when an HIV-derived packaging vector is used. Thus, the frequency of recombinant virus formation can be reduced when the vector particles are formed by combining gene transfer vector and packaging vector, each derived from different type of lentivirus. In such cases, it is preferred to use combinations of lentiviruses in primates (for example, HIV and SIV).

In a preferred gene transfer vector DNA, gag protein has been modified so that it is not expressed. The viral gag protein can be detected as a foreign substance in the living body, and thus a potential antigen. Alternatively, the protein may affect cellular functions. To prevent the gag protein expression, frameshift mutations can be introduced for modification by adding or deleting nucleotides downstream of the start codon of gag. It is also preferable to delete portions of the coding region of gag protein. In general, a 5' portion of the coding region of gag protein is known to be essential for virus packaging. Thus, In a gene transfer vector, it is preferred that the coding region for the gag protein is deleted at the C terminus. It is preferred to delete as large a portion of gag coding region as possible, as long as the deletion does not considerably affect the packaging efficiency. In addition, it is preferred to replace the start codon (ATG) of gag protein with a codon other than ATG Such a codon for the replacement can be selected appropriately not to greatly affect the packaging efficiency. A viral vector containing the transcription product of gene transfer vector DNA can be produced by introducing the constructed gene transfer vector DNA comprising the packaging signal into appropriate packaging cells. The viral vector particles produced can be recovered from the culture supernatant of packaging cells, or the like.

There is no limitation on the type of packaging cell, as long as the cell line is generally used in viral production. When used for the purpose of gene therapy in human, a human or monkey-derived cell is suitable. Human cell lines to be used as packaging cells include, for example, 293 cell, 293T cell, 293EBNA cell, SW480 cell, u87MG cell, HOS cell, C8166 cell, MT-4 cell, Molt-4 cell, HeLa cell, HT1080 cell, TE671 cell, etc. Monkey cell lines include, for example, COS1 cell, COS7 cell, CV-1 cell, BMT10 cell, etc. In addition, previously established packaging cells can be used. Such packaging cells include, for example, Bosc23 cell, PE501 cell, etc.

There is no limitation on the type of foreign gene to be inserted in the vector, which include, for example, nucleic acids which do not encode any protein, such as antisense or ribozyme, as well as protein-encoding nucleic acids.

In recent years, attention is being given to a variety of stem cells including hematopoietic stem cells as targets of gene therapy (Y. Hanazono, Molecular Medicine, Vol. 36, No. 7, 1999). As shown in Example, the pseudotype retroviral vector of the present invention can transfer genes into CD34-positive cells derived from human bone marrow with high efficiency; such a fraction comprising the CD34-positive cells receives attention as a cell fraction containing hematopoietic stem cells in recent years. Previous reports describe that the CD34-positive cells exhibit pluripotency in colony assay using a culture medium containing methylcellulose (Kirshenbaum, A. S. et al., J. Immunol., 148(3), 772-7, 1992) and that transplantation of CD34-positive cells into NOD/SCID mouse that is a compounded immunodeficiency strain leads to localization of the cells in the mouse bone marrow and reconstitution of hemopoietic system (Larochelle, A. et al., Nat. Med., 2(12), 1329-37, 1996). Hence, it is though that stem cell-like immature cells are present in at least the CD34-positive cell fraction. The hematopoietic stem cells in the CD34-positive cell fraction are in nondividing state. In general, when a retroviral vector is used, the efficiency of gene transfer into such cells is low (Kiem, H. P. et al., Curr. Opin. Oncol., 7(2), 107-14, 1995.), but the infection efficiency can be greatly improved by using the pseudotyped vector of the present invention. In particular, the efficiency of gene transfer into nondividing cells is expected to further increase by the use of a lentivirus vector, such as HIV or SIV vector. The present invention relates to a method for introducing genes into hemocytes or hematopoietic cells, in which the method comprises a step of contacting pseudotype retroviral vector containing membrane proteins having hemagglutinin activity with hemocytes or hematopoietic cells, and the use of the pseudotype retroviral vector containing membrane proteins having hemagglutinin activity to introduce genes into hemocytes or hematopoietic cells. The retroviral vector of the present invention, pseudotyped by the use of proteins having hemagglutinin activity, can transfer genes into hemocytes and hematopoietic cells with high efficiency, and thus is useful in gene therapy whose target is blood cells, e.g., adenosine deaminase (ADA) deficiency (Blaese, R. M., Pediatr. Res., 33 (1 Suppl), S49-53, 1993), hemophilia (Kay, M. A. et al., Proc. Natl. Acad. Sci. USA, 96(18), 9973-5, 1999) and Fanconi anemia, etc. The administration can be performed, for example, by an ex viva method.

Evaluation for the achievement of introduction of foreign genes into hemocytes and hematopoietic cells can be made, for example, by flow cytometry analysis using antibodies against various known surface antigens or by colony assay, or through assessing hemopoietic cell transplantation-based reconstitution of hemopoietic system in mice whose hemopoietic system has been disrupted.

Gene therapy whose targets are hemopoietic cells, to which the vector of the present invention is applicable, includes, for example, use of the drug resistance gene MDR1 to preserve stem cells in anti-cancer chemotherapy (Licht, T. et al., Gene Ther. (2000) 7, 4, 348-58); introduction of the normal FANCC gene for the treatment of Fanconi anemia (Liu, J. M. et al., Hum. Gene Ther. (1999) 10, 14, 2337-46); introduction of a combination of cytokines (thrombopoietin, interleukins 6 and 11, and Flt-3 ligand) to enhance the ex vivo proliferation of stem cells (WO 9907831); the expression of chimeric proteins, such as Flt-3 agonist, to treat cytopenia (WO 9846750); introduction of the human β globin gene to treat β thalassemia (WO 9741141); a combination therapy with IL-6 antagonist and suicide gene expression to treat IL-6-dependent multiple myeloma (German Patent No. DE19704979); introduction of genes such as receptor agonist comprising a combination of hemopoietic factors [interleukins (GM-CSF, G-CSF-Ser17, M-CSF, erythropoietin, IL-1, IL-14, IL-2, IL-5, IL-6, IL-7, IL-8, IL-9, IL-10, IL-11, IL-12, IL-13, and IL-15), leukemia inhibitory factor (LIF), flt3/flk2 ligand, human somatotropin, B cell growth factor, B cell differentiation factor, erythrocyte differentiation factor (EDF) or stem cell factor (SCF)] (WO 9712985), c-mpl receptor agonist to be used in stem cell culture and gene therapy for hemopoietic diseases (WO 9712978), IL-6 and IL-6 soluble receptor fusion protein to be used for the proliferation of human hemopoietic progenitor cells (Nat. Biotechnol. (1997) 15, 2, 142-45), IL-6 superagonist and superantagonist to be used to proliferate hemopoietic progenitor cells (WO 9618648), Factor-X to be used in therapy for blood diseases (J. Cell. Bioche. (1995) Suppl. 21A, 410), stem cell factor, IL-6, and soluble IL-6 receptor complex to be used to proliferate human hemopoietic progenitor cells (Gene Ther. (1995) 2, 9, 694), ribozyme whose targets are RNA viruses, and antisense and/or decoy RNA which are useful to prevent HIV infection and for intracellular immunity (WO 9622368).

The HN protein-pseudotyped retroviral vector of the present invention is highly infectious to cells containing mucus, such as mucosal epithelial cells of nasal cavity and epithelial cells of bronchial mucus membrane In the lung. The vector of the present invention is useful for high efficiency transfer of foreign genes into cells containing mucus, into which genes are hardly transferred by any of the conventional methods. The present invention relates to a method for introducing genes into cells containing mucus, in which the method comprises a step of contacting a pseudotype retroviral vector containing membrane proteins having hemagglutinin activity with cells containing mucus, and the use of the pseudotype retroviral vector containing membrane proteins having hemagglutinin activity to introduce genes into cells containing mucus. Such cells containing mucus include mucosal epithelial cell in particular, specifically for example, mucosal epithelial cells of nasal cavity or pulmonary bronchial tubes.

Specific examples for the use include, for example, the induction of immunoreaction through gene transfer (IL-2, IFN-γ, TGF-β, etc.) into skin and mucous membrane where antigen presenting cells (APC) are advantageously abundant (WO 9505853); vaccination against rotavirus by oral administration of genes to mucous membrane (J. Virol. (1998) 72, 7, 5757-61); mucosal administration to treat autoimmune diseases (WO 9746253); mucosal administration to prevent infection (WO 9621356); administration of genes to mucous membrane of female genital organs to prevent caner of the cervix uteri caused by sex-transmitted diseases or papilloma virus infection (Infect. Immun. (1998) 66, 1, 322-29); and improvement of administration simplicity and safety by administration via mucous membrane (Proc. Am. Assoc. Cancer Res. (1995) 36, 86 Meet., 418).

The pseudotype retroviral vector of the present invention can be prepared as a composition by appropriately combining with pharmaceutically acceptable carrier or medium. Specifically, for example, the vector can be formulated as a composition appropriately in combination with sterilized water, physiological saline, culture medium, serum, phosphate-buffered physiological saline (PBS), etc. The composition may further contain other components including stabilizer, antimicrobial, etc. The composition of the present invention can be in a dosage form such as aqueous solution, capsule, suspension, syrup, etc. A composition comprising the pseudotype retroviral vector of the present invention is useful as a reagent or a pharmaceutical. For example, a composition of the present invention can be used as a reagent for in vitro or in vivo gene transfer into various cells, or as a pharmaceutical for ex vivo or in vivo gene therapy. In general, the administration to patients can be achieved, for example, by a method known to those skilled in the art, including intraarterial, intravenous, intraperitoneal, subcutaneous, enteral, oral, or intranasal administration, or ex vivo administration. In particular, administration to mucous membrane of the nasal cavity or bronchial tubes, and ex vivo administration to hemocytes and hematopoietic cells are suitable.

The viral vector of the present invention can be used in gene therapy for various other genetic diseases. There is no limitation on the type of disease to be treated, For example, diseases to be treated and the single causative genes thereof include: Gaucher disease, β-cerebrosidase (chromosome 20); hemophilia, blood coagulation factor VIII (X chromosome) and blood coagulation factor IX (X chromosome) adenosine deaminase deficiency, adenosine deaminase; phenylketonuria, phenylalanine hydroxylase (chromosome 12), Duchenne muscular dystrophy, dystrophin (X chromosome); familial hypercholesterolemia, LDL receptor (chromosome 19), cystic fibrosis, chromosomal translocation of CFTR gene. The targeted disease in which other multiple genes are thought to be involved include neurodegenerative diseases such as Alzheimer's disease and Parkinson's disease, ischemic encephalopathy, dementia, and intractable infection such as AIDS. A treatment to inactivate the HIV transcription factor may be considered, therein an SIV based vector of this invention is worked in vitro into a hematopoietic stem cell removed from an AIDS patient extracellularly, for increasing the transcription of SIV-derived genome prior to HIV infection, and the transfected cell is returned to the patient's body. Furthermore, examples of applications possible for chronic diseases include: suppression of the expression of VEGF and FGF2 genes for ischemic heart disease, and suppression of the expression of cell proliferation related genes, such as cell proliferation factors (PDGF, TGF-β, etc.) and cyclin-dependent kinase, for gene therapy of arteriosclerosis. In addition, for diabetes, the BDNF gene may be a candidate. Furthermore, this method can be applied to substitution therapy, in which a gene such as a cancer suppressor gene, p53, whose genetic mutation causes canceration, is integrated into the chromosome, and this method enables treatment beyond the limitation of cancer pharmacotherapy by introducing a multiple-drug-resistant gene into bone marrow-derived hematopoietic stem cells in vitro and, then, by returning these cells into patient's blood. Regarding gene therapy of autoimmune diseases such as multiple sclerosis, chronic rheumatoid arthritis, SLE, and glomerulonephritis, expression suppression by antisense expression of T-cell receptors, various adhesion factors (for example, ICAM-1, LFA-1, VCAM-1, and LFA-4 etc.), cytokines and cytokine receptor (for example, TNF, IL-8, IL-6, and IL-1 etc.) cell proliferation factors (for example, PDGF, and TGF-β etc.), and activation factors (for example, MMP etc.) become possible. Regarding gene therapy of allergic diseases, expression suppression by antisense expression of IL-4, FcεR-I, and such becomes possible. Regarding gene therapy relating to organ transplantation, the elevation of success percentage or a xenotransplant becomes possible by changing the histocompatibility antigen of a non-human animal donor to a human-type. Furthermore, treatment by introducing foreign genes into the chromosome of human ES cells, thus making up the deficient genes at the embryonic stage to supplement deficiencies of systemically circulating enzymes, growth factors, and such may be considered.

For example, IL-4 promotes differentiation of helper T lymphocyte into Th2 lymphocyte. Th2 lymphocyte secretes cytokines, such as IL-4, IL-5, IL-9, and IL-13, which mediate asthmatic inflammation. IL-4 is a molecule that induces mucus secretion from lung mucus membrane, which is involved in respiratory disturbance. IL-4 regulates the expression of VCAM-1 that is a cell adhesion molecule interacting with VLA 4 molecule present on the surface of eosinophil. The interaction allows eosinophils to migrate from blood to inflammation sites in lung tissues. Since IL-4 increases the number of B cells and induces the production of antigen-specific IgE responsible for allergic reactions. The antigen-specific IgE produced induces the release of inflammatory mediators, such as histamine, leukotriene, from mast cells, which results in bronchoconstriction. Based on such role of IL-4, expression vectors for soluble interleukin 4 (IL-4) receptor etc. can be used to treat asthma patients.

BRIEF DESCRIPTION OF THE DRAWINGS

Figure 8:
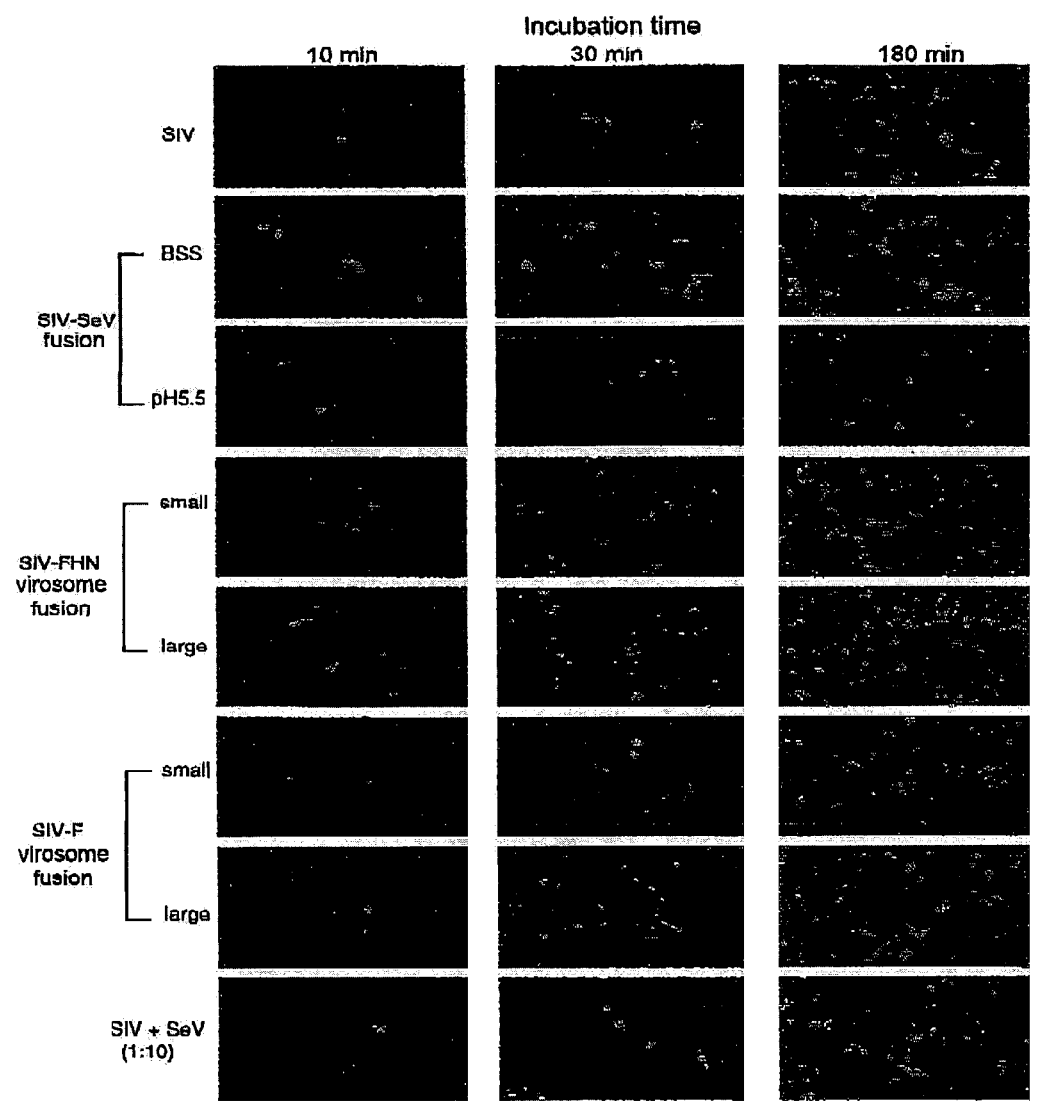

FIG. 8 depicts photographs showing a result obtained by the observations of infected cells (GFP-expressing cells). SIVs fused with inactivated Sendai virus (SeV), FHN virosome, and F virosome (respectively, corresponding to SIV-SeV fusion, SIV-FHN virosome fusion, and SIV-F virosome fusion in this Figure) were added to the culture supernatant of HeLa cells at MOI-10. The mixtures were incubated for 10, 30, and 180 minutes for infection, and then the culture media were changed with fresh ones. The cells were observed 48 hours after the infection. The SIV used had been pseudotyped by VSV-G. SIV in this Figure refers to a negative control which was not fused with Sendai virus envelope.

FIG. 14 shows the amino acid sequence (SEQ ID NO: 40) at the boundary between the SIV cytoplasmic domain and the HN protein transmembrane domain (standard font) in the protein encoded by the HN expression plasmid with a substitution of cytoplasmic domain.

FIG. 15 shows the amino acid sequence (SEQ ID NO: 41) at the boundary between the cytoplasmic domain (underlined) and the HN protein transmembrane domain (standard font) in the protein encoded by the HN expression plasmid with an addition of SIV cytoplasmic domain.

FIG. 16 shows the amino acid sequences (SEQ ID NOs: 42 to 44) at the boundary between the F protein transmembrane domain (italic) and F protein cytoplasmic domain (standard font) in the proteins encoded by the F expression plasmids with a deletion of cytoplasmic domain.

FIG. 17 shows the amino acid sequences (SEQ ID NOs: 45 to 47) at the boundaries between the F protein transmembrane domain (italic without underline), F protein cytoplasmic domain (standard font), and the 11 amino acids of SIV cytoplasmic domain ($SIV_{c11}$) (underline) in the proteins encoded by the F expression plasmids in which the F cytoplasmic domain has been replaced with the SIV cytoplasmic domain.

FIG. 19 depicts photographs showing gene transfer into BEAS-2B cells via the SeV F/HN pseudotype SIV vector.

BEST MODE FOR CARRYING OUT THE INVENTION

Figure 1:
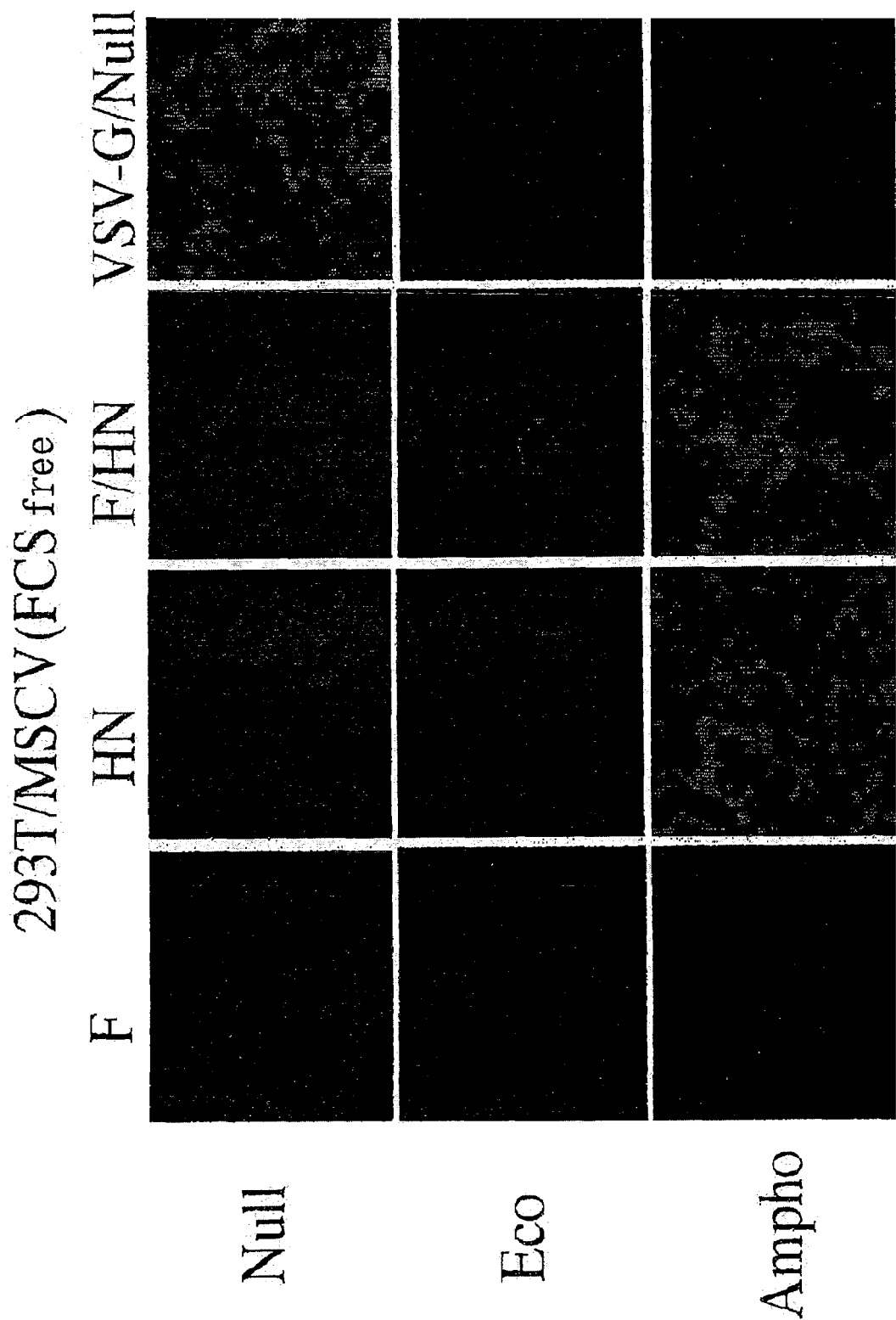
FIG. 1 depicts photographic patterns showing the results obtained with 293T cells infected with murine stem cell virus (MSCV) pseudotyped by F, HN, or F and HN proteins from Sendai virus. The virus packaging was achieved by using a gene transfer vector expressing EGFP (pMSCV EGFP). The labels in the above panels, "F", "HN", and "F/HN", correspond to the results obtained by the infection with the viruses produced by expressing F, HN, and F and HN proteins of Sendai virus in the packaging cell, respectively. In the column of "VSV-G/Null", the top panel depicts a positive control pseudotyped by VSV-G; the middle and bottom panels depict non-pseudotyped negative controls without expressing env proteins for pseudotyping, such as F, HN, and VSV-G. The labels at the right of the panels indicating "Eco" and "Ampho," correspond to the results obtained by using viruses prepared by expressing ecotropic env and amphotropic env in the packaging cells, respectively. The label "Null" indicates that retrovirus env was not expressed.

The present invention will be specifically described below using Examples; however, it is not to be construed as being limited thereto. All publications cited herein are incorporated herein by reference in their entireties.

EXAMPLE 1

Preparation of Retroviral Vectors Pseudotyped by Sendai Virus Envelope Protein

The genes for F, HN, and M proteins were obtained by digesting the full-length genome DNA of Sendai virus Z strain pSeV18$^+$b(+) (Hasan, M. K. et al., 1997, J. General Virology 78: 2813-2820), and inserted into pCAGGS (Niwa, H. et al., Gene: 108, 193-9, 1991) at the XhoI site, to prepare expression vectors for F, HN, and M proteins of Sendai virus (referred to as pCAGGS F, pCAGGS HN, and pCAGGS M, respectively).

The human fetal kidney-derived cell line, 293T cell (Proc. Natl. Acad. Sci. USA, vol.90, pp.8392-8396, 1993), which was used to produce retrovirus, was cultured in D-MEM (GibcoBRL) containing 10% inactivated fetal bovine serum. Culture was carried out in plastic plates (Sumitomo Bakelite). The vector transfection was carried out using LIPOFECTAMINE PLUS (GibcoBRL) according to the provided instruction. 293T cells were plated in a 6-well plastic plate (Sumitomo Bakelite) at a cell density of $1 \times 10^6$ cells/well, and incubated in a $CO_2$ incubator under 10% $CO_2$ gas at 37° C. for 48 hours. 30 minutes before transfection, the culture medium was changed with 800 μl/well of D-MEM (GibcoBRL) containing 1% bovine serum albumin (GibcoBRL), and then culture was continued.

The gene transfer vector used was a murine stem cell virus-based vector (MSCV) (CLONTECH) (R. G. Hawley et al., Proc. Natl. Acad. Sci. USA 93: 10297-10302 (1996); R. G. Hawley et al., Gene Thrapy 1: 136-138 (1994)) containing the EGFP gene at a reporter gene. Amounts of DNAs used in the transfection are as follows: 700 ng/well of the gene transfer vector and 300 ng/well of packaging vector (pCL-Eco, pCL-Ampho (MuMLV 4070A) (both were purchased from IMGENEX) (Naviaux, R. K. et al., J. Virol. 70: 5701-5705 (1996)); these were used in combination with 200 ng/well expression vector for Sendai virus envelope protein (pCAGGS F and pCAGGS HN) and 200 ng/well expression vector for Sendai virus M protein (pCAGGS M) (Table 2). DNA was dissolved in 100 μl of OptiMEM and then 6 μl of PLUS reagent (GibcoBRL) was added thereto. The mixture was stirred and allowed to stand still at room temperature for 15 minutes. 4 μl of LIPOFECTAMINE was diluted with 100 μl of OptiMEM, and then added To the mixture of DNA and PLUS reagent (GibcoBRL). The resulting mixture was stirred and allowed to stand still at room temperature for 15 minutes. The solution containing the complex of DNA and LIPOFECTAMINE prepared by the above procedure was added dropwise to 293T cells incubated in a 6-well plate. After being gently stirred, the mixture was incubated in a $CO_2$ incubator under 10% $CO_2$ gas at 37° C. for 3 hours. After culture, 1 ml/well of D-MEM (GibcoBRL) containing 1% bovine serum albumin (GibcoBRL) and 15 μg/ml trypsin (GibcoBRL) was added to the culture. The mixture was incubated in a $CO_2$ incubator under 10% $CO_2$ gas at 37° C. for 24 hours. Then, the culture supernatant was filtered with a filter with 0.45-μm diameter pores (DISMIC-25CS filter; ADVANTEC). The resulting solution was used as a vector solution.

EXAMPLE 2

The Effect of Sendai Virus Envelope Protein on Pseudotyping of Retrovirus Vector The retroviral vector pseudotyped by Sendai virus envelope protein was prepared by the above-mentioned method and its effect was assessed.

293T cells used as a target were plated in a 6-well plastic plate (Sumitomo Bakelite) at a cell density of $1 \times 10^6$ cells/well, and then incubated in a $CO_2$ incubator under 10% $CO_2$ gas at 37° C. for 48 hours. The introduction of the viral vector into the target cells was achieved by overlaying the solution that had been prepared by adding inactivated fetal bovine serum and polybrene (Sigma) at the final concentrations of 10% and 8 μg/ml, respectively, to a solution containing the viral vector. 48 hours after vector introduction, the target cells were fixed using PBS (Invitrogen) containing 2% formaldehyde and 0.2% glutaraldehyde at room temperature for 20 minutes, and then washed once with PBS (Invitrogen). Then, the cells were observed under a fluorescence invert microscope (DMIRB(SLR), Leica) to detect EGFP expression in target cells.

First, either or both F protein expression plasmid (pCAGGS F) and HN protein expression plasmid (pCAGGS HN) which are Sendai virus envelope proteins, were co-introduced with a retrovirus-based gene transfer vector (pMSCV EGFP) into 293T cells in the absence of packaging vector. The culture supernatant was collected and tested for the introduction of the EGFP gene or EGFP protein into 293T cells as target cells. Results obtained by infecting 293T cells with the vectors prepared by using in various combinations the 12 types starting from "((1))" in the lower half of Table 2 are shown in FIG. 1. As shown in the panel "Null" in FIG. 1, in the absence of packaging vector, neither gene nor protein was transferred, even when F protein and HN protein were expressed in human cells. Thus, the expression of F protein and HN protein alone was found to be insufficient to produce retroviral vectors capable of transferring genes and to introduce EGFP protein into target cells.

When packaging is carried out using the ecotropic envelope protein that is an envelope protein having no infectivity to human cells, gene transfer into human cells was not achieved with the vector pseudotyped by F protein or HN protein alone, as shown in the panel "Eco" in FIG. 1. On the other hand, the vector pseudotyped by co-expressing F protein and HN protein transferred the gene into human cells to which the original virus is not infectious. The result indicates that vectors derived from viruses other than Sendai virus can be pseudotyped by Sendai virus F protein and HN protein, and thus the host ranges for infection of vectors other than Sendai virus can be widened.

When packaging was carried out using the amphotropic envelope protein having infectivity to human cells, the efficiency of gene transfer improved by the vector pseudotyped either by expressing HN protein alone, or by co-expressing F protein and HN protein, as seen in the panel "Ampho" in FIG. 1. The result indicates that vectors derived from viruses other than Sendai virus can be pseudotyped by Sendai virus HN protein alone, and the efficiency of gene transfer mediated by a vector derived from a virus other than Sendai virus can be improved by pseudotyping the vector either with Sendai virus HN protein alone, or with Sendai virus F protein and HN protein.

In addition, since typically Sendai virus has high infectivity to cells containing mucus, such as epithelial cells of bronchial mucus membrane in the lung, other vectors pseudotyped either by HN protein alone, or by F protein and HN protein can be used for gene transfer into cells containing mucus.

EXAMPLE 3

Production of HN-Ampho Pseudotype Retroviral Vector and Comparison of the Efficiency of Gene Transfer into Human Bone Marrow Cells Including Hematopoietic Stem Cells between the Pseudotype Viral Vector and the Amphotropic Retroviral Vector 1. Culture of 293T Cells 293T cells were cultured in Dulbecco's modified Eagle medium (DMEM) containing 10% FCS and 800 µg/ml G418 according to the conventional method. Using a 10-cm plate, the cells diluted to $8 \times 10^6$ cells/plate the day before transfection, and then cultured in DMEM containing 10% FCS.

2. Transfection 5.6 µg of pMSCV EGFP, 2.4 µg of pCl-Ampho (IM-GENEX), and 1.6 µg of pCAGGS-HN were combined together, and 800 µl of OPTIMEM was added thereto. 48 µl of the Plus solution in a Lipofectamine Plus kit (GIBCOBRL) was further added to the mixture, and the resulting mixture was allowed to stand still for 15 minutes. In a separate tube, 800 µl of OPTIMEM and 32 µl of Lipofectamine solution combined together. The DNA mixture and Lipofectamine mixture were mixed and allowed to stand still for 15 minutes. The culture medium was removed and the transfection mixture was added dropwise all over to 293T cells in 500 µl of DMEM containing 1% BSA. The cells were incubated under 5% $CO_2$ gas at 37° C. A control transfection experiment was carried out using 5.6 µg of pMSCV EGFP and 4.0 µg of pcl-Ampho. Three hours after transfection, the culture medium was replaced with 10 ml of Iscove's modified DMEM (IMDM) containing 10% FCS. On the following day, the medium was again changed with IMDM containing 10% FCS, and the culture was further continued for 24 hours.

3. Collecion of Virus Solution

The cell culture supernatant was collected 48 hours after transfection. The supernatant was filtered with a 0.45-µm filter and then stored at −80° C.

4. Assay for Hemagglutinin Activity

Figure 2:
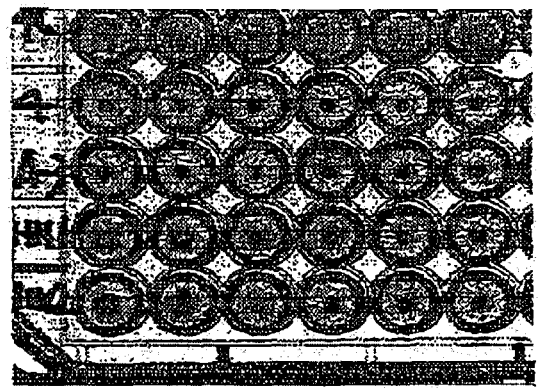
FIG. 2 depicts a photographic pattern showing results of HA assay of retroviruses having amphotropic env, which were pseudotyped by Sendai virus HN. The amounts of pMSCV EGFP, pCl-Ampho, and pCAGGS-HN used in viral production were also indicated (MSCV:AMPHO:HN in this Figure). While erythrocyte agglutination was not detected with the control retrovirus containing amphotropic env (Ampho-Retro in this Figure), the agglutination was observed with the retrovirus pseudotyped by Sendai virus HN (HN-Ampho-Retro in this Figure).

Retroviruses having amphotropic env pseudotyped by HN were prepared at various ratios of pMSCV EGFP, pCl-Ampho, and pCAGGS-HN in the same manner as described above. The viral hemagglutinin activity (erythrocyte agglutination activity; HA activity) was tested. The hemagglutinin activity of retrovirus having amphotropic env was also tested as a control. Assay for HA activity was carried out according to the conventional method. The result showed that the retrovirus pseudotyped by HN and amphotropic env had HA activity and the virus particles contained proteins exhibiting hemagglutinin activity (FIG. 2).

5. Gene Transfer into Human Bone Marrow CD34+ Cells

Human bone marrow CD34+ cell was purchased from BIO WHITTAKER. After thawing, along with $1 \times 10^5$/ml of the recombinant virus collected in Section 3, the cells were cultured in IMDM containing 50 ng/ml IL-6, 100 ng/ml TPO, 100 ng/ml Stem Cell Factor (GIBCO BRL), 100 ng/ml Flt-3 ligand (Research Diagnostics, Flanders, N.J.) (all the above were human recombinant proteins), and 10% FCS under 5% $CO_2$ at 37° C. overnight. 48, 51, 72, and 75 hours after the start of culture, the medium was changed with a freshly thawed virus solution, and 50 ng/ml IL-6, 100 ng/ml TPO, 100 ng/ml Stem Cell Factor, and 100 ng/ml Flt-3 ligand were added to the cells. 120 hours after the start of culture, the cells were collected.

6. Analysis by Flow Cytometry

Figure 3:
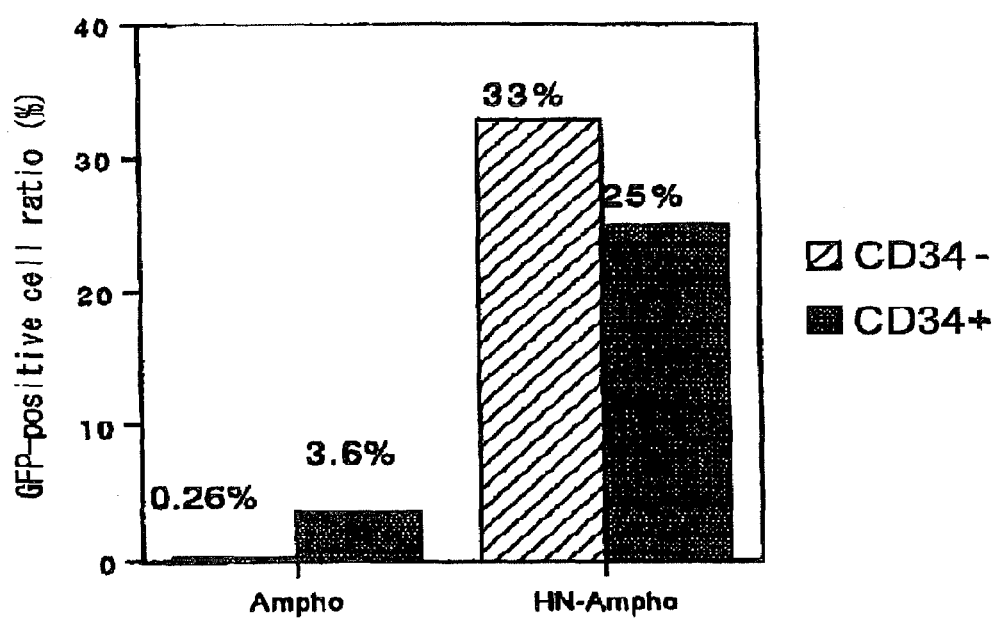
FIG. 3 is a diagram showing a result of assay which comprises infecting amphotropic env-containing MSCV pseudotyped by HN protein of Sendai virus (HN-ampho in this Figure) to human bone marrow cells and measuring the percentage of infected cells (GFP-expressing cells) by flow cytometry-based fractionation using CD34 as a marker. The "ampho" indicated in this Figure refers to a control which is not pseudotyped by HN protein. Each column indicates the ratio of GFP-positive cell against CD34-negative (CD34−) cell or CD34-positive (CD34+) cell.

The collected cells were stained with PE-labeled anti-human CD34 antibody (Becton Dickinson), and then analyzed by flow cytometry (EPICS ELITE, Coulter) using two fluorescence probes of GFP and PE. According to the result, the proportions of GFP positive cells in CD34-negative cells (CD34−) and CD34-positive cells (CD34+) infected with the amphotropic retroviral vector (ampho) containing the wild-type envelope were only 0.3% and 3.6%, respectively. However, the proportions of GFP positive cells in CD34-negative cells (CD34−) and CD34-positive cells (CD34+) infected with the HN-amphotropic retrovirus vector (HN-ampho) containing the pseudotype envelope were 33% and 25%, respectively, and thus the pseudotyping with HN protein was found to significantly increase the efficiency of gene transfer into human bone marrow cells including hematopoietic stem cells (FIG. 3).

EXAMPLE 4

Method for Preparing Pseudotype Virus Vectors

Retroviral vectors pseudotyped by various envelope proteins were prepared using the above-described pMSCV EGFP or pLZRNL expressing lacZ under the control of LTR derived from Moloney murine sarcoma virus (Yee, J.-K. et al., Methods In Cell Biology, vol. 43, pp.99-112 (1994); Xu, L. et al., Virology 171, 331-341 (1989)) as a gene transfer vector.

293T cells (human fetal kidney cell line) were cultured in Dulbecco's Modified Eagle Medium (DMEM)-High glucose (Gibco BRL) containing 10% inactivated calf serum (BIO WHITTAKER) under 10% $CO_2$ at 37° C. The 293T cells were plated in a 6-well plastic culture plate at a cell density of $5 \times 10^5$ cells/well, and then incubated under 10% $CO_2$ at 37° C. for 48 hours. The culture medium was changed with 800 µl/well of DMEM containing 1% bovine serum albumin. The cells were then used in transfection. In the combinations as indicated in Table 2 below, 700 ng of gene transfer vector (pMSCV EGFP or pLZRNL), 100 ng of VSV-G expression plasmid pVSV-G (derived from Indiana serotype strain) (Clontech), 200 ng each of Sendai virus HN, F, and M protein expression plasmids, pCAGGS-HN, pCAGGS-F, and pCAGGS-M, and 300 ng each of mouse retrovirus coat protein expression plasmids, pCL-Eco and pCL-Ampho (Imgenex) (Naviaux, R. K. et al., J. Virol. 70: 5701-5705 (1996)), were dissolved in 100 µl of Opti MEM in each well. Then, 6 µl of PLUS Reagent (Gibco BRL) was added to the well. The mixture was stirred, and then allowed to stand still at room temperature for 15 minutes. A solution obtained by diluting 4 µl of LIPOFECTAMINE Reagent (Gibco BRL) with 100 µl of Opti MEM was added to the mixture. The mixed solution was stirred, and then allowed to stand still at room temperature for another 15 minutes. The resulting mixture was added dropwise to the 293 T cells prepared above while being stirred gently. The cells were then incubated under 10% $CO_2$ at 37° C. for 3 hours. 1 ml of DMEM containing 1% bovine serum albumin and 15 µg/ml trypsin (Gibco BRL) was added to each well. The cells were incubated under 10% $CO_2$ at 37° C. for 48 hour, and then the culture supernatant was collected, and filtered with a filter with 0.45-µm diameter pores; the resulting solution was used as a vector solution.

TABLE 2

Figure 13:
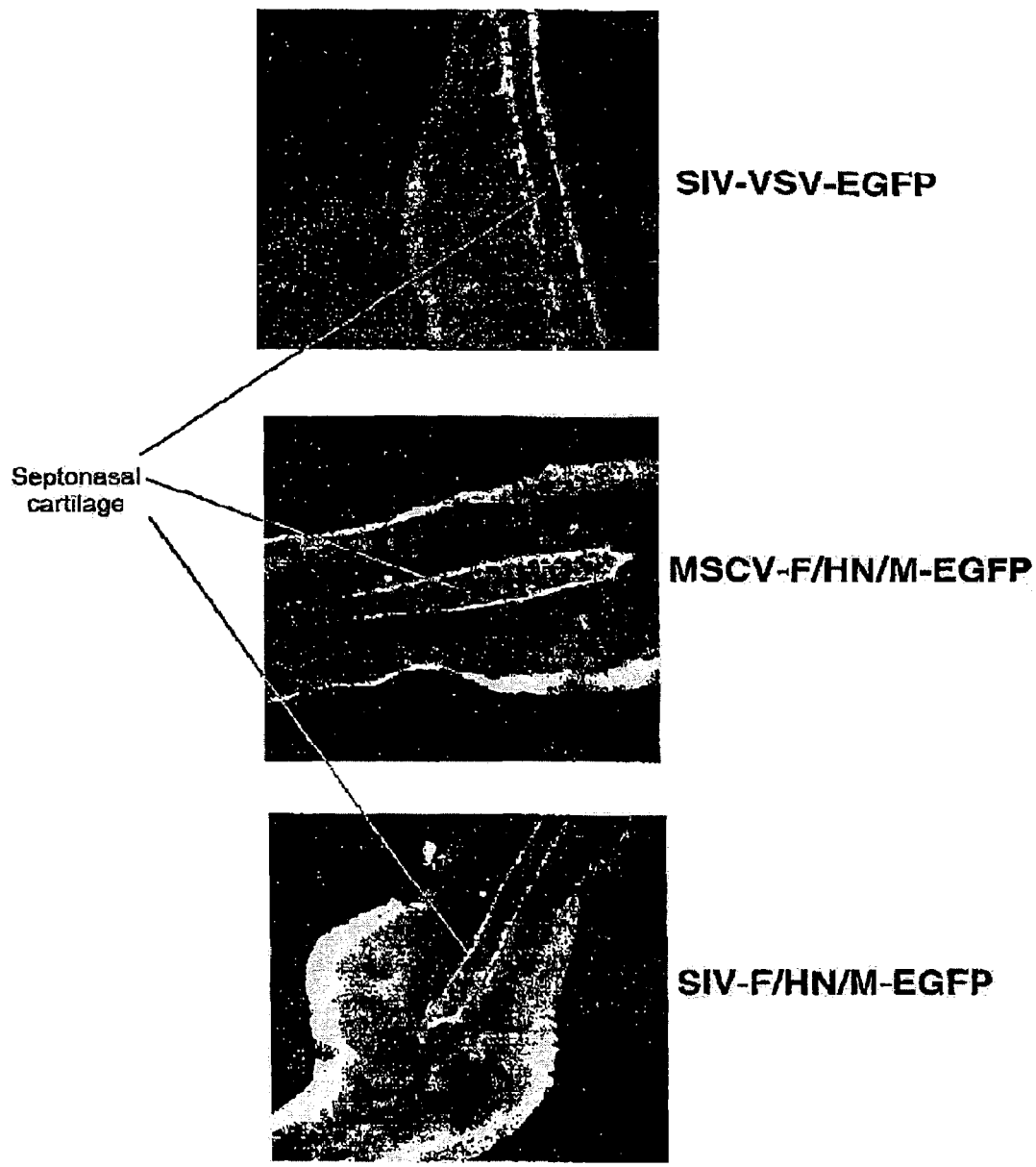
FIG. 13 depicts photographs showing a comparison of fluorescence intensities of GFP from the pseudotype retroviral vector in the sections of mouse nasal cavity. EGFP fluorescence images of SIV pseudotyped by VSV-G (SIV-VSV-EGFP), MSCV containing amphotropic env pseudotyped by F, HN, and M (MSCV-F/HN/M-EGFP), and VSV-G SIV pseudotyped by F, HN, and M (SIV-F/HN/M-EGFP) are shown. Relatively stronger signals are detected in MSCV-F/HN/M-EGF and SIV-F/HN/M-EGFP containing F, HN, and M proteins; particularly, the signal is higher in SIV-F/HN/M-EGFP.

| | env | | Gene transfer vector | |
|---|---|---|---|---|
| | Retro | SeV/VSV | in vitro | in vivo |
| ① | — | F/M | pMSCV-EGFP | pMSCV-EGFP |
| ② | | HN/M | or | (⑨: FIG. 13) |
| ③ | | F/HN/M | pLZRNL | |
| ④ | Eco | F/M | | |
| ⑤ | | HN/M | | |
| ⑥ | | F/HN/M | | |
| ⑦ | Ampho | F/M | | |
| ⑧ | | HN/M | | |
| ⑨ | | F/HN/M | | |
| ⑩ | Eco | — | | |
| ⑪ | Ampho | — | | |
| ⑫ | Eco | VSV-G | | |
| (①) | — | F | pMSCV-EGFP | ND |
| (②) | | HN | or | |
| (③) | | F/HN | pLZRNL | |
| (④) | Eco | F | (FIG. 1) | |
| (⑤) | | HN | | |
| (⑥) | | F/HN | | |
| (⑦) | Ampho | F | | |
| (⑧) | | HN | | |
| (⑨) | | F/HN | | |
| (⑩) | Eco | — | | |
| (⑪) | Ampho | — | | |
| (⑫) | Eco | VSV-G | | |

(Those indicated in the column "Env" in this Table are envelope proteins derived from retrovirus (Retro), Sendai virus (SeV), and vesicular stomatitis virus (VSV) used in the production of viruses. The gene transfer vector used were pMSCV EGFP or pLZRNL, which were utilized in in vitro and in vivo gene transfer, as shown in this Table. The vector indicated in the upper (9) in the Table, which had been prepared using pMSCV EGFP as a gene transfer vector, was used in the experiment in FIG. 13. The 12 types of vectors indicated in lower (1) to (12), which had been prepared using pLZRNL, were used in the experiment in FIG. 1.)

EXAMPLE 5

Construction of VSV-G Pseudotype Lentivirus Vectors

A nonpathogenic clone of African green monkey immunodeficiency virus, SIVagm TYO-1 strain, was used to construct vectors. Hereinafter, nucleotides are numbered while taking the transcription initiation site of viral RNA as +1. A SIVagm TYO-1-inserted plasmid used was pSA212 (J. Viol., vol.64, pp.307-312, 1990). Every ligation reaction was carried out using Ligation High (Toyobo) according to the attached instruction. All synthetic oligonucleotides used were synthesized and purified either with reverse-phase cartridges or by reverse-phase HPLC in the Biochemical Research Division of the Nippon Flour Mills Co., Ltd. via the Department of Custom DNA Synthesis, Greiner Japan. The sequence of the synthetic oligonucleotides are as follows:

```
1F(VTRF-BglII)                          (SEQ ID NO: 1)
5'-GCAGATCTCAACCAGGAGGCGAGGCTGCATTTTGGG-3'

1R(VTRR-EcoRI):                         (SEQ ID NO: 2)
5'-GCGAATTCTACTTACTGGTGCTGTAAAGGAGCCAAA-3'

2F(RREG964E)                            (SEQ ID NO: 3)
5'-ATCGGAATTCTTTTATTGTAAGATGGATTGGTTTTTAAAT-3'

2R(RRE-SA + BN):                        (SEQ ID NO: 4)
5'-CGGGATCCGCGGCCGCGGATATGGATCTGTGGAGATAG
AGGAACATAT-3'

3F(SDFXhoSpe):                          (SEQ ID NO: 5)
5'-TCGAGACTAGTGACTTGGTGAGTAGGCTT-3'

3R(SDR-SaI):                            (SEQ ID NO: 6)
5'-TCGAAAGCCTACTCACCAAGTCACTACTC-3'

4F:                                     (SEQ ID NO: 7)
5'-AATTTCTCGAGCGGCCGCA-3'

4R:                                     (SEQ ID NO: 8)
5'-AATTTGCGGCCGCTCGAGA-3'

5-1F(5LTRU3FKpn):                       (SEQ ID NO: 9)
5'-GCGGTACCTGGATGGGATTTATTACTCCGATAGGA-3'

5-1R(GAGR-2Eco):                        (SEQ ID NO: 10)
5'-GCGAATTCGATAGGGCTTGAAACATGGGTACTATTTCTGC-3'

5-2F(RREF-EcoRI):                       (SEQ ID NO: 11)
5'-GCGAATTCCCGTTTGTGCTAGGGTTCTTAGGCTTCT-3'

5-2R(RRESA + Rsac):                     (SEQ ID NO: 12)
5'-TCCCCGCGGATATGGATCTGTGGAGATAGAGGAACATATC-3'

5-3F(3LTRF BS)                          (SEQ ID NO: 13)
5'-GCGCGGCCGCGGATCCGTCGACGCACTTTTTAAAAGAAAAGGGA-3'

5-3R(3LTRR-SacI):                       (SEQ ID NO: 14)
5'-GCGAGCTCTAATGCAGGCAAGTTTATTAGCTTTCTA-3'

6F(CMVFEcoSac):                         (SEQ ID NO: 15)
5'-GGAATTCCCGCGGTAGTTATTAATAGTAATCAATTACGGG-3'

6R(EGFPRstoNB):                         (SEQ ID NO: 16)
5'-CGGGATCCGCGGCCGCTTACTTGTACAGCTCGTCGATGCC-3'

9-1F(LTRF1 CMVU3F):                     (SEQ ID NO: 17)
5'-TATATAAGCAGAGCTCGCTGGCTTGTAACTCAGTCTCTTA-3'

9-2F(LTRF2 EF1aU3F):                    (SEQ ID NO: 18)
5'TATATAAGTGCAGTACGCTGGCTTGTAACTCAGTCTCTTA-3'

9-3F(CAGU3F):                           (SEQ ID NO: 19)
5'-TATAAAAGCGAAGCCGCTGGCTTGTAACTCAGTCTCTTA-3'

9R(GAGR-2Eco):                          (SEQ ID NO: 20)
5'-GCGAATTCGATAGGGCTTGAAACATGGGTAGTATTTCTGC-3'

10-1F:                                  (SEQ ID NO: 21)
5'-CGGGGTACCTCAATATTGGCCATTAGCCATATTATTCATT-3'

10-1R(U3CMVR):                          (SEQ ID NO: 22)
5'-AGTTACAAGCCAGCGAGCTCTGCTTATATAGACCTCCCAC-3'

11F(LTRF LdU3FSalSC):                   (SEQ ID NO: 23)
5'-ATGCGAGCTCGTCGACGCACTTTTTAAAAGAAAAGGGAGGACTGGAT
GGGATTTATTACTCCGATAGGACGCTGGCTTGTAACTCAGTCTCTTACTA
GG-3'

11R(3LTRR-SacI):                        (SEQ ID NO: 24)
5'-GCGAGCTCTAATGCAGGCAAGTTTATTAGCTTTCTA-3'
```

<Preparation of DNA Fragments by PCR>

All PCR experiment& were carried out using a PCR Supermix High Fidelity (Gibco BRL). A pair of synthetic oligonucleotides as primers were added at a final concentration of 1 nmol/ml to 90 μl of reaction solution containing 1 μg of template DNA, and then the total volume was adjusted to 100 μl with distilled water. The reaction was carried out in a GeneAmp PCR System 9600 (Perkin Elmer). The PCR profile used was as follows: pre-incubation at 94° C. for 1 minute, 10 cycles of denaturation at 94° C. for 30 seconds, annealing at 55° C. for 30 seconds, and extension at 68° C. for 90 seconds, followed by incubation at 68° C. for 5 minutes. After reaction, samples were purified using Wizard DNA clean-up System (Promega), both ends of the PCR products were treated with appropriate restriction enzymes, and fractionated in a 1% low-melting temperature agarose gel (SeaPlaque GTG agarose, FMC Biochem; dissolved in TAE buffer). DNA fragments of interest were excised from the gel and purified with Wizard PCR Preps DNA Purification System (Promega). The purified DNAs were used in ligation reaction.

<Construction of Vectors>

Figure 4:
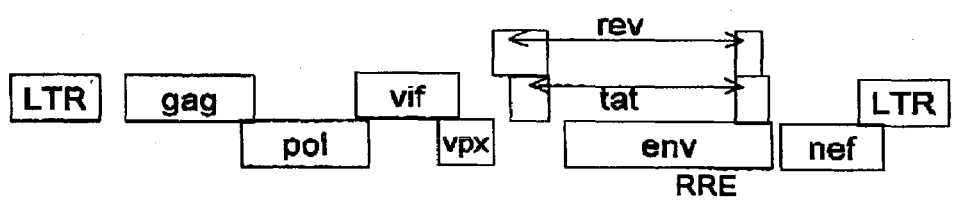
FIG. 4 depicts a schematic illustration of structures of: (a) the SIVagm-genome plasmid which was used as the backbone for the other constructs, (b) constructed packaging vector, (c) gene transfer vector, and (d) VSV-G-supplying vector.
Figure 4:
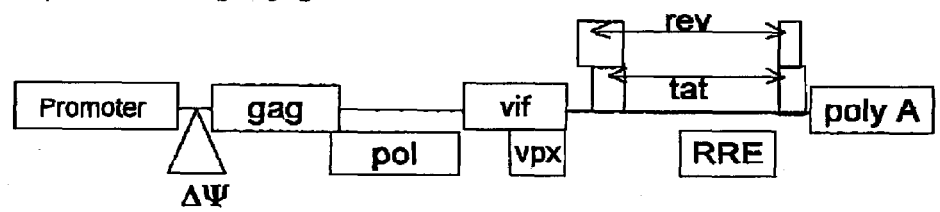
Figure 4:
Figure 4:

Plasmids that provide backbone structures for vectors were constructed (FIG. 4). Namely, these plasmid were "packaging vector" providing proteins essential for the formation of vector particles in trans, "gene transfer vector" providing mRNA to be packaged into the vector and delivering and introducing genes of interest into target cells, and the vector providing coat proteins participating in the formation of pseudotype vector particles.

Expression plasmids in each of which a sequence for gag, pol, tat, rev, vif, or vpr/x is located downstream of the promoter were constructed to provide proteins required for the formation of vector particles. Most parts of the packaging signal Ψ and env were removed to avoid the generation of wild-type virus particles. An SD sequence was inserted upstream or gag and RRE sequence was inserted downstream of the first exon of tat/rev to allow the expression of all genes in the packaging vector. In addition, the entire nef sequence was excluded because it was predicted to be nonessential for vector packaging (FIG. 4b).

The LTR sequences from the two ends of the genome, SD, Ψ, and RRE were inserted into the gene transfer vector providing RNA to be packaged into the vector. Further, a foreign promoter was substituted for the region of 5' LTR promoter in the gene transfer vector. In addition, a self inactivating vector (SIN vector), in which a portion of the 3' LTR sequence was removed to prevent the transcription of full-length vector mRNA in target cells, was prepared; this vector contains as inserts the β-galactosidase gene as a reporter gene and the CMV promoter for the expression of the reporter gene (FIG. 4c).

The vector used to provide VSV-G was the field-proven pVSV-G in pseudotyping retroviral and HIV vectors (FIG. 4d) (Burns, J. C. (1993) Proc. Natl. Acad. Sci. USA 90: 8033-8037).

More specific description is provided below.

<Construction of Packaging Vectors>

A DNA fragment corresponding to the region (5337 to 5770) containing vif and the first exon of tat/rev was prepared by PCR using a pair or primers 1F and 1R and pSA212 as a template. A site for the restriction enzyme EcoRI had been added to one of the PCR primers, and thus the prepared DNA fragment contained an EcoRI site at its 3' end. The PCR fragment was digested with BglII and EcoRI, and purified by using agarose gel electrophoresis and Wizard PCR Preps DNA Purification System (Promega). The DNA fragment prepared as described above and another DNA fragment encoding the gag/pol region (from XhoI site (356) to BglII site (5338)) were ligated into pBluescript KS+ (Stratagene) between the XhoI and EcoRI sites. Then, a Rev responsive element (RRE) and a DNA fragment corresponding to the region containing the second exon (6964 to 7993) of tat/rev were amplified by PCR. A NotI site was added to the 3' end by PCR using the pair of primers 2F and 2R and using pSA212 as a template by the same procedure as used to prepare the above-described PCR fragment. The resulting PCR fragment was double-digested with EcoRI and NotI, followed by purification. The fragment was inserted into pBluescript KS+ containing gag-tat/rev between the EcoRI and NotI sites.

A DNA fragment (3F and 3R) comprising a sequence for splicing donor (SD) site, which had synthesized to have an XhoI site and SalI site at 5' and 3' ends, respectively, was inserted at the XhoI site of the above-described pBluescript KS+ containing gag-RRE-tat/rev. The resulting plasmid was digested with XhoI and NotI. The fragment containing SD-gag-RRE-tat/rev was purified. A plasmid was prepared by inserting an XhoI/NotI linker (4F and 4R) into pCAGGS (Gene, vol.108, pp.193-200, 1991) at the EcoRI site, and then the above-mentioned SD-gag-RRE-tat/rev fragment was inserted at the XhoI-NotI site. The plasmid obtained by the method as described above was used as the packaging vector pCAGGS/SIVagm gag-tat/rev.

<Construction of Gene Transfer Vectors>

Using pSA212 as a template, PCR was carried out to amplify the SIVagm TYO1-derived 5' LTR region (8547 to 9053+1 to 982; containing KpnI site and EcoRI site at the 5' and 3' ends, respectively) using a pair of primers 5-1F and 5-1R; the 3' LTR region (8521 to 9170; containing NotI and BamHI sites at the 5' end and SacI site at the 3' end) using a pair of primers 5-3F and 5-3R; and the RRE sequence (7380 to 7993; containing EcoRI and SacII sites at the 5' and 3' ends, respectively) using a pair of primers 5-2F and 5-2R. The CMV promoter region (1 to 600; containing SacII and NotI sites at the 5' and 3' ends, respectively) derived from pEG-FPN2 (Clontech) was amplified using a pair of primers 6F and 6R. The DNA fragments were digested at their ends. After purification, the 5' LTR, RRE, CMV promoter, and 3' LTR were inserted in this order into pBluescript KS+ at the KpnI-SacI site by ligation. A NotI fragment containing the β-galactosidase gene derived from pCMV β (Clontech) was inserted as a reporter gene into the NotI site. The resulting plasmid was digested with KpnI and SacI to obtain a DNA fragment containing the region from the 5' LTR to the 3' LTR. The fragment was inserted into a control vector pGL3 at the KpnI-SacI site. The resulting plasmid was used as the gene transfer vector pGL3c/5' LTR.U3G2/RREc/s/CMV F β-gal/ WT 3' LTR.

Further, the CMV promoter region derived from pEGFPC2 (Clontech) and the region encoding EGFP (1 to 1330; containing a SacII site at the 5' end and NotI, BamHI sites, and translational stop codon at the 3' end) were amplified by PCR using a pair of primers 6F and 6R and using pEGFPC2 as a template. The four types of PCR fragments were digested with restriction enzymes KpnI and EcoRI, EcoRI and SacII, BamHI and SacI, and SacII and BamHI, respectively. After being purified, the fragments of 5' LTR, RRE, CMV promoter EGFP, and 3' LTR were inserted in this order into pBluescript KS+ between KpnI and SacI by ligation (pBS/5'LTR.U3G2/RREc/s/CMVFEGFP/WT3'LTR). The plasmid pBS/5'LTR.U3G2/RREc/s/CMVFEGFP/WT3'LTR was digested with KpnI and SacI to prepare a DNA fragment containing the region from the 5'LTR to the 3'LTR. The fragment was inserted into pGL3 (Promega) as a control vector at the KpnI-SacI site to construct a vector (pGL3C/5'LTR.U3G2/RREc/s/CMVFEGFP/WT3'LTR).

<Modification of 5' LTR>

A fragment containing gag region (9039 to 9170+1 to 982) downstream of the TATA box of 5' LTR was amplified by PCR using primers 9-1F, 2F, 3F and 9R and using pSA212 as a template. The CMV L promoter of cytomegalovirus (derived from pCI (Promega); nucleotides 1 to 721) was amplified by PCR using a pair of primers 10-1F and 10-1R. A fragment containing a region downstream of the TATA box of 5' LTR was combined with the fragment containing the promoter. A DNA fragment containing a chimeric promoter of the promoter and the 5' LTR was prepared by PCR using the mixture as a template and a primer (10-1F) placed on the 5' side of the promoter and another primer (9R) located on the 3' side of 5' LTR. The resulting DNA fragment was inserted into the gene transfer vector (pGL3C/5'LTR.U3G2/RREc/s/CMVF β-gal/WT3'LTR) at the KpnI-EcoRI site to prepare pGL3C/CMVL.U3G2/RREc/s/CMVF β-gal/WT3'LTR. Similarly, the DNA fragment obtained by the PCR experiment described above was also inserted into the vector pGL3C/5'LTR.U3G2/RREc/s/CMVFEGFP/WT3'LTR at the KpnI-EcoRI site to prepare pGL3C/CMVL.U3G2/RREc/s/CMVFEGFP/WT3'LTR.

<Preparation of 3' LTR-modified SIN Vector (Self Inactivating Vector)>

A DNA fragment containing the 27 bp at the 5' end, 15 bp at the 3' end, and R region from the U3 region of 3' LTR was amplified by PCR using a pair or primers 11F and 11R and using pSA212 as a template. This fragment was inserted into the SalI-SacI site of the gene transfer vector pGL3C/CMVL.U3G2/RREc/s/CMVF β-gal/WT3'LTR, which had been prepared to contain the chimeric promoter in the above Section, to prepare pGL3C/CMVL.U3G2/RREc/s/CMVF β-gal/3'LTRΔU3. Similarly, this fragment was also inserted into pGL3C/CMVL.U3G2/RREc/s/CMVFEGFP/WT3'LTR at the SalI-SacI site to prepare pGL3C/CMVL.U3G2/RREc/s/CMVFEGFP/3LTRΔU3.

<Preparation of Constructed Plasmid and Confirmation of the Structure>

The plasmid was transformed into DH5α (Toyobo) by the conventional method, and incubated in agar plates PCR was carried out using the emerging colonies as templates and primers capable of recognizing the DNA sequences of the inserted DNA fragment and a portion corresponding to the insertion site of the plasmid. PCR was carried out using PLATINUM PCR Supermix (Gibco BRL). The presence and the size of amplified products were confirmed by agarose gel electrophoresis to select clones containing desired inserts. Each clone was cultured in 10 ml of LB culture medium, and then the plasmid was purified with a QIAprep miniprep Kit (QIAGEN). The purified plasmids were treated with restriction enzymes to digest both ends of the inserted DNA fragments and electrophoresed in an agarose gel to confirm the size of the DNA fragments. Clones where the plasmids confirmed to contain an insert fragment of expected size were cultured in 100 ml of LB culture medium. The plasmids were purified with a QIAGEN Plasmid Maxi Kit (QIAGEN). Plasmids in which a PCR amplified fragment had been inserted were purified from 3 or more clones and sequenced, and the determined sequences were compared with those of pSA212 to select clones containing no mutation.

<Collection or Vectors>

293T cells were plated in a 6-well plastic culture plate at a cell density of $5\times10^5$ cells/well, and incubated under 10% $CO_2$ at 37° C. for 48 hours. The culture medium was replaced with 800 μl/well of Opti MEM before transfection. After 300 ng of the above-mentioned gene transfer vector, 600 ng of the above-mentioned packaging vector, and 100 ng of the expression plasmid pVSV-G for VSV-G (Clontech) were dissolved in 100 μl of Opti MEM in each well, 6 μl of PLUS Reagent (Gibco BRL) was added thereto. The mixture was stirred, and then allowed to stand still at room temperature for 15 minutes. 100 μl of Opti MEM containing 4 μl of LIPOFECTAMINE reagent (Gibco BRL) was added to the mixture. The resulting mixture was stirred and allowed to stand still at room temperature for 15 minutes. The mixture was added dropwise to the above-mentioned 293 T cells. The treated cells were stirred gently and incubated under 10% $CO_2$ at 37° C. for 3 hours. 1 ml of D-MEM containing 20% inactivated bovine serum was added to each well, and the plate was incubated under 10% $CO_2$ at 37° C. for 12 hours. After the culture medium was changed with 2 ml/well of D-MEM containing 10% inactivated bovine serum, the plate was incubated for 24 hours. Then, the culture supernatant was collected, and filtered with a filter with 0.45-μm diameter pores. The filtered supernatant was used in the subsequent experiments.

<SIVagm Vector-mediated Gene Transfer>

293T cells were plated in a 6-well plastic culture plate at a cell density of $5\times10^5$ cells/well, and incubated under 10% $CO_2$ at 37° C. for 48 hours. The culture medium was removed, and 1 ml of the solution containing the vector solution to which polybrane (Sigma) had been added at a final concentration of 8 μg/ml was overlaid onto the cells. The cells were incubated under 10% $CO_2$ at 37° C. for 3 hours to achieve vector transfect. After three hours, 1 ml of the culture medium was added to the cells. On the following day, the culture medium was changed. Next day, when the vector used was the β-Gal expression vector, staining was carried out using X-gal as the substrate with a β-Gal Staining Kit (Invitrogen), and the expression of β-galactosidase in the target cells was observed under a light microscope. However, when the vector used was the EGFP expression vector, the expression was analyzed under a fluorescence microscope.

<Vector Titration>

Vector titration was carried out by calculating the number of cells into which a gene was introduced using 1 ml of the vector solution. 293T cells were plated in a 6-well plastic culture plate at a cell density of $1\times10^6$ cells/plate, and incubated for 48 hours. By the same procedure as described above, infection to the cells was carried out with 1 ml of the vector solution. X-gal staining was performed 48 hours after infection. The mean value for the number of cells containing the transferred gene in a visual field was determined from three different visual fields under a light microscope with 200-fold magnification, and multiplied by the coefficient 854.865 that had been determined based on the area of the visual field and the area of the plate to determine the titer. The unit of titer was defined as Transducing Unit (T.U.)/ml. In addition, p27 protein in the vector solution was quantified using an SIV core antigen EIA kit (Coulter).

<Evaluation of Vectors>

It was predicted that the enhancement of the activity of 5' promoter in the gene transfer vector resulted in increased levels of RNA transcription and, which improved packaging efficiency and therefore increased vector titer. Thus, vectors where the 5' promoter had been replaced were evaluated based on the efficiency of gene transfer into 293T cells. The gene transfer was carried out by the same procedure as described above, and the expression of β-galactosidase was visualized by X-gal staining, which was followed by observation under a light microscope.

An SIN SIV vector was prepared based on an SIN gene transfer vector whose 3' LTR promoter had been deleted. An SIV vector was also prepared based on a gene transfer vector containing the original wild-type 3' LTR. The efficiency of transfer into 293T cells was compared between the two types of vectors. The amount of p27 protein was also determined to compare the transfer efficiencies normalized with the protein amount. In addition, the achievement of EGFP gene transfer into cells-cycle arrested 293T cells by irradiation, and SH-SY5Y cells terminally differentiated by retinoic acid were confirmed by observations under a fluorescence microscope.

<Results Obtained by Gene Transfer into 293T Cells>

Figure 5:
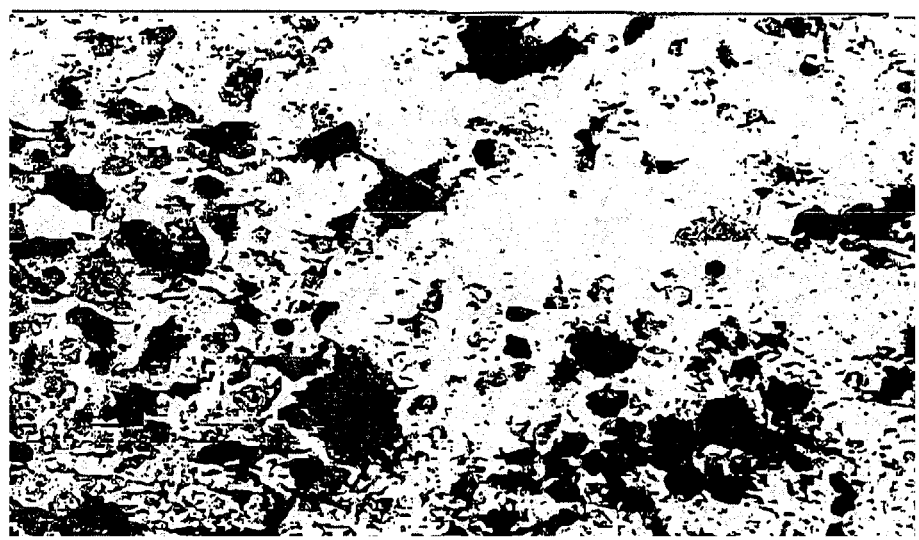
FIG. 5 depicts photographs showing a result of SIVagm vector-mediated introduction of the β-galactosidase gene into 293T cells. The top panel shows a result obtained by X-gal staining 48 hours after vector infection into 293T cells using the supernatant of cells transfected with the vector plasmid. The expression of β-galactosidase is detected in a number of cells. The bottom panel shows X-gal staining of untreated control cells.

The β-galactosidase gene was introduced into human fetal kidney-derived 293T cells using the SIVagm vector. The cells containing the transferred gene were stained using X-gal as the substrate. As FIG. 5 shows, cells stained blue were detected, which indicates that the β-galactosidase gene was expressed in the cells. According to the experimental result, the efficiency of gene transfer was 0.5 to $1\times10^5$ T.U. with 1 ml of vector solution. The amount of p27 in the vector solution was 0.5 to 1 µg/ml, and the transfer efficiency per 100 ng of p27 was $10^5$ T.U.

<Assessment for the Performance of SIN Vector>

The transfer efficiency of the SIN vector was compared with that of a conventional vector containing wild-type 3' LTR prepared under the same conditions. While the titer of conventional vector was 2.4 to 2.8 T.U./ml, that of SIN vector was 2.5 to 2.9 T.U./ml; thus, the transfer efficiency of SIN vector was 105% when the efficiency of conventional vector was taken as 100%. Further, the relationship between the transfer efficiency and the amount of p27 protein was determined by measuring the efficiency of transfer into 293T cells and assaying the amount of p27 by EIA; the efficiency of STN vector was $7\times10^5$ T.U. per 100 ng of p27.

The EGFP gene was transferred by the SIN vector into cells-cycle arrested 293T cells and terminally differentiated SH-SY5Y cells. 293T cells were cultured in DMEM containing 10% FCS under 10% $CO_2$ at 37° C. The cells cycle was arrested in G1-S phase by adding aphidicolin (Calbiochem-Novabiochem International, Inc.) at a final concentration of 20 µg/ml (Huberman, J. A. et al., Cell: Vol.23, 647-648, 1981; Byrnes, J. J., Mol. Cell. Biochem.: April, 62(1),:13-24. 1984). G2-M phase arrest was achieved by irradiating 4000-rad X ray to $2\times10^7$ cells (Kastan, M. B. et al., Cell: November 13, 71(4):587-97, 1992). 24 hours after the treatment for cell arrest, the cells were plated in a 6-well culture plate (SUMILON) coated with collagen type I at a cell density of $1\times10^6$/well. After 24 hours, gene transfer was carried out. Alternatively, human neuroblast cell line SH-SY5Y (Koshizawa, S. H. et al., Cancer Lett.: January 1, 111(1-2), 117-25, 1997) was cultured in RPMI1640 containing 10% inactivated calf serum under 5% $CO_2$ at 37° C., and all-trans retinoic acid (SIGMA) was added to the culture medium at a final concentration of 5 µM. Cells were incubated for 7 days, and then gene transfer was carried out (Odelstad, L. et al., Brain Res.: Nov. 9, 224(1), 69-82, 1981).

Figure 6:
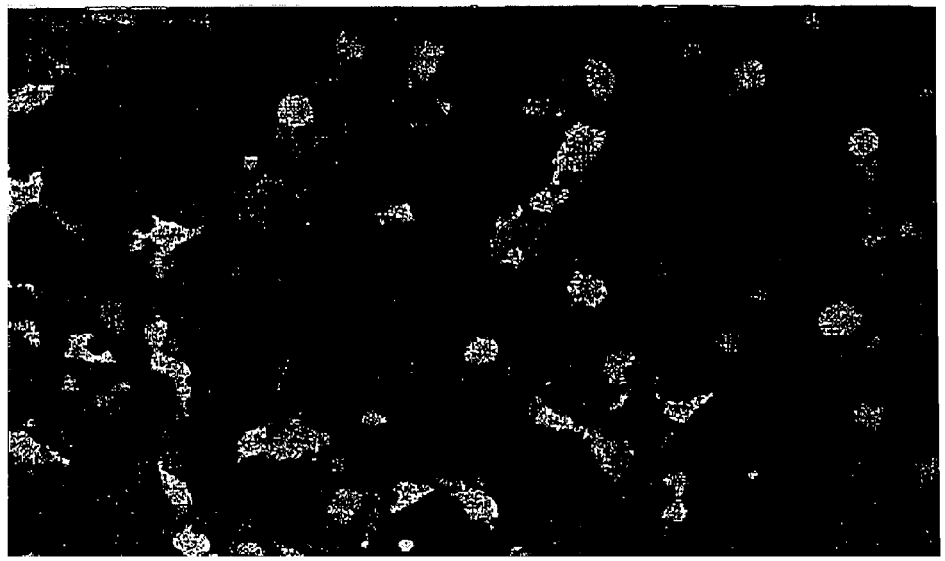
FIG. 6 depicts photographs obtained by introducing the EGFP gene into G2-M phase-arrested 293T cells and SH-SY5Y cells differentiated by retinoic acid, in which gene transfer was mediated by the SIVagm SIN vector, and observing the resulting expression using a fluorescent miroscope. The expression was confirmed under a fluorescence microscope. The top panel, 293T, magnification=×100; the bottom panel, SH-SY5Y, magnification−×200.
Figure 6:
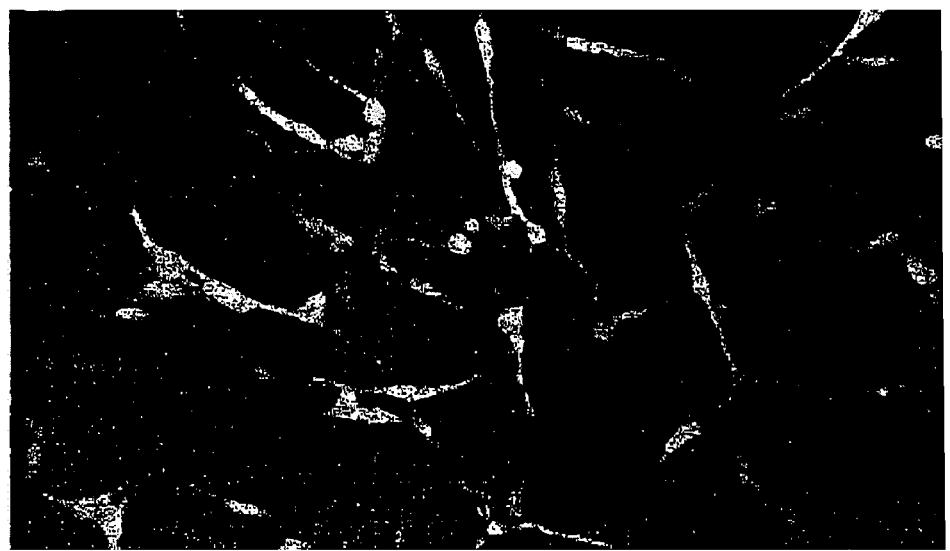

The top panel of FIG. 6 shows a pattern of EGFP expression in 293T cells observed with fluorescence microscopy. High efficiency expression or the gene was recognized. The bottom panel of FIG. 6 shows EGFP expression in SH-SY5Y. EGFP expression was found in cells having nurites which appeared to have differentiated into neurons.

The SIVagm vector prepared in this Example was confirmed to mediate gene transfer into culture cells highly efficiently. The probability of reconstitution of wild-type virus particles in vector packaging after co-transfection of the three types of independent plasmids is assumed to be very low. Furthermore, SIVagm TYO-1 itself, used as a base for the vector, has been confirmed to exhibit no pathogenicity in terms of both natural and experiment infection (Ohta, Y. et al., Int. J. Cancer: 41, 115-22, 1988; Miura, T. et al., J. Med. Primatol.: 18(3-4), 255-9, 1989; Honjo, S. et al., J. Med. Primatol. 19(1), 9-20, 1990). In addition, the vector can be highly safe because generally lentiviruses are highly species-specific and have only weak pathogenicity to animal species other than their original target species (Novembre, F. J. et al., J. Virol.: 71(5), 4086-91, 1997).

In this Example, the packaging signal sequence has been removed from the packaging vector construct, and thus the RNA encoding viral proteins is not packaged into particles. The binding of rev protein to RRE induces transfer of RNA into the cytoplasm and suppression of splicing, resulting in the expression of viral proteins and packaging of full-length RNA into virus particles. Therefore, the inserted RRE in both packaging vector and gene transfer vector can regulate mRNA splicing of the packaging vector, which thus can allow expression of all genes. Then, mRNA of the gene transfer vector can be transferred into the cytoplasm, and packaged into the vector particles. There are some cases where vif, vpr/x have been excluded from HIV-1 vectors (Dull, T. et al., J. Virol.: November, 72(11), 8463-71, 1998), and this suggests the possibility that proteins are not essential for packaging and functioning of vector particles. vpr has been believed to be a factor responsible for the infectivity to non-dividing cells (Heinzinger, N. K. et al., Proc. Natl. Acad. Sci. USA: Jul. 19, 91(15), 7311-5, 1994); a report describes that the type of cell, to which HIV-1 vector can transfer genes, varies depending on the presence of vpr (Kim, V. N. et al., J. Virol.: January, 72(1), 811-6, 1998). It has also been reported that nef, which was completely excluded form the packaging vector in the Examples described herein, can be a causative protein of the SIV-mediated immunodeficiency based on the evidence obtained by experiments with infection to monkey (von Gegerfelt, A. S. et al., J. Virol. 73, 6159-65, 1999; Kestler, H. W. 3d., Naidu, Y. N., Kodama, T., King, N. W., Daniel, M. D., Li, Y., Desrosiers, R. C. Use of infectious molecular clones of simian immunodeficiency virus for pathogenesis studies., J. Med. Primatol. 18(3-4): 305-9, 1989). The corresponding sequence has been removed completely from the SIVagm vector constructed in this Example; therefore, even if reconstituted virus particles containing viral genes derived from the packaging vector were formed, the risk of pathogenicity for such particles would be further decreased.

The lentivirus-based vector can transfer genes into cell-cycle arrested culture cells and neurons because the original lentivirus is infectious to nondividing cells (Naldini, L. et al., Science: 272 263-267, 1996; Sutton, R. E. et al. , J. Virol., 73(5), 3649-60, 1999). When such a vector has been pseudotyped by VSV-G, unlike the original SIV, the infectivity of the vector is not limited to the infection to CD4– and chemokine receptor-positive cells. The receptor of VSV-G is known to be phosphatidylserine, which in one of the phospholipids, whose molecules are present on the surface of various types of cells (Schlegel, R. et al., Cell, 32(2), 639-46, 1983). Thus, the SIVagm vector which has been pseudotyped by VSV-G has a considerably wider range of infectivity. It is predicted that when viruses that are pseudotyped by membrane proteins having hemagglutinin activity are prepared based on this vector, they are capable of transferring genes to almost all types of animal cells with a high degree of efficiency.

EXAMPLE 6

Preparation of Virosome

The seed of wild-type SeV (Z strain) was inoculated to fertile eggs (10-day eggs), and the eggs were cultured at 35.3° C. for three days. Then, chorio-allantoic fluid was collected from the eggs. After centrifugation at 4,000 rpm for 15 minutes, the supernatant was centrifuged at 10,000 rpm for one hour to precipitate virus particles. The pellet was resuspended in BSS, and overlaid on a solution with a sucrose density gradient (30%/50%), followed by centrifugation at 25,000 rpm for one hour. A band of virus particles formed at the boundary between 30% and 50% sucrose was collected, and then diluted with a large volume of BSS. Then, the sample was centrifuged at 9,000 rpm for one hour to precipitate virus particles. The resulting virus particles were resuspended in BSS and stored at −80° C. until used.

F-HN virosome and F virosome were prepared from the Sendai virus obtained according to the method as described in the reference (Bagai et al., 1993, Biochem. Biophys. Acta 1152, 15-25). Specifically, the Sendai virus was solubilized with a detergent, and then insoluble RNP was removed by centrifugation. The particles were reconstituted by removing the detergent from the solution where F and HN proteins, and lipids (envelope lipids) had been solubilized to prepare F-HN virosome. The preparation was carried out under the game conditions as used in Example 7 except that the concentration of Triton X-100 was 1% (v/v) before centrifugation. The Sendai virus was pretreated with DTT (dithiothreitol) to reduce HN protein, and solubilized with a detergent by the same procedure as described above. The resulting insoluble HN protein along with RNP was removed by centrifugation. The particles were reconstituted to prepare F virosome by removing the detergent from the solution by the same procedure as described above.

Figure 7:
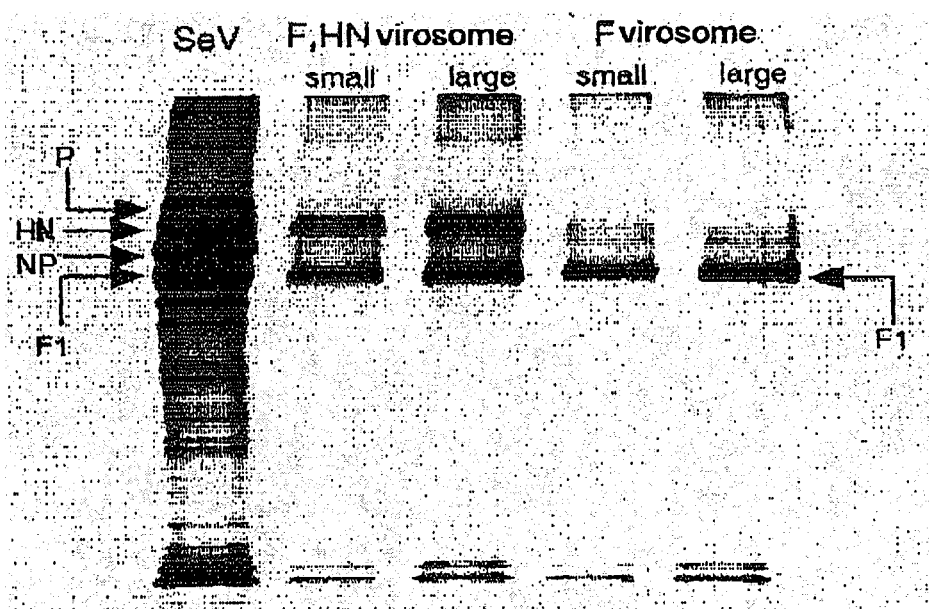
FIG. 7 is a photograph showing a result of Western blotting using FHN virosome and F virosome arranged in approximately the same particle diameter.

The resulting virosomes exhibited heterogeneous particle diameters. Therefore, the virosomes were separated into two fractions containing the particles of different size through centrifugation at 12,000 rpm for 10 minutes (small virosome: average particle diameter–140 nm; large virosome: average particle diameter=1.4 µm). The fractionated virosomes were assessed by SDS-PAGE. Both F protein and HN protein were detected in the F-HN virosome; F protein, in the F virosome. Thus, it was confirmed that the virosomes nearly desired had been obtained (FIG. 7).

The virosome prepared as described above or Sendai virus inactivated by UV irradiation was fused with EGFP-expressing SIV virus, which had been prepared and enriched by the method described in Example 7(3) under conditions at 37° C. for two hours with the composition indicated in the Table below. It has been reported that the efficiency of fusion between VSV-G and liposome is higher at weakly acidic pHs (Yamada, S. et al., 1986, Biochemistry, 25, 3703-3708). Therefore, the fusion was carried out at pH5.5 or neutral pH.

of infection, observation was made to detect GFP fluorescence (FIG. 8).

According to the result obtained, when SIV alone infected HeLa cells and the duration of contact was 30 minutes or shorter, the efficiency of infection was very low. It was found that the mixture of fusion of SIV and UV-inactivated Sendai virus had a tendency to infect faster than SIV alone. The infection efficiency at neutral pH was higher than that at pH 5.5. This may result from decreased influence of pH on SIV at a neutral.

The fusion with F-HN virosome also enhanced infection, thereby significantly improving infection efficiency. F virosome also improved the infection efficiently but to a lesser extent as compared with that of F-HN virosome. When SIV was simply co-infected with Sendai virus, the infection efficiency was only comparable to that of SIV alone.

These results demonstrate that fusion of SIV with Sendai virus or F-HN virosome enhances infectivity of SIV. Furthermore, it was suggested that HN protein of Sendai virus largely contributed to the enhancement of infection efficiency.

EXAMPLE 7

Preparation and Evaluation of SIV-SeV Fusion Vector (1) Preparation of Wild-type SeV The seed of wild-type SeV (Z strain) was inoculated to fertile eggs (10-day eggs), and the eggs were cultured at 35.3° C. for three days. Then, chorio-allantoic fluid was collected from the eggs. After centrifugation at 4,000 rpm for 15 minutes, the supernatant was centrifuged at 10,000 rpm for one hour to precipitate virus particles. The pellet was resuspended in BSS, and overlaid on a solution with a sucrose density gradient (30%/50%), followed by centrifugation at 25,000 rpm for one hour. A band of virus particles formed at the boundary between 30% and 50% sucrose was collected, and then diluted with a large volume of BSS. Then, the sample was centrifuged at 9,000 rpm for one hour to precipitate virus particles. The resulting virus particles were resuspended in BSS and stored at −80° C. for later use.

TABLE 3

| | SIV | | | SeV | | |
|---|---|---|---|---|---|---|
| Condition | Titer (TU/ml) | Buffer | Volume (µl) | Virus | Buffer | Volume (µl) |
| 1 | $1 \times 10^8$ | BSS | 50 | UV inactivated SeV $1 \times 10^9$ pfu/ml | BSS | 50 |
| 2 | $1 \times 10^6$ | pH5.5 Citric acid | 50 | UV inactivated SeV $1 \times 10^9$ pfu/ml | pH5.5 citric acid | 50 |
| 3 | $1 \times 10^8$ | BSS | 50 | FHN virosome (small) | BSS | 50 |
| 4 | $1 \times 10^8$ | BSS | 50 | FHN virosame (large) | BSS | 50 |
| 5 | $1 \times 10^8$ | BSS | 50 | F virosoma (small) | BSS | 50 |
| 6 | $1 \times 10^8$ | BSS | 50 | r virosame (large) | BSS | 50 |

The mixture prepared as described above was added to the culture supernatant of HeLa cell at MOI=10. A control experiment was carried out, where SIV was simply co-infected with Sendai virus. In this experiment, first, 5 minutes after SIV was added to culture medium, Sendai virus was added in 10-times volume of SIV. After the viruses were added to the culture medium, the mixture was incubated for infection for 10, 30, or 180 minutes. Then, the culture medium was changed with fresh one. 48 hours after the start (2) Reconstitution of Virosome from SeV Transmembrane Protein 1. FHN Virosome 0.2 ml of 20% (V/V) Triton X-100/BSS was added to 1.8 ml of SeV ($OD_{540}$-5, BSS), and the mixture was allowed to stand still at room temperature for 1 hour to solubilize SeV. In Example 6, the virosomes exhibited heterogeneous particle diameters. Thus, the concentration of Triton X-100 was adjusted to 2% (v/v) before centrifugation. The insoluble RNP was precipitated by centrifugation (at 100,000× g at 4° C. for 1 hour), and then the supernatant where F and HN proteins had been solubilized was collected. Bio-bead SM-2 (BIORAD) was added to the supernatant in three steps (0.5 g×twice, at room temperature for 1 hour; 1 g×once, at 4° C. for 15 hours plus incubation at room temperature 1 hour) to remove the detergent by adsorption, followed by the removal of the beads. Thus, approximately 1.5 ml of FHN virosome was obtained.

2. F Virosome 0.2 ml of 30 mM dithiothreitol/BSS was added to 2 ml of SeV ($OD_{540}$=5, BSS), and the mixture was incubated at 37° C. for two hours to irreversibly reduce HN protein. After dilution with BSS, virus particles were separated by centrifugation, and resuspended in 1.8 ml of BSS. 0.2 ml of 20% (V/V) Triton X-100/BSS was added to the virus suspension, and the mixture was allowed to stand still at room temperature for one hour to solubilize SeV. Then, insoluble RNP and reduced HN protein were removed by the same procedure as described above. The supernatant in which F protein had been solubilized was collected. Approximately 1.5 ml of F virosome was obtained by the same procedure as used to prepare FHN virosome.

3. HN Virosome 2 ml of 150 units/ml trypsin (Sigma)/BSS was added to 2 ml of SeV ($OD_{540}$=5, BSS), and the mixture was incubated at 37° C. for two hours to digest F protein. Then, 1 mg/ml trypsin-chymotrypsin inhibitor (Sigma)/BSS was added to the reaction mixture to stop the reaction. After dilution with BSS, virus particles were separated by centrifugation, and resuspended in 1.8 ml of BSS. Approximately 1.5 ml of HN virosome where the function of F protein had been inactivated was obtained by the same procedure as used to prepare FHN virosome.

Figure 9:
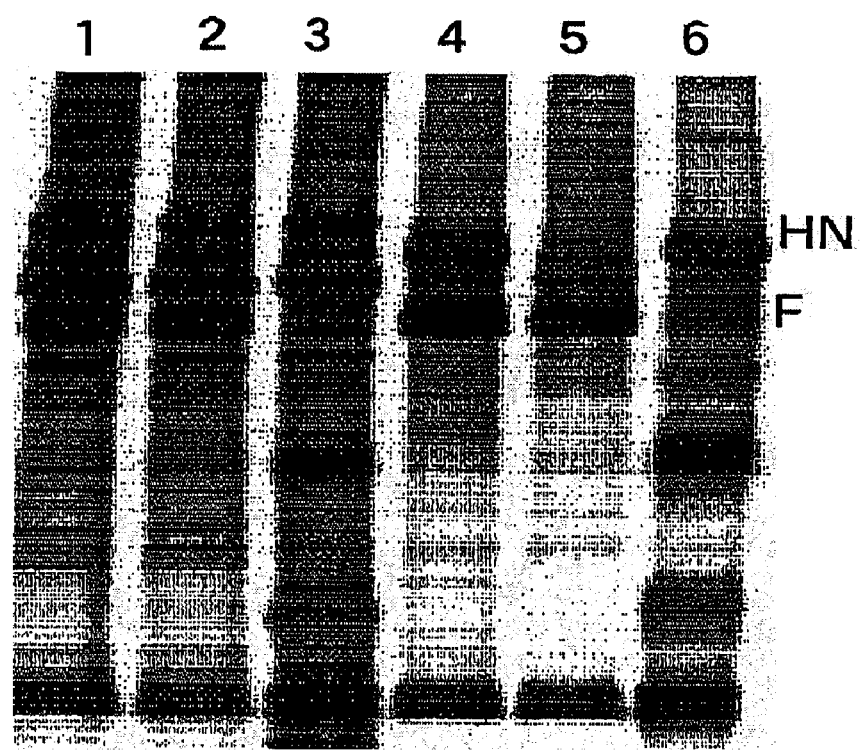
FIG. 9 depicts photographs showing a result obtained by electrophoresing samples of FHN virosome, F virosome, and HN virosome, followed by silver staining. Lane 1, SeV (intact); lane 2, DTT-treated SeV; lane 3, trypsin-treated SeV; lane 4, FHN virosome; lane 5, F virosome ; lane 6, HN virosome.

The characteristics of the three types of virosomes are shown in the Table below. The data of HA activity representing the function of F and HN proteins, hemolytic activity, and electrophoretic patterns showed that virosomes were required (FIG. 9).

TABLE 4

|  | FHN Virosome | F Virosome | HN Virosome |
| --- | --- | --- | --- |
| HA | + | − | + |
| Hemolytic Activity | + | − | − |
| $OD_{540}$ | 0.480 | 0.491 | 0.470 |
| Protein Concentration (mg/mL) | 0.96 | 0.57 | 0.78 |
| Average Particle Diameter (nm) | 143.5 | 168.9 | 133.0 |

150 μg of packaging vector, 300 μg of gene transfer vector, and 50 μg of VSV-G plasmid were dissolved in 75 ml of DMEM. 2 ml of Plus reagent (Life Technologies Oriental, Inc.) was added to the solution, and the resulting mixture was allowed to stand still at room temperature for 15 minutes. A suspension prepared by combining 3 ml of LipofectAMINE reagent (Life Technologies Oriental, Inc.) and 75 ml of DMEM was added to the mixture, and the resulting mixture was allowed to stand still at room temperature for 15 minutes to form DNA complex. 3 ml of the DNA complex solution was added dropwise to 293T cells (which were prepared in 50 dishes containing 10% FCS/DMEM at a cell density of 2.5× $10^6$ cells/150-mm dish 2 days before transfection). Transfection was carried out under 10% $CO_2$ at 37° C. for 3 hours. 10 ml of 10% FCS/DMEM was added to the cells, and then the incubation was further continued. After 48 hours, the culture supernatant was collected and filtered with a membrane filter with 0.45-μm diameter pores. The filtrate was centrifuged at 42,500× g for 1.5 hours to precipitate virus particles. The precipitates were combined together and resuspended in 15 ml of reverse transcription solution (100 μM dNTPs, 3 mM Spermine, 0.3 mM Spermidine, 10 mM $MgCl_2$/TBS). Revers transcription was carried out at 37° C. for two hours. Then, the virus was centrifuged (at 42,500× g for two hours), and the particles were resuspended in 500 μL of PBS (containing 5% FCS and 2 μg/mL polybrene) to obtain an SIV-LacZ-enriched solution. The titer of SIV-LacZ was approximately 5×$10^8$ T.U./mL (293T cells).

(4) Preparation of Fusion Vector

SIV-LacZ was diluted to 1×$10^8$ T.U./mL with BSS. An equal volume of a virosome/BSS solution was added to this solution. The mixture was allowed to stand still at 4° C. for 30 minutes for adsorption. Then, the fusion was carried out at 37° C. for two hours, and the reaction solution was diluted 10 times with ice-cold PBS (at a final SIV concentration of 5×$10^6$ T.U./mL). This SIV was used immediately in infection experiments.

(5) Infection Experiments 1 ml of 293T cells in 10% FCS/DMEM (hereinafter referred to as culture medium) was added to each well of 12-well plates at a cell density of 1×$10^5$ cells/well, and the cells were cultured under 10% $CO_2$ at 37° C. for 48 hours. Immediately before infection, the culture medium was reduced to 0.5 ml. A fusion vector consisting of SIV and the virosome was added to each well at a concentration of 5×$10^5$ T.U./ml (100 μl/well), and the mixture was incubated under 10% $CO_2$ at 37° C. for 10 minutes for infection. After the wells were washed twice with culture medium, 2 ml of culture medium was added to each well. Then, the plates were further incubated. After 48 hours, the cells were washed twice with PBS, and lysed with 0.25 ml of cell lysis buffer (PicaGene LC-β; Toyo Ink). The cell lyates were centrifuged at 12,000 rpm for 3 minutes, and the supernatant was diluted appropriately. The expression level of the LacZ gene was determined using Galacto-Light Plus™ (TROPIX, Inc.). The data was presented in relative LacZ activity per 1 μg of protein from the cells (RLU/μg protein), which was obtained as a mean±standard error from measurements in triplicate.

The expression level of LacZ was significantly greater with the FHN-virosome fusion than that with SIV alone (p<0.05). Unlike FHN-virosome, F-virosome did not result in increased expression levels of the gene. HN-virosome also had a tendency to elevate the level but to a lesser extent than FHN (FIG. 10).

In the above vectors, SIV VSV-G protein and virosome F protein are responsible for the fusion. The optimal pH for the fusion using VSV-G protein falls within a range of weakly acidic pH. On the other hand, F protein has been reported to participate in the fusion even at a neutral pH. In this Example, the fusion was achieved at a neutral pH, and thus F protein of SeV was assumed to be responsible for the majority of the fusion. It has been reported that fusion between SeV and liposome is achievable, as long as F protein is functionally active. Thus, when the efficiency of FHN virosome-based fusion is hypothesized to be comparable to that of the F virosome-based fusion, the increased level of gene expression by FHN virosome alone can be attributed to the substantial contribution of the additional HN. HN virosome also exhibited an effect at certain level; this suggests that VSV-G-based fusion occurred to some extent, which resulted in the integration of HN protein into SIV.

Figure 10:
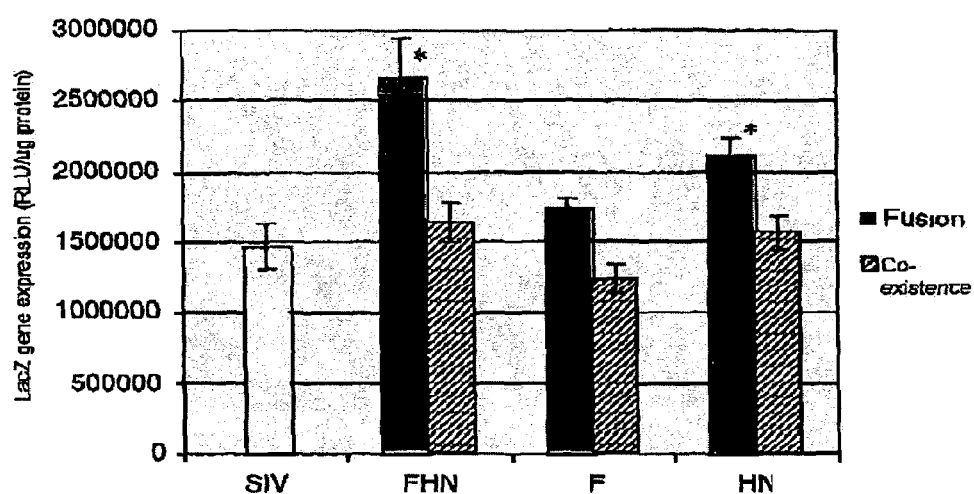
FIG. 10 depicts a diagram showing a result of assay for relative LacZ activity. A LacZ expression SIV vector (pseudotyped by VSV-G) and the same but further fused with virosome were introduced into 293T cells. Asterisk indicates that there was a significant difference for SIV in t-test (p<0.05).

On the other hand, the effect of simple co-infection of SIV and virosome was comparable to that of SIV alone (FIG. 10). These findings suggest that the fusion was established through incubation at 37° C. of the mixture containing the two, and thus the membrane proteins from SeV were integrated into the SIV envelope; HN protein mainly contributed to the improvement of the infection rate.

EXAMPLE 8

Preparation and Performance Analysis of HN Pseudotype Lentivirus Vector

1. Cell Culture 293T cells (human fetal kidney cell line) were cultured in Dulbecco's Modified Eagle Medium (DMEM)-High glucose (Gibco BRL) containing 10% inactivated calf serum (BIO WHITTAKER) under 10% $CO_2$ at 37° C.

2. Preparation of Vector 293T cells were plated in a 6-well plastic culture plate at a cell density of $5 \times 10^5$ cells/well, and then incubated under 10% $CO_2$ at 37° C. for 48 hours. The culture medium was changed with 800 µl/well of DMEM containing 1% bovine serum albumin. The cells were then used in transfection. In the combinations as indicated in Table 5 below, 1200 ng of gene transfer vector (pGL3C/CMVL.U3G2/RREc/s/CM-VFEGFP/3LTRΔU3 or pGL3C/CMVL.U3G2/RREc/s/CMVF β-gal/3LTRΔU3), 360 ng of packaging vector (pCAGGS/SIVagm gag-tat/rev), 120 ng of VSV-G expression plasmid pVSV-G(Clontech), 240 ng each of Sendai virus HN, F, and M protein expression plasmids, pCAGGS-HN, pCAGGS-F, and pCAGGS-M, were dissolved in 100 µl of Opti MEM in each well. Then, 6 µl of PLUS Reagent (Gibco BRL) was added to the well. The mixture was stirred, and then allowed to stand still at room temperature for 15 minutes. A solution obtained by diluting 4 µl of LIPOFECTAMINE Reagent (Gibco BRL) with 100 µl of Opti MEM was added to the mixture. The mixed solution was stirred, and then allowed to stand still at room temperature for another 15 minutes. The resulting mixture was added dropwise to the 293 T cells prepared above while being stirred gently. The cells were then incubated under 10% $CO_2$ at 37° C. for 3 hours. 1 ml of DMEM containing 1% bovine serum albumin and 15 µg/ml trypsin (Gibco BRL) was added to each well. After culturing under 10% $CO_2$ at 37° C. for 48 hour, the culture supernatant was collected and filtered with a filter with 0.45-µm diameter and the resulting solution was used as a vector solution.

TABLE 5

|      | ① | ② | ③ | ④ | ⑤ | ⑥ | ⑦ | ⑧ | ⑨ | ⑩ | ⑪ | ⑫ |
|------|---|---|---|---|---|---|---|---|---|---|---|---|
| PV   |   | ■ | ■ | ■ | ■ | ■ | ■ | ■ | ■ | ■ | ■ |   |
| GTV  |   | ■ | ■ | ■ | ■ | ■ | ■ | ■ | ■ | ■ | ■ |   |
| VSV-G|   |   |   |   |   |   | ■ | ■ | ■ | ■ | ■ |   |
| HN   |   |   | ■ |   |   | ■ |   | ■ |   |   | ■ |   |
| F    |   |   |   | ■ |   | ■ |   |   | ■ |   | ■ |   |
| M    |   |   |   |   | ■ | ■ |   |   |   | ■ | ■ |   |

(In this Table, plasmids added are indicated in black. "PV" indicates packaging vector pCAGGS/SIVagm gag-tat/rev; "GTV", gene transfer vector pGL3C/CMVL.U3G2/RREc/s/CMVFEGFP/3LTRΔU3 or pGL3C/CMVL.U3G2/RREc/s/CMVF β-gal/3LTRΔU3; "VSV-G", VSV-G expression plasmid pVSV-G; "HN", "F", and "M" indicate the Sendai virus HN protein-, F protein-, and M protein-expressing plasmids, pCAGGS-HN, pCAGGS-F, and pCAGGS-M, respectively.)

3. Large-scale Preparation and Enrichment of Vector 293T cells were plated in 15-cm plastic dishes at a cell density of $5 \times 10^6$ cells/dish, and cultured under 10% $CO_2$ at 37° C. for 48 hours. The culture medium was changed with 10 ml/dish of DMEM containing 1% bovine serum albumin. The cells were then used in transfection. In the combinations as indicated in Table 5 above, 8 µg of gene transfer vector, 2.4 µg of packaging vector, 0.8 µg of VSV-G expression plasmid pVSV-G (Clontech), 1.6 µg each of Sendai virus HN and F protein expression plasmids, pCAGGS-HN, pCAGGS-F, and pCAGGS-M, were dissolved in 1.5 ml of Opti MEM in each dish. Then, 40 µl of PLUS Reagent (Gibco BRL) was added to each dish. The mixture was stirred, and then allowed to stand still at room temperature for 15 minutes. A solution obtained by diluting 60 µl of LIPOFECTAMINE Reagent (Gibco BRL) with 1.5 ml of Opti MEM was added to the mixture. The mixed solution was stirred, and then allowed to stand still at room temperature for another 15 minutes. The mixture was added dropwise to the 293 T cells prepared above while being stirred gently. The cells were then incubated under 10% $CO_2$ at 37° C. for 3 hours. 10 ml of DMEM containing 1% bovine serum albumin and 15 µg/ml trypsin (Gibco BRL) was added to each well. After culture under 10% $CO_2$ at 37° C. for 48 hour, the culture supernatant was collected, and filtered with a filter with 0.45-µm diameter pores, followed by centrifugation at 42,490× g (TOMY SRX-201, TA21BH) at 4° C. for 90 minutes. The resulting pellet was dissolved in a 1/100 volume of a reverse transcription solution (TBS, 10 mM $MgCl_2$, 3 mM SPERMINE, 0.3 nM SUPERMIDINE, 100 mM dNTPs), and the solution was incubated at 37° C. for two hours. After reverse transcription reaction, the reaction was centrifuged at 42,490× g (TOMY SRX-201, TA21BH) at 4° C. for two hours, and the resulting pellet was dissolved in PBS (5% FCS, 2 µg/ml polybrene). The solution was stored at −80° C. until used.

When the three types of plasmids of packaging vector, gene transfer vector, and coat protein expression vector are co-transfected into cells, mRNA is transcribed from the gene transfer vector; the recognition of the Ψ sequence by a viral protein provided by the packaging vector allowed the RNA packaging into vector particles. Then, vector particles are finally formed via pseudotyping with the envelope protein provided by the coat protein vector. The prepared pseudotype virus vector was tested for the ability to achieve gene transfer into cells.

<Vector Titration and Detection of Cells Containing Transferred Gene>

Vector-mediated gene transfer into 293T cells was carried out by the above-mentioned method. The titer was determined based on the number of cells into which genes had been introduced using 1 ml of the vector solution. When a gene transfer vector encoding EGFP was used as a reporter gene, target cells were fixed with PBS (Invitrogen) containing 2% formaldehyde and 0.2% glutaraldehyde at room temperature for 20 minutes, and washed once with PBS; EGFP expression was evaluated based observations under a fluorescence invert microscope (DMIRB(SLR), Leica).

The three types of plasmids of packaging vector (pCAGGS/SIVagm gag-tat/rev), gene transfer vector (pGL3C/CMVL.U3G2/RREc/s/CMVFEGFP/3LTRΔU3), and Sendai virus-derived coat protein vector (pCAGGS-F, pCAGGS-HN, and pCAGGS-M) were co-transfected into cells in the combinations indicated in (2) to (5) of Table 5. In any of these combinations, the gene was not transferred into 293T cells. However, gene transfer was successfully achieved by the co-expression with VSV-G. These findings demonstrated that, when prepared with F and HN proteins alone, the pseudotype SIVagm vector did not mediate sufficiently high efficiency of gene transfer, but pseudotype viral vectors exhibiting higher infectivity could be produced by the help of coexisting viral envelope proteins, such as VSV-G, having infectivity to human cells.

The EGFP gene was introduced into 293T cells using the pseudotype SIVagm vector, and the vector titer was determined; the titer of prepared viral vector was 0.5 to $1 \times 10^5$ T.U. per 1 ml of the vector solution. The titer of viral vector enriched by centrifugation was as high as $1.0 \times 10^7$ T.U./ml. This demonstrated that the SIVagm vector pseudotyped by Sendai virus F and HN proteins could be enriched by centrifugation.

EXAMPLE 9

In vivo Administration of Pseudotype Viral Vector

The mucosal cells of tracheal epithelium into which genes are difficult to introduce with a conventional viral vector should be pre-treated to remove physical barriers at the time of introduction. Thus, when one intends to introduce genes into such cells by the method using the VSV-G pseudotype HIV vector, sufficient effects are ensured only after the cells are damaged with sulfur dioxide, etc. (L. G. Johnson et al., Gene Therapy: 7, 568-574, 2000). Thus, it was tested whether the SIVagm vector pseudotyped by Sendai virus F and HN proteins could transfer genes with high efficiency into mucosal cells of tracheal epithelium without damaging the cells.

6-week old C57BL/6 mice (male) were anesthetized by seboflurene inhalation, and the EGFP-expressing FHN pseudotype SIV vector (EGFP expression vector in (11) of Table 5) (referred to as SIV-F/HN/M-EGFP), which had been produced by the procedure described above, was administered to them intranasally. The tissues were embedded in OCT compound and sliced into frozen sections; the sections were observed under a fluorescence microscope (Zeiss).

Figure 11:
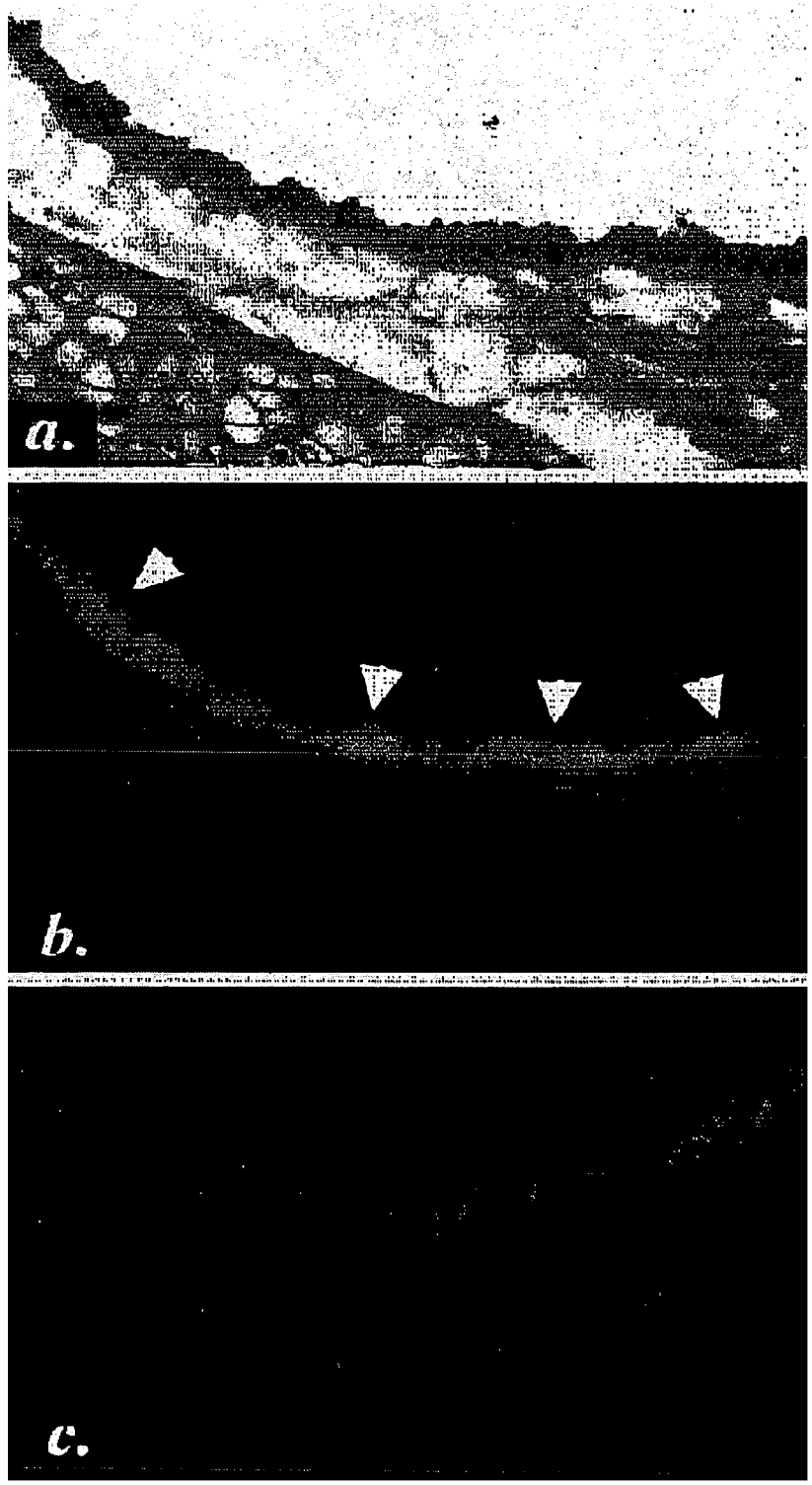
FIG. 11 depicts photographs showing frozen sections of trachea three days after intranasal administration of 100 μl of SIV-F/HN/M-EGFP $10^8$ T.U. The arrows in (b) indicate epithelial cells of the trachea, where fluorescence of EGFP can be detected, while only low-level background signals are observed in the sample of the untreated mouse shown in (c). The panel (a) shows a pattern of hematoxylin-eosin (H.E.) staining of a serial section.
Figure 12:
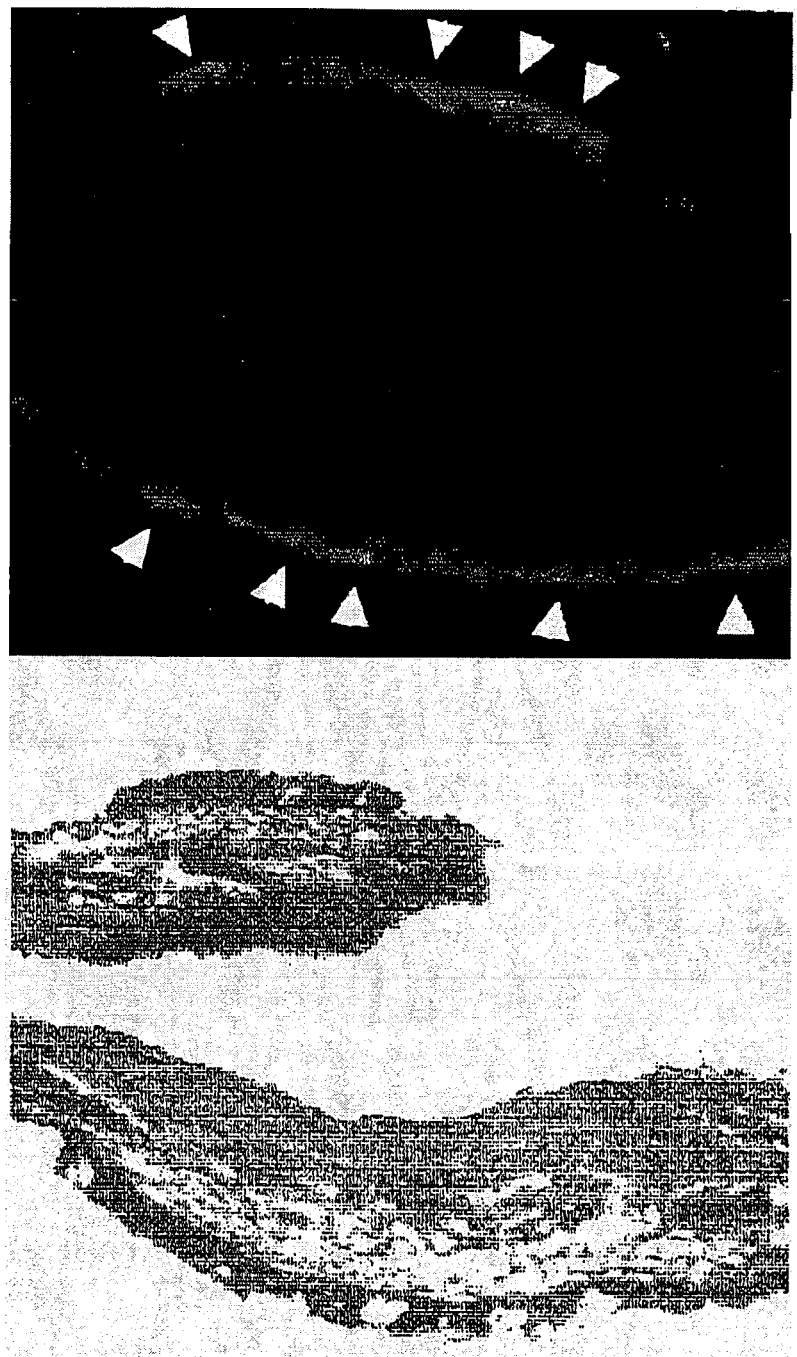
FIG. 12 depicts photographs (b) showing observations in septonasal mucus membrane of the same individuals as in FIG. 11. Arrow indicates pseudostratified ciliated epithelium that exhibits fluorescence of EGFP. (a) depicts photographs of H.E.-stained serial sections.

100 μl of SIV-F/HN/M-EGFP ($10^6$ T.U.) was administered intranasally, the trachea was observed after 3 days. EGFP fluorescence was detected in epithelial cells of the trachea (FIG. 11). In the same individuals, the mucosal epithelium also confirmed to express the gene, and the fluorescence was found to be localized in the pseudostratified ciliated epithelium in septonasal mucus membrane (FIG. 12).

EXAMPLE 10

Persistent Expression of Foreign Genes Mediated by in vivo Administration of Pseudotype Virus Vector A pseudotype retrovirus containing F and HN proteins was produced using a gene transfer vector expressing EGFP by the same procedure as described above. Specifically, pseudotype MSCV (MSCV-F/HN/M-EGFP) corresponding to (9) of Table 2 and pseudotype SIV (SIV-F/HN/M-EGFP) corresponding to (11) of Table 5 were produced. VSV-G pseudotype SIV (SIV-VSV-EGFP) corresponding to (1) of Table 5 was used as a control. The EGFP expression viral vectors were administered to mice intranasally, and sections from nasal mucous membrane tissues were prepared 90 days after the administration to observe EGFP expression.

According to the results obtained, every vector used resulted in EGFP expression; intense fluorescence signals for EGFP were detected in the cases of administration of MSCV-F/HN/M-EGFP and SIV-F/HN/M-EGFP containing F and HN proteins. In particular, administration of SIV-F/HN/M-EGFP vector gave a more intense fluorescent signal than that observed with the other vectors. Thus, the vector was confirmed to have the ability to transfer genes with high efficiency (FIG. 13).

EXAMPLE 11

Construction of Novel Expression Plasmid for Sendai Virus Envelope Proteins

[1] Construction of Expression Plasmid for Cytoplasmic Domain-Substituted HN Protein An HN expression plasmid was constructed, where the cytoplasmic domain of HN protein was replaced with the cytoplasmic domain of SIV envelope protein (FIG. 14). Three pairs of synthetic oligonucleotides (Xho+Xma/Xma−Xho, Xma+131/135−Xma, 132+Bam/Bam−136) were annealed, and then each was inserted into pBluescript KS+ (Stratagene) at the XhoI-BamHI site. A purified fragment containing the synthetic oligonucleotide, which had been obtained by digesting the above-described recombinant plasmid with XhoI and DraIII, or a purified fragment containing a 3' portion of HN protein, which had been obtained by digesting the HN protein expression plasmid pCAGGS-HN with DraIII and Bsu36I, was inserted into pCAGGS (Gene, vol.108, pp.193-200, 1991) at the XhoI-Bsu36I site. The plasmid obtained by the method described above was used as the expression plasmid for SIV cytoplasmic domain-substituted HN protein, pCAGGS-SIVct/HN.

[2] Construction of Expression Plasmid for SIV Cytoplasmic Domain-Added HN Protein An HN expression plasmid was constructed, where the cytoplasmic domain of SIV envelope protein was added to HN protein (FIG. 15). A region containing the cytoplasmic domain of SIV envelope protein and a portion of HN protein was amplified by PCR using primers FSIVhn and RhnSIV, and using as a template the above-mentioned expression plasmid for cytoplasmic domain-substituted HN protein. After the amplified fragment was digested with XhoI and AccI, the three pairs of synthetic oligonucleotides prepared in the above [1] were inserted into pBluescript KS+ (Stratagene) at the XhoI-AccI site to replace with the fragment containing the cytoplasmic domain of SIV envelope.

A purified fragment containing the synthetic oligonucleotide, which had been obtained by digesting the recombinant plasmid with XhoI and DraIII, or a fragment containing a 3' portion of HN protein, which had been obtained by digesting the HN protein expression plasmid pCAGGS-HN with DraIII and Bsu36I, was inserted into pCAGGS (Gene, vol.108, pp.193-200, 1991) at the XhoI-Bsu36I site. The plasmid obtained by the method described above was used as the expression plasmid for SIV cytoplasmic domain-added HN protein, pCAGGS-SIVct+HN.

[3] Construction of F Protein Expression Plasmid Lacking the Cytoplasmic Domain

F protein expression plasmids were constructed, each of which contained the first 27, 14, or 4 residues from the 5' end of the cytoplasmic domain amino acids of F protein and thus lacked 15, 28, or 38 amino acid residues, respectively (FIG. 16). Each of the fragments lacking 15, 28, and 38 amino acids, respectively, was amplified by PCR using the pairs of primers, XhFF and NotF1650, NotF1611 and NotF1581, and using as a template the plasmid pBluescript KS+/SmaI/F, in which the entire region for F protein had been inserted into pBluescript KS+ (Stratagene) at the SmaI site. The amplified fragments were digested with XhoI and NotI, and then each was inserted into the XhoI-NotI site of the plasmid that had been constructed from pCAGGS (Gene, vol.108, pp193-200, 1991) by inserting an XhoI/NotI linker into the EcoRI site to construct plasmids (15 amino acid deletion: pCAGGS-Fct27; 28 amino acid deletion: pCAGGS-Fct14; 38 amino acid deletion: pCAGGS-Fct4).

[4] Construction of Cytoplasmic Domain-lacking F Protein Expression Plasmid Containing SIV Cytoplasmic Domain Plasmids were constructed (FIG. 17) by adding the first 11 amino acids from 5' end of the SIV cytoplasmic domain (SIVct11) to cytoplasmic domain-lacking F protein expression plasmids (the numbers of amino acids in the cytoplasmic domain of F protein are the same as those in the plasmids prepared in [3]). Fragments corresponding to the above-described three types lacking the amino acids but containing the SIV cytoplasmic domain added were amplified by PCR using the pairs of primers XhFF and SA-F1650, and SA-F1611 and SA-F1581, and using as a template the plasmid pBluescript KS+/SmaI/F, in which the entire region for F protein had been inserted into pBluescript KS+ (Stratagene) at the SmaI site. The amplified fragments were digested with XhoI and NotI, and then each was inserted into the XhoI-NotI site of the plasmid that had been constructed from pCAGGS (Gene, vol.108, pp.193-200, 1991) by inserting an XhoI/NotI linker into the EcoRI site to construct plasmids (SIVct11 addition+15 amino acid deletion: pCAGGS-Fct27/SIVct11; SIVct11 addition+28 amino acid deletion: pCAGGS-Fct14/SIVct11; and SIVct11 addition+38 amino acid deletion: pCAGGS-Fct4/SIVct11).

EXAMPLE 12

Preparation and Performance Analysis of Sendai Virus Envelope-pseudotyped Lentivirus Vector <Cell Culture>

293T cells (human fetal kidney cell line) were cultured in Dulbecco's Modified Eagle Medium(DMEM)-High glucose (Gibco BRL) containing 10% inactivated calf serum (BIO WHITTAKER) under 10% $CO_2$ at 37° C.

BEAS-2B cells (human epithelial cell line derived from the trachea) were cultured in a mixture of Minimum Essential Medium (MEM) (Gibco BRL) and RPMI1640 (1:1 ratio) containing 10% inactivated calf serum (BIO WHITTAKER) under 5% $CO_2$ at 37° C.

<Preparation of Vector>

293T cells were plated in a 6-well plastic culture plate at a cell density of $5\times10^5$ cells/well, and then incubated under 10% $CO_2$ at 37° C. for 48 hours. The culture medium was changed with 800 μl/well of DMEM containing 1% bovine serum albumin. The cells were then used in transfection. In the combinations as indicated in Table 6 below, 1200 ng of gene transfer vector (pGL3C/CMVL.U3G2/RREc/s/CMVF EGFP/3LTRΔU3), 360 ng of packaging vector (pCAGGS/SIVagm gag-tat/rev), Sendai virus HN, F protein expression plasmid pCAGGS-SIVct/HN, pCAGGS-SIVct+HN, pCAGGS-Fct4, pCAGGS-Fct14, pCAGGS-Fct27, pCAGGS-Fct4/SIVct11, pCAGGS-Fct14/SIVct11, and pCAGGS-Fct27/SIVct11 were dissolved in 100 μl of Opti MEM (Gibco BRL) in each well. Then, 6 μl of PLUS Reagent (Gibco BRL) was added to the well. The mixture was stirred, and then allowed to stand still at room temperature for 15 minutes. A solution obtained by diluting 4 μl of LIPOFECTAMINE Reagent (Gibco BRL) with 100 μl of Opti MEM was added to the mixture. The mixed solution was stirred, and then allowed to stand still at room temperature for another 15 minutes. The resulting mixture was added dropwise to the 293 T cells prepared above while being stirred gently. The cells were then incubated under 10% $CO_2$ at 37° C. for 3 hours. 1 ml of DMEM containing 1% bovine serum albumin and 15 μg/ml trypsin (Gibco BRL) was added to each well. After culture under 10% $CO_2$ at 37° C. for 16 to 24 hours, the culture medium in each well was changed with 2 ml of DMEM containing 1% bovine serum albumin and 7.5 μg/ml trypsin (Gibco BRL). After subsequently culturing for 24 hours, culture supernatant was collected. This supernatant was then filtered with a filter having a 0.45 μm diameter and the resulting solution was used as a vector solution.

TABLE 6

| | | HN protein expression plasmid | | |
|---|---|---|---|---|
| | | pCAGGS-HN | pCAGGS-SIVct/HN | pCAGGS-SIVct + HN |
| F protein expression plasmid | pCAGGS-Fct4 | ○ | ○ | ○ |
| | pCAGGS-Fct14 | ○ | ○ | ○ |
| | pCAGGS-Fct27 | ○ | ○ | ○ |
| | PCAGGS-Fct4/SIVct11 | ○ | ○ | ○ |
| | PCAGGS-Fct14/SIVct11 | ○ | ○ | ○ |
| | PCAGGS-Fct27/SIVct11 | ○ | ○ | ○ |

<SIVagm Vector-mediated Gene Transfer>

293T cells and BEAS-2B cells as target cells were plated in 6-well plastic culture plates at a cell density of $1\times10^6$ cells/well, and incubated under 10% $CO_2$ at 37° C.; the incubation was carried out for 48 hours for 293T cells or for 24 hours for BEAS-2B cells. Then, the culture medium was removed from the culture plates, and 1 ml of a mixture obtained by adding polybrene (Sigma) to the vector solution at a final concentration of 8 μg/ml was overlaid on the cells. The plates were incubated at 37° C. for 3 hours to transfect the vector to the cells; the incubation was carried out under 10% $CO_2$ for 293T cells or under 5% $CO_2$ for BEAS-2B cells. After three hours, 1 ml of culture medium containing 20% inactivated calf serum (BIO WHITTAKER) was added to the cells, and the plates were incubated at 37° C. for 48 hours; the incubation was carried out under 10% $CO_2$ for 293T cells or under 5% $CO_2$ for BEAS-2B cells.

<Vector Titration>

The titer was determined based on the number of cells into which genes had been introduced using 1 ml of vector solution. Infection was carried out with 1 ml of the vector solution according to the method described above. 48 hours after infection, the cells were fixed with PBS (Invitrogen) containing 2% formaldehyde and 0.2% glutaraldehyde at room temperature for 20 minutes, and washed once with PBS. The mean value for the number of cells containing the transferred gene in a visual field was determined from three different visual fields under a fluorescence invert microscope (DMIRB (SLR), Leica) with 200-fold magnification, and multiplied by the coefficient 854.865 that had been determined based on the area of the visual field and the area of the plate to determine the titer. The unit of titer was defined as Transducing Unit (T.U.)/ml.

<Large-scale Preparation and Enrichment of Vector>

293T cells were plated in 15-cm plastic dishes at a cell density of $5\times10^6$ cells/dish, and incubated under 10% $CO_2$ at 37° C. for 48 hours. The culture medium was changed with 10 ml/dish of DMEM containing 1% bovine serum albumin. The cells were used in transfection. 8 μg of gene transfer vector (pGL3C/CMVL.U3G2/RREc/s/CMVF LacZ/3LTRÄU3), 2.4 µg of packaging vector (pCAGGS/SIVagm gag-tat/rev), 1.6 µg each of Sendai virus HN protein expression plasmid pCAGGS-SIVct+HN and F protein expression plasmid pCAGGS-Fct4 were dissolved in 1.5 ml of Opti MEM (Gibco BRL) in each dish. Then, 40 µl of PLUS Reagent (Gibco BRL) was added to the well. The mixture was stirred, and then allowed to stand still at room temperature for 15 minutes. A solution obtained by diluting 60 µl of LIPOFECTAMINE (Gibco BRL) with 1.5 ml of Opti MEM was added to the mixture. The mixed solution was stirred, and then allowed to stand still at room temperature for another 15 minutes. The resulting mixture was added dropwise to the 293 T cells prepared above while being stirred gently. The cells were then incubated under 10% $CO_2$ at 37° C. for 3 hours. 10 ml of DMEM containing 1% bovine serum albumin and 15 µg/ml trypsin (Gibco BRL) was added to each well. After culture under 10% $CO_2$ at 37° C. for 16 to 24 hours, the culture medium in each dish was changed with 20 ml of DMEM containing 1% bovine serum albumin and 7.5 µg/ml trypsin (Gibco BRL). After subsequently culturing for 24 hours, culture supernatant was collected. This supernatant was then filtered with a filter having a 0.45-µm diameter. Then, the filtrate was centrifuged at 16,000× g (Beckman J-25I, JA-18) at 4° C. for one hour. The pellet was dissolved in PBS (containing 5% FCS and 2 µg/ml polybrene). The resulting solution was stored at −80° C.

<Results>

Figure 18:
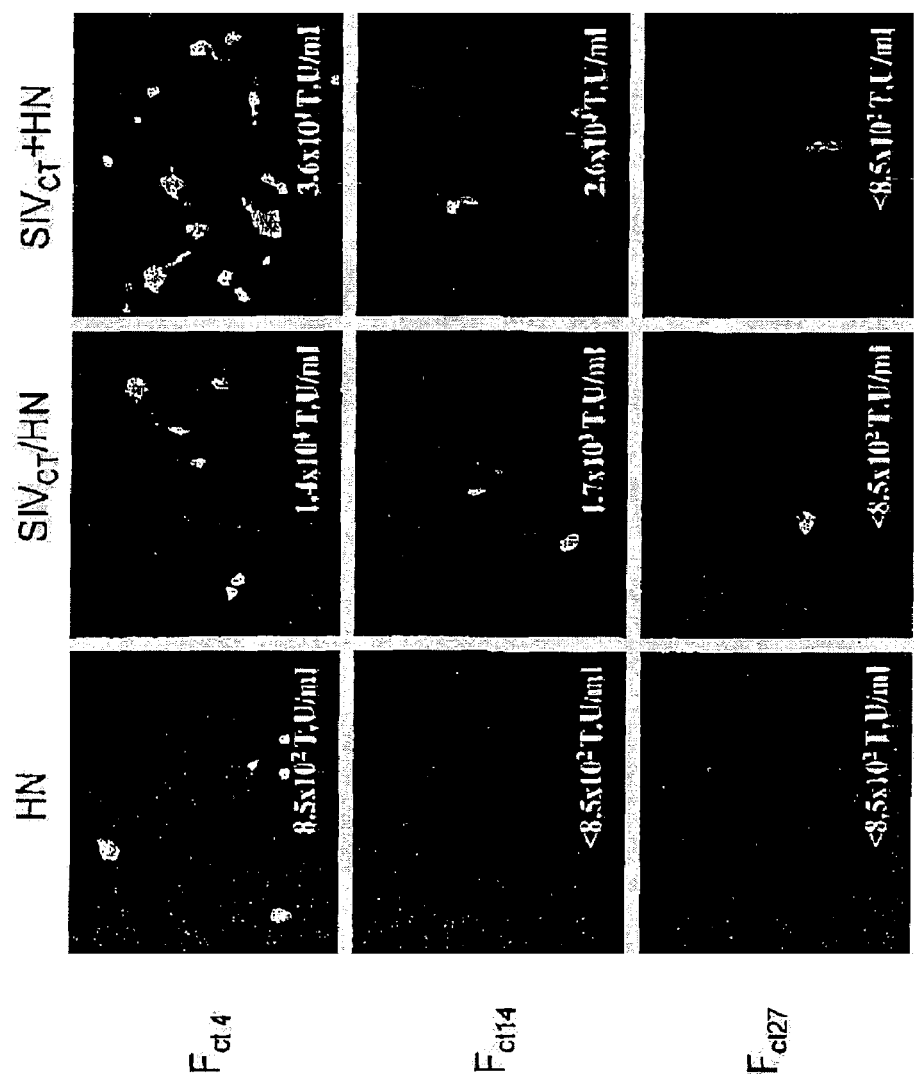
FIG. 18 depicts photographs showing gene transfer into 293T cells via the SeV F/HN pseudotype SIV vector.
Figure 19:
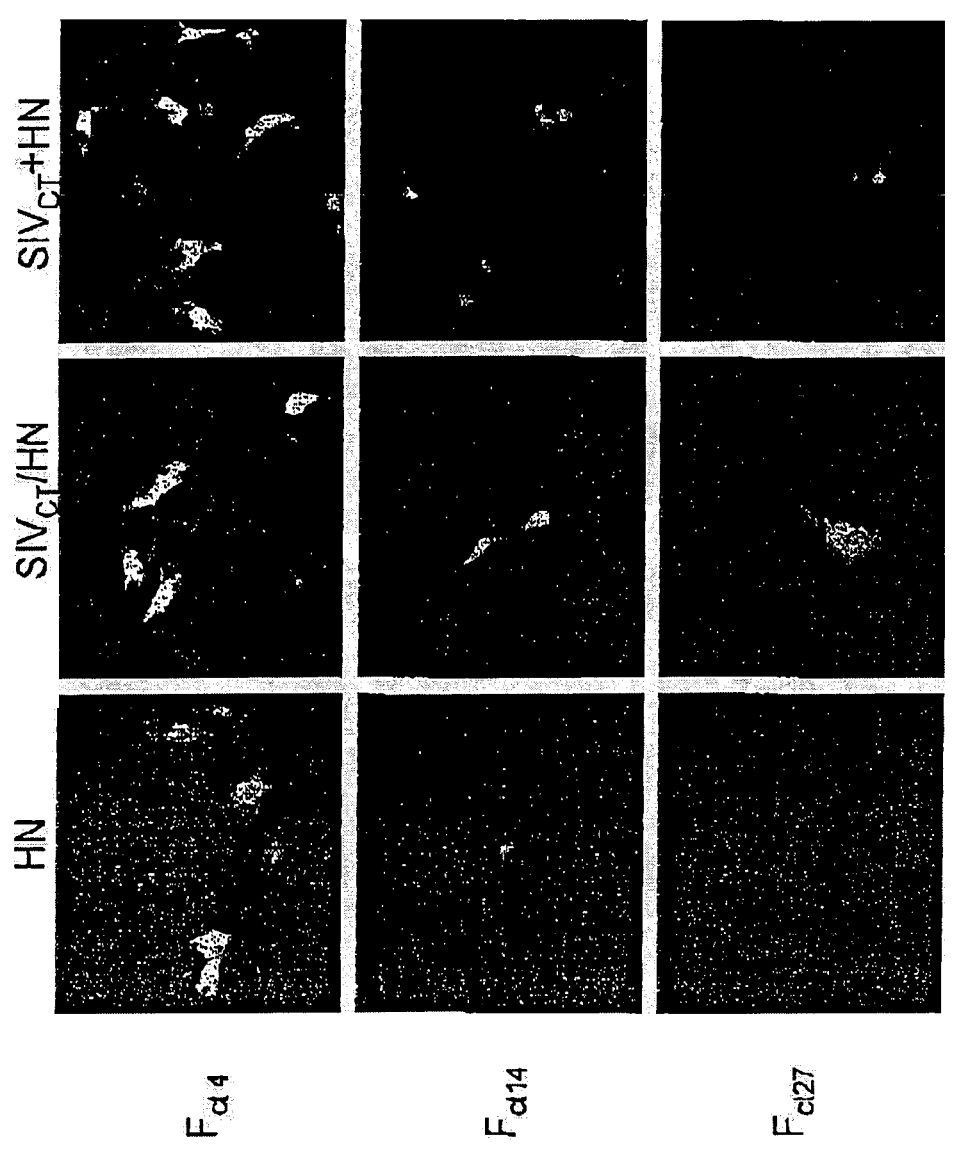
Figure 20:
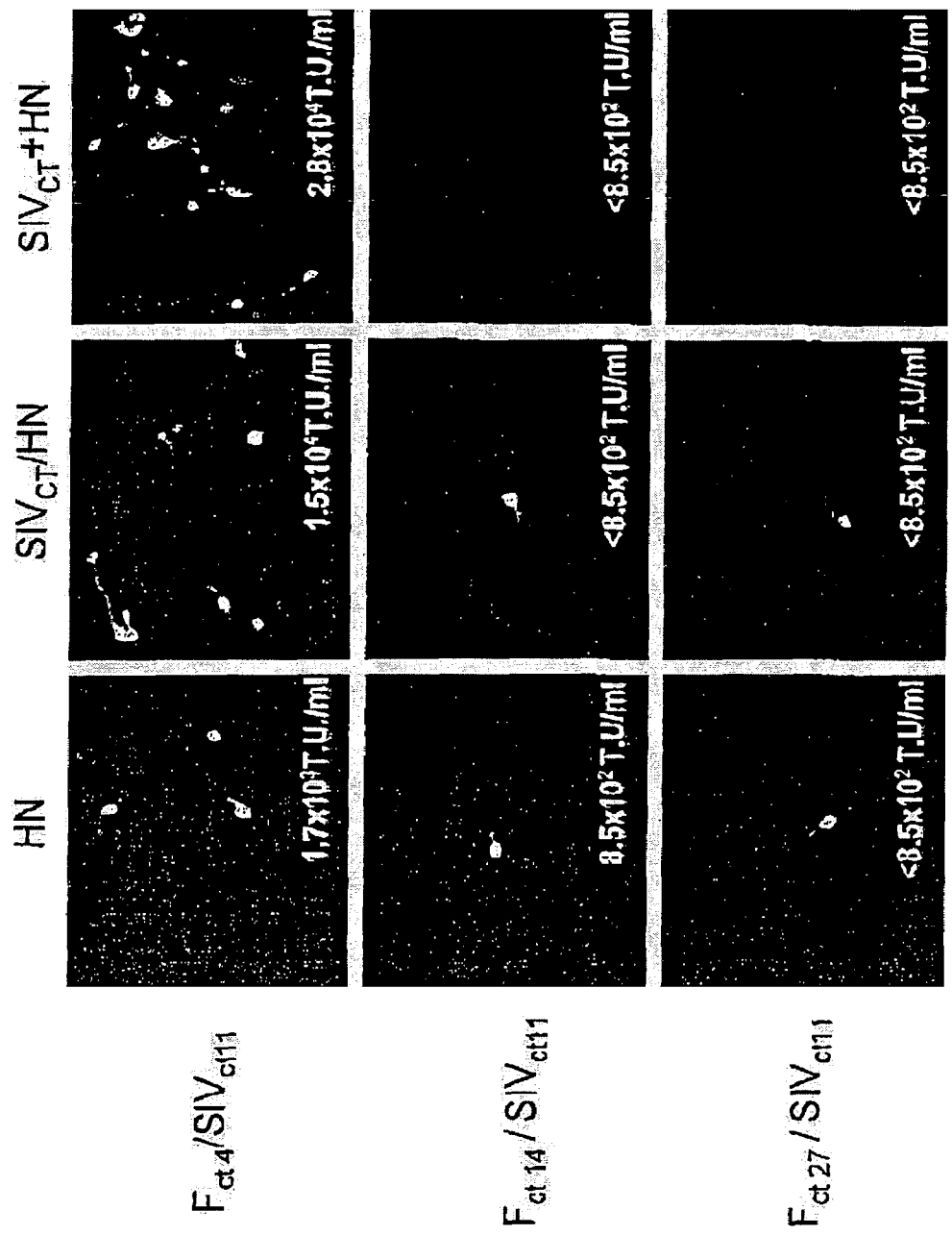
FIG. 20 depicts photographs showing gene transfer into 293T cells via the SeV F/HN pseudotype SIV vector with an addition of $SIV_{c11}$.

The gene transfer vector (pGL3C/CMVL.U3G2/RREc/s/CMVF EGFP/3LTRΔU3), packaging vector (pCAGGS/SIVagm gag-tat/rev), Sendai virus HN protein expression plasmid (pCAGGS-SIVct/HN or pCAGGS-SIVct+HN), and F protein expression plasmid (pCAGGS-Fct4, pCAGGS-Fct14, pCAGGS-Fct27, pCAGGS-Fct4/SIVct11, pCAGGS-Fct14/SIVct11, pCAGGS-Fct27/SIVct11) were co-transfected in various combinations into cells. Then, genes were successfully introduced into 293T cells and BEAS2B cells (FIGS. 18, 19, and 20). Gene transfer was achievable with the modified HN and F protein expression plasmids alone without co-expressing VSV-G. Thus, it was demonstrated that it was possible to provide SIVagm-based pseudotype lentivirus vector modified using Sendai virus F and HN proteins. The titer of the pseudotype vector toward 293T cells was approximately $3.6 \times 10^4$ T.U./ml. The titer was highest when pCAGGS-Fct4 and Fct4/SIVct11 were used in combination as the F protein expression plasmid; among combinations of the two types of F protein expression plasmids with the three types of HN protein expression plasmids, the highest titer was achieved by the combined use of the HN protein expression plasmid pCAGGS-SIVct+HN.

Figure 21:
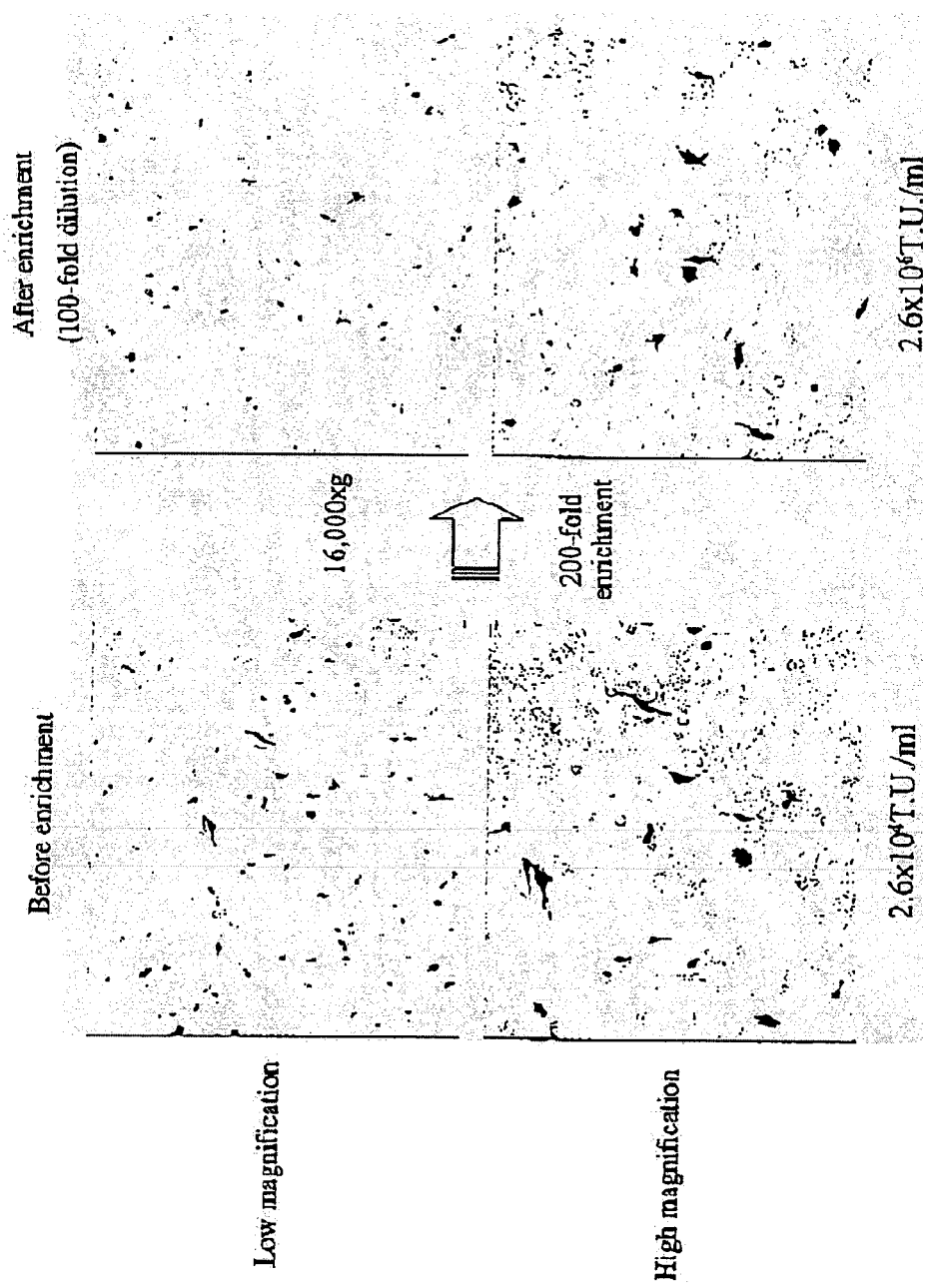
FIG. 21 depicts photographs showing the enriched SeV F/HN pseudotype SIV vector.

It was tested whether the vector that achieved the highest titer, which had been prepared by co-transfecting F protein expression plasmid pCAGGS-Fct4 and HN protein expression plasmid pCAGGS-SIVct+HN, could be enriched by centrifugation. As a result, the F-HN pseudotype vector was confirmed to be enriched to a high level by centrifugation (FIG. 21).

<Tested Oligonucleotides>

The synthetic oligonucleotides used, except SA-F1611 and SA-F1581, were synthesized and purified with reverse-phase cartridges or PAGE in the Biochemical Research Division of the Nippon Flour Mills Co., Ltd. via the Department of Custom DNA Synthesis, Greiner Japan SA-F1611 and SA-F1581 were synthesized in Sawady Technology Co., and used after being purified by HPLC.

```
Xho + Xma:                              (SEQ ID NO: 25)
5'-TCGAGATGTGGTCTGAGTTAAAAATCAGGAGCAACGACGGAGGTGAA
GGACCAGACGCCAACGACCC-3'

Xma-Xho:                                (SEQ ID NO: 26)
5'-CCGGGGGTCGTTGGCGTCTGGTCCTTCACCTCCGTCGTTGCTCCTGA
TTTTTAACTCAGACCACATC-3'

Xma + 131:                              (SEQ ID NO: 27)
5'-CCGGGGAAAGGGGGTGCAACACATCCATATCCAGCCATCTCTACCTG
TTTATGGACAGA-3'

135-Xma:                                (SEQ ID NO: 28)
5'-ACCCTCTGTCCATAAACAGGTAGAGATGGCTGGATATGGATGTGTTG
CACCCCCTTTCC-3'

132 + Bam:                              (SEQ ID NO: 29)
5'-GGGTTAGGTGGTTGCTGATTCTCTCATTCACCCAGTGGG-3'

Bam-136:                                (SEQ ID NO: 30)
5'-GATCCCCACTGGGTGAATGAGAGAATCAGCAACCACCTA-3'

FSIVhn:                                 (SEQ ID NO: 31)
5'-GAGACTCGAGATGTGGTCTGAGTTAAAAATCAGG-3'

RhnSIV:                                 (SEQ ID NO: 32)
5'-AGAGGTAGACCAGTACGAGTCACGTTTGCCCCTATCACCATCCCTAA
CCCTCTGTCCATAAAC-3'

XhFF:                                   (SEQ ID NO: 33)
5'-CCGCTCGAGCATGACAGCATATATCCAGAGA-3'

NotF1650:                               (SEQ ID NO: 34)
5'-ATAGTTTAGCGGCCGCTCATCTGATCTTCGGCTCTAATGT-3'

NotF1611:                               (SEQ ID NO: 35)
5'-ATAGTTTAGCGGCCGCTCAACGGTCATCTGGATTACCCAT-3'

NotF1581:                               (SEQ ID NO: 36)
5'-ATAGTTTAGCGGCCGCTCACCTTCTGAGTCTATAAAGCAC-3'

SA-F1650:                               (SEQ ID NO: 37)
5'-ATAGTTTAGCGGCCGCCTATGGAGATAGAGGAACATATCCCTGCCTA
ACCCTTCTGATCTTCGGCTCTAATGT-3'

SA-F1611:                               (SEQ ID NO: 38)
5'-ATAGTTTAGCGGCCGCCTATGGAGATAGAGGAACATATCCCTGCCTA
ACCCTACGGTCATCTGGATTACCCAT-3'

SA-F1581:                               (SEQ ID NO: 39)
5'-ATAGTTTAGCGGCCGCCTATGGAGATAGAGGAACATATCCCTGCCTA
ACCCTCCTTCTGAGTCTATAAAGCAC-3'
```

EXAMPLE 13

Preparation and Performance Analysis of Sendai Virus Envelope-pseudotyped Retroviral Vector <Cell Culture>

293T cells (human fetal kidney cell line) were cultured in Dulbecco's Modified Eagle Medium (DMEM)-High glucose (Gibco BRL) containing 10% inactivated calf serum (BIO WHITTAKER) under 10% $CO_2$ at 37° C.

<Preparation of Vector>

293T cells were plated in a 6-well plastic culture plate at a cell density of $5 \times 10^5$ cells/well, and then incubated under 10% $CO_2$ at 37° C. for 48 hours. The culture medium was changed with 800 µl/well of DMEM containing 1% bovine serum albumin. The cells were then used in transfection. In the combinations as indicated in Table 7 below, 700 ng of gene transfer vector pMSCV EGFP, 300 ng of ecotropic envelope and gag-pol expression plasmid (IMGENEX), 200 ng of Sendai virus F protein expression plasmid pCAGGS-Fct4, 200 ng each of HN protein expression plasmid pCAGGS-HN, pCAGGS-SIVct/HN, and pCAGGS-SIVct+HN were dissolved in 100 µl of Opti MEM (Gibco BRL) in each well. Then, 6 µl of PLUS Reagent (Gibco BRL) was added to the well. The mixture was stirred, and then allowed to stand still at room temperature for 15 minutes. A solution obtained by diluting 4 µl of LIPOFECTAMINE Reagent (Gibco BRL) with 100 µl of Opti MEM was added to the mixture. The mixed solution was stirred, and then allowed to stand still at room temperature for another 15 minutes. The resulting mixture was added dropwise to the 293 T cells prepared above while being stirred gently. The cells were then incubated under 10% $CO_2$ at 37° C. for 3 hours. 1 ml of DMEM containing 1% bovine serum albumin and 15 µg/ml trypsin (Gibco BRL) was added to each well. After culture under 10% $CO_2$ at 37° C. for 16 to 24 hours, the culture medium in each well was changed with 2 ml of DMEM containing 1% bovine serum albumin and 7.5 µg/ml trypsin (Gibco BRL). After the subsequent culture for 24 hours, the culture supernatant was collected, and filtered with a filter with 0.45-µm diameter pores; the resulting solution was used as a vector solution.

TABLE 7

|  |  | HN protein expression plasmid | | |
|---|---|---|---|---|
|  |  | pCAGGS-HN | pCAGGS-SIVct/HN | pCAGGS-SIVct + HN |
| F protein expression plasmid | pCAGGS-Fct4 | ○ | ○ | ○ |

<SIVagm Vector-mediated Gene Transfer>
293T cells as target cells were plated in 6-well plastic culture plates at a cell density of $1 \times 10^5$ cells/well, and incubated under 10% $CO_2$ at 37° C. for 48 hours. Then, the culture medium was removed from the culture plates, and 1 ml of a mixture obtained by adding polybrene (Sigma) to the vector solution at a final concentration of 8 µg/ml was overlaid on the cells. The plates were incubated under 10% $CO_2$ at 37° C. for 3 hours to transfect the vector to the cells. After three hours, 1 ml of a culture medium containing 20% inactivated calf serum (BIO WHITTAKER) was added to the cells, followed by incubation under 10% $CO_2$ at 37° C. for 48 hours.

<Vector Titration>
The titer was determined based on the number of cells into which genes had been introduced using 1 ml of vector solution. Infection was carried out with 1 ml of the vector solution according to the method described above. 48 hours after infection, the cells were fixed with PBS (Invitrogen) containing 2% formaldehyde and 0.2% glutaraldehyde at room temperature for 20 minutes, and washed once with PBS. The mean value for the number of cells containing the transferred gene in a visual field was determined from three different visual fields under a fluorescence invert microscope (DMIRB (SLR), Leica) with 200-fold magnification, and multiplied by the coefficient 854.865 that had been determined based on the area of the visual field and the area of the plate to determine the titer. The unit of titer was defined as Transducing Unit (T.U.)/ml.

Figure 22:
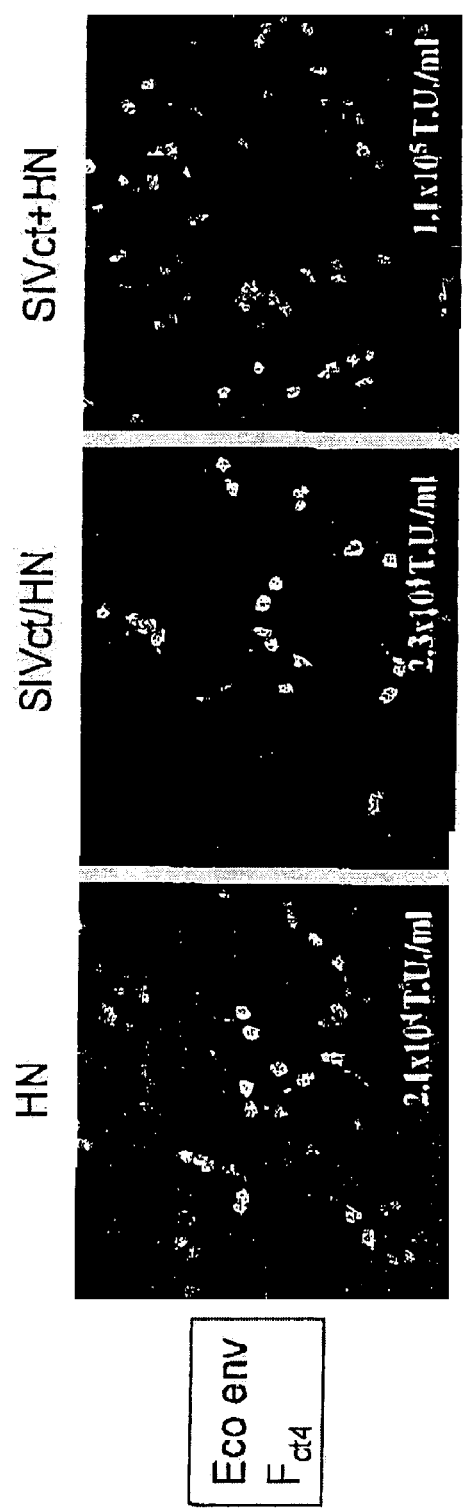
FIG. 22 depicts photographs showing gene transfer via the MSCV-based SeV F/HN pseudotype retroviral vector.

<Results>
The gene transfer vector pMSCV EGFP, ecotropic envelope and gag-pol expression plasmid, Sendai virus F protein expression plasmid pCAGGS-Fct4, HN protein expression plasmid pCAGGS-HN, pCAGGS-SIVct/HN, and pCAGGS-SIVct+HN were co-transfected in combination to cells. Gene transfer into 293T cells was successfully achieved (FIG. 22).

When the modified HN and F protein expression plasmids were used, genes were successfully introduced into human 293T cells, to which ecotropic envelope-containing viruses have no infectivity. Thus, it was demonstrated that it was possible to provide MSCV-based pseudotype retroviral vector modified using Sendai virus F and HN proteins. Further, pCAGGS-Fct4 was used as an F protein expression plasmid in combination with the three types of HN protein expression plasmids; the titer of pseudotype retroviral vector was highest ($1.1 \times 10^5$ T.U./ml), when it was used in combination with the HN protein expression plasmid pCAGGS-SIVct+HN.

EXAMPLE 14

Production of VSV-G/HN Pseudotype Lentivirus Vector and Comparison with VSV-G Pseudotype Lentivirus Vector for the Efficiency of Gene Transfer into Human Bone Marrow Cells Including Hematopoietic Stem Cells <Cell Culture>
293T cells (human fetal kidney cell line) were cultured in Dulbecco's Modified Eagle Medium(DMEM)-High glucose (Gibco BRL) containing 10% inactivated calf serum (BIO WHITTAKER) under 10% $CO_2$ at 37° C.

<Vector Titration>
The titer was determined based on the number of cells into which genes had been introduced using 1 ml of vector solution. Infection was carried out with 1 ml of the vector solution according to the method described above. 48 hours after infection, the cells were fixed with PBS (Invitrogen) containing 2% formaldehyde and 0.2% glutaraldehyde at room temperature for 20 minutes, and washed once with PBS. The mean value for the number of cells containing the transferred gene in a visual field was determined from three different visual fields under a fluorescence invert microscope (DMIRB (SLR), Leica) with 200-fold magnification, and multiplied by the coefficient 854.865 that had been determined based on the area of the visual field and the area of the plate to determine the titer. The unit of titer was defined as Transducing Unit (T.U.)/ml.

<Large-scale Preparation and Enrichment of Vector>
293 T cells were plated in 15-cm plastic dishes at a cell density of $5 \times 10^6$ calls/dish, and incubated under 10% $CO_2$ at 37° C. for 48 hours. The culture medium was changed with 10 ml/dish of DMEM. The cells were used in transfection. 8 µg of gene transfer vector (pGL3C/CMVL.U3G2/RREc/s/CMVF EGFP/3LTRΔU3), 2.4 µg of packaging vector (pCAGGS/SIVagm gag-tat/rev), 1.6 µg each of VSV-G expression plasmid pVSV-G and Sendai virus HN protein expression plasmid pCAGGS-HN, pCAGGS-SIVct/HN, and pCAGGS-SIVct+HN were dissolved in combinations indicated in Table 8 below in 1.5 ml of Opti MEM (Gibco BRL) in each dish. Then, 40 µl of PLUS Reagent (Gibco BRL) was added to the well. The mixture was stirred, and then allowed to stand still at room temperature for 15 minutes. A solution obtained by diluting 60 µl of LIPOFECTAMINE (Gibco BRL) with 1.5 ml of Opti MEM was added to the mixture. The mixed solution was stirred, and then allowed to stand still at room temperature for another 15 minutes. The resulting mixture was added dropwise to the 293 T cells prepared above while being stirred gently. The cells were then incubated under 10% $CO_2$ at 37° C. for 3 hours. 20 ml of DMEM containing 20% inactivated calf serum (BIO WHITTAKER) was added to each well. After culture under 10% $CO_2$ at 37° C. for 16 to 24 hours, the culture medium in each dish was changed with 20 ml of DMEM containing inactivated calf serum (BIO WHITTAKER). After subsequently culturing for 24 hours, culture supernatant was collected. This supernatant was then filtered with a filter having a 0.45-μm diameter. The filtrate was centrifuged at 42,390× g (TOMY SRX-201, TA21BH) at 4° C. for 90 minutes. The pellet was dissolved in a ¹/₁₀₀ volume of reverse transcription reaction solution (TBS, 10 mM $MgCl_2$, 3 mM SPERMINE, 0.3 nM SUPERMIDINE, 100 mM dNTPs). The solution was incubated at 37° C. for two hours. After reverse transcription, the reaction was centrifuged at 42,390× g (TOMY SRX-201, TA21BH) at 4° C. for two hours, and the pellet was dissolved in PBS (containing 5% FCS and 2 μg/ml polybrene). The resulting solution was stored at −80° C. until used.

TABLE 8

|  | pCAGGS-HN | pCAGGS-SIVct/HN | pCAGGS-SIVct + HN |
|---|---|---|---|
| pVSV-G | ○ | ○ | ○ |

<Gene Transfer into Human Bone Marrow CD34⁺ Cells>

Human bone marrow CD34⁺ cells were purchased from BIO WHITTAKER. After thawing, the cells were cultured in Iscove's modified DMEM (IMDM) containing 50 ng/ml IL-6, 100 ng/ml TPO, 100 ng/ml Stem Cell Factor (GIBCO BRL), 100 ng/ml Flt-3 ligand (Research Diagnostics, Flanders, N.J.) (all human recombinants), and 10% FCS under 5% $CO_2$ at 37° C. for 48 hours. After incubation, the medium was removed and the viral vector was added to 2×10⁵ cells using a virus solution of either 2×10⁶ or 10⁷ T.U./ml. Then, 50 ng/ml IL-6, 100 ng/ml TPO, 100 ng/ml Stem Cell Factor (GIBCO BRL), and 100 ng/ml Flt-3 ligand were added to the cells. The cells were harvested 96 hours after the start of incubation.

<Flow Cytometry Analysis>

The harvested cells were stained using a PE-labeled anti-human CD34 antibody (Becton Dickinson), and then analyzed using two types of fluorescence signals corresponding to GFP and PE by flow cytometry (EPICS ELITE, Coulter).

<Results>

When the VSV-G pseudotype vector was used at m.o.i.=10, the proportion of GFP-positive cells in CD34⁺ cells was 9.7%; with the pseudotype vectors VSV-G and HN, SIVct/HN and SIVct+HN, the proportion of GFP-positive cells in CD34⁺ cells was 43.9, 25.2 and 19.7%, respectively (Table 9). On the other hand, using the VSV-G pseudotype vector at m.o.i.=50, the proportion of GFP-positive cells in CD34⁺ cells was 51.4%; with VSV-G and HN, SIVct/HN and SIVct+ HN pseudotype vectors, the proportions of GFP positive cells in CD34⁺ cells were 43.0, 70.8, and 68.4%, respectively (Table 10).

Based on the above findings, it was confirmed that the pseudotype vector prepared by co-expressing VSV-G protein and HN protein ensured increased efficiency of gene transfer into human bone marrow cells including hematopoietic stem cells.

TABLE 9

Population of GFP-positive cell (%) at m.o.i. = 10

|  | VSV-G | VSV-G/HN | VSV-G/ SIVct/HN | VSV-G/ SIVct + HN |
|---|---|---|---|---|
| CD34⁺ | 9.7 | 43.9 | 25.2 | 19.7 |
| CD34⁻ | 16.7 | 8.0 | 0.3 | 0.2 |

TABLE 10

Population of GFP-positive cell (%) at m.o.i. = 50

|  | VSV-G | VSV-G/HN | VSV-G/ SIVct/HN | VSV-G/ SIVct + HN |
|---|---|---|---|---|
| CD34⁺ | 51.4 | 43.0 | 70.8 | 68.4 |
| CD34⁻ | 0.2 | 0.6 | 0.3 | 0.2 |

EXAMPLE 15

Construction of Expression Plasmid for Influenza Virus Envelope Protein

An expression plasmid was constructed, which encodes influenza virus (H1N1)-derived hemagglutinin protein (HA). A fragment was amplified by PCR using primers HAFNot and HARNot and plasmid pDREF HisD (Microbiol. Immunol., 44(8), 677-685, 2000) as a template. The amplified fragment was digested with NotI, and then inserted into the NotI site of the vector prepared by adding an XhoI-NotI site to pCAGGS (Gene, vol.108, pp.193-200, 1991). The plasmid obtained by the procedure described above was used as the HA protein expression plasmid pCAGGS-HA.

The synthetic oligonucleotides used were synthesized and purified with reverse-phase cartridges or PAGE in the Biochemical Research Division of the Nippon Flour Mills Co., Ltd. via the Department of Custom DNA Synthesis, Greiner Japan.

```
HAFNot:                         (SEQ ID NO: 48)
5'-GAGAGCGGCCGCCCAAAATGAAGGCAAAACTACTG-3'

HARNot:                         (SEQ ID NO: 49)
5'-GATGCGGCCGCTCAGATGCATATTCTGCAC-3'
```

EXAMPLE 16

Preparation and Performance Analysis of Influenza Virus Envelope Pseudotype Lentivirus Vector <Cell Culture>

293T cells (human fetal kidney cell line) were cultured in Dulbecco's Modified Eagle Medium(DMEM)-High glucose (Gibco BRL) containing 10% inactivated calf serum (BIO WHITTAKER) under 10% $CO_2$ at 37° C.

<Preparation of Vector>

293T cells were plated in a 6-well plastic culture plate at a cell density of 5×10⁵ cells/well, and then incubated under 10% $CO_2$ at 37° C. for 48 hours. The culture medium was changed with 800 μl/well of DMEM containing 1% bovine serum albumin. The cells were then used in transfection. 1200 ng of gene transfer vector (pGL3C/CMVL.U3G2/RREc/s/ CMVF EGFP/3LTRΔU3), 360 ng of packaging vector (pCAGGS/SIVagm gag-tat/rev), and 240 ng of HA protein expression plasmid pCAGGS-HA were dissolved in 100 μl of Opti MEM (Gibco BRL) in each well. Then, 6 μl of PLUS Reagent (Gibco BRL) was added to the well. The mixture was stirred, and then allowed to stand still at room temperature for 15 minutes. A solution obtained by diluting 4 μl of LIPO-FECTAMINE Reagent (Gibco BRL) with 100 μl or Opti MEM was added to the mixture. The mixed solution was stirred, and then allowed to stand still at room temperature for another 15 minutes. The resulting mixture was added dropwise to the 293 T cells prepared above while being stirred gently. The cells were then incubated under 10% $CO_2$ at 37° C. for 3 hours. 1 ml of DMEM containing 1% bovine serum albumin and 10 μg/ml trypsin (Gibco BRL) was added to each well. After culture under 10% $CO_2$ at 37° C. for 16 to 24 hours, the culture medium in each well was changed with 2 ml of DMEM containing 1% bovine serum albumin, 5 μg/ml trypsin (Gibco BRL), and 50 units of neuraminidase (Roche). After subsequently culturing for 24 hours, culture supernatant was collected. This supernatant was then filtered with a filter having a 0.45-μm diameter and the resulting solution was used as a vector solution.

<SIVagm Vector-mediated Gene Transfer>

293T cells as target cells were plated in 6-well plastic culture plates at a cell density of $1 \times 10^6$ cells/well, and incubated under 10% $CO_2$ at 37° C. for 48 hours. Then, the culture medium was removed from the culture plates, and 1 ml of a mixture obtained by adding polybrene (Sigma) to the vector solution at a final concentration of 8 μg/ml was overlaid on the cells. The plates were incubated under 10% $CO_2$ at 37° C. for 3 hours to transfect the vector to the cells. After three hours, 1 ml of a culture medium containing 20% inactivated calf serum (BIO WHITTAKER) was added to the cells, and the cells were incubated under 10% $CO_2$ at 37° C. for 48 hours.

<Vector Titration>

The titer was determined based on the number of cells into which genes had been introduced using 1 ml of vector solution. Infection was carried out with 1 ml of the vector solution according to the method described above. 48 hours after infection, the cells were fixed with PBS (Invitrogen) containing 2% formaldehyde and 0.2% glutaraldehyde at room temperature for 20 minutes, and washed once with PBS. The mean value for the number of cells containing the transferred gene in a visual field was determined from three different visual fields under a fluorescence invert microscope (DMIRB (SLR) Leica) with 200-fold magnification, and multiplied by the coefficient 854.865 that had been determined based on the area of the visual field and the area of the plate to determine the titer. The unit of titer was defined as Transducing Unit (T.U.)/ml.

<Large-scale Preparation and Enrichment of Vector>

293T cells were plated in 15-cm plastic dishes at a cell density of $5 \times 10^6$ calls/dish, and incubated under 10% $CO_2$ at 37° C. for 48 hours. The culture medium was changed with 10 ml/dish of DMEM containing 1% bovine serum albumin. The cells were used in transfection. 8 μg of gene transfer vector (pGL3C/CMVL.U3G2/RREc/s/CMVF LacZ/3LTRΔU3), 2.4 μg of packaging vector (pCAGGS/SIVagm gag-tat/rev), and 1.6 μg of HA protein expression plasmid pCAGGS-HA were dissolved in 1.5 ml of Opti MEM (Gibco BRL) in each dish. Then, 40 μl of PLUS Reagent (Gibco BRL) was added to the well. The mixture was stirred, and then allowed to stand still at room temperature for 15 minutes. A solution obtained by diluting 60 μl of LIPOFECTAMINE (Gibco BRL) with 1.5 ml of Opti MEM was added to the mixture. The mixed solution was stirred, and then allowed lo stand still at room temperature for another 15 minutes. The resulting mixture was added dropwise to the 293 T cells prepared above while being stirred gently. The cells were then incubated under 10% $CO_2$ at 37° C. for 3 hours. 10 ml of DMEM containing 1% bovine serum albumin and 10 μg/ml trypsin (Gibco BRL) was added to each dish. After culture under 10% $CO_2$ at 37° C. for 16 to 24 hours, the culture medium in each dish was changed with 20 ml of DMEM containing 1% bovine serum albumin, 5 μg/ml trypsin (Gibco BRL), and 500 unit of neuraminidase (Roche). After the subsequent culture for 24 hours, the culture supernatant was collected, and filtered with a filter with 0.45-μm diameter pores. The filtrate was centrifuged at 16,000× g (Beckman J-25I. JA-18) at 4° C. for one hour. The pellet was dissolved in PBS (containing 5% FCS and 2 μg/ml polybrene). The resulting solution was stored at −80° C.

<Results>

Figure 23:
FIG. 23 depicts photographs showing gene transfer via the viral vector pseudotyped by influenza virus envelope.
Figure 24:
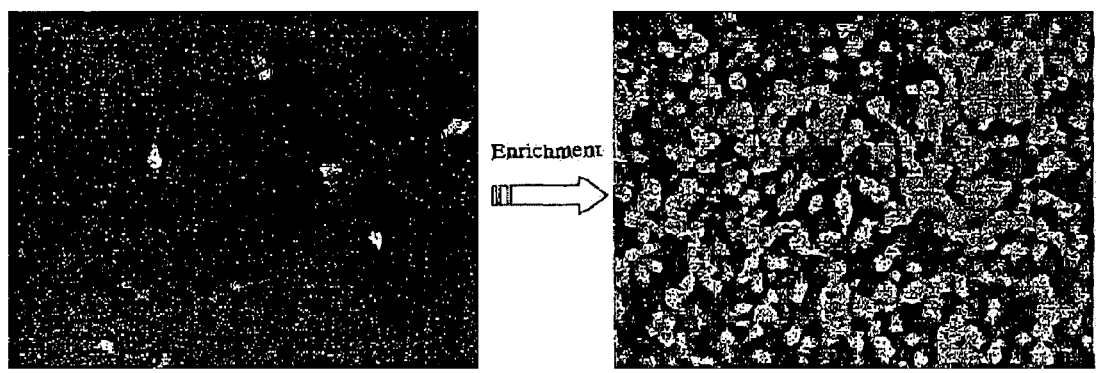
FIG. 24 depicts photographs showing the enriched viral vector pseudotyped by influenza virus envelope.

The gene transfer vector (pGL3C/CMVL.U3G2/RREc/s/CMVF EGFP/3LTRΔU3), packaging vector (pCAGGS/SIVagm gag-tat/rev), and HA protein expression plasmid (pCAGGS-HA) were co-transfected in various combinations into cells. Then, genes were successfully introduced into 293T cells (FIG. 23). Gene transfer was achievable without co-expressing VSV-G. Thus, it was demonstrated that it was possible to provide SIVagm-based pseudotype lentivirus vector using influenza virus HA protein. The titer of the pseudotype vector toward 293T cells was $1.3 \times 10^4$ T.U./ml. Further, it was tested whether the vector prepared by the procedure described above could be enriched by centrifugation. As a result, the HA pseudotype vector was confirmed to be enriched to a high level by centrifugation (FIG. 24).

EXAMPLE 17

Preparation and Performance Analysis of Lentivirus Vector Pseudotyped by Influenza Virus and Sendai Virus Envelope <Cell Culture>

293T cells (human fetal kidney cell line) were cultured in Dulbecco's Modified Eagle Medium(DMEM)-High glucose (Gibco BRL) containing 10% inactivated calf serum (BIO WHITTAKER) under 10% $CO_2$ at 37° C.

<Vector Preparation>

293T cells were plated in a 6-well plastic culture plate at a cell density of $5 \times 10^5$ cells/well, and then incubated under 10% $CO_2$ at 37° C. for 48 hours. The culture medium was changed with 800 μl/well of DMEM containing 1% bovine serum albumin. The cells were then used in transfection. In the combinations as indicated in Table 11 below, 1200 ng of gene transfer vector (pGL3C/CMVL.U3G2/RREc/s/CMVF EGFP/3LTRΔU3), 360 ng of packaging vector (pCAGGS/SIVagm gag-tat/rev), and 240 ng each of Sendai virus HN protein expression plasmid pCAGGS-HN, pCAGGS-SIVct/HN, pCAGGS-SIVct+HN and HA protein expression plasmid were dissolved in 100 μl of Opti MEM (Gibco BRL) in each well. Then, 6 μl of PLUS Reagent (Gibco BRL) was added to the well. The mixture was stirred, and then allowed to stand still at room temperature for 15 minutes. A solution obtained by diluting 4 μl of LIPOFECTAMINE Reagent (Gibco BRL) with 100 μl of Opti MEM was added to the mixture. The mixed solution was stirred, and then allowed to stand still at room temperature for another 15 minutes. The resulting mixture was added dropwise to the 293 T cells prepared above while being stirred gently. The cells were then incubated under 10% $CO_2$ at 37° C. for 3 hours. 1 ml of DMEM containing 1% bovine serum albumin and 10 μg/ml trypsin (Gibco BRL) was added to each well. After culture under 10% $CO_2$ at 37° C. for 16 to 24 hours, the culture medium in each well was changed with 2 ml of DMEM containing 1% bovine serum albumin, 5 μg/ml trypsin (Gibco BRL), and 50 units of neuraminidase (Roche). After the subsequent culture for 24 hours, the culture supernatant was collected, and filtered with a filter with 0.45-μm diameter pores; the resulting solution was used as a vector solution.

TABLE 11

| | HN protein expression plasmid | | |
|---|---|---|---|
| | pCAGGS-HN | pCAGGS-SIVct/HN | pCAGGS-SIVct + HN |
| HA protein expression plasmid  pCAGGS-HA | ○ | ○ | ○ |

<Results>

Figure 25:
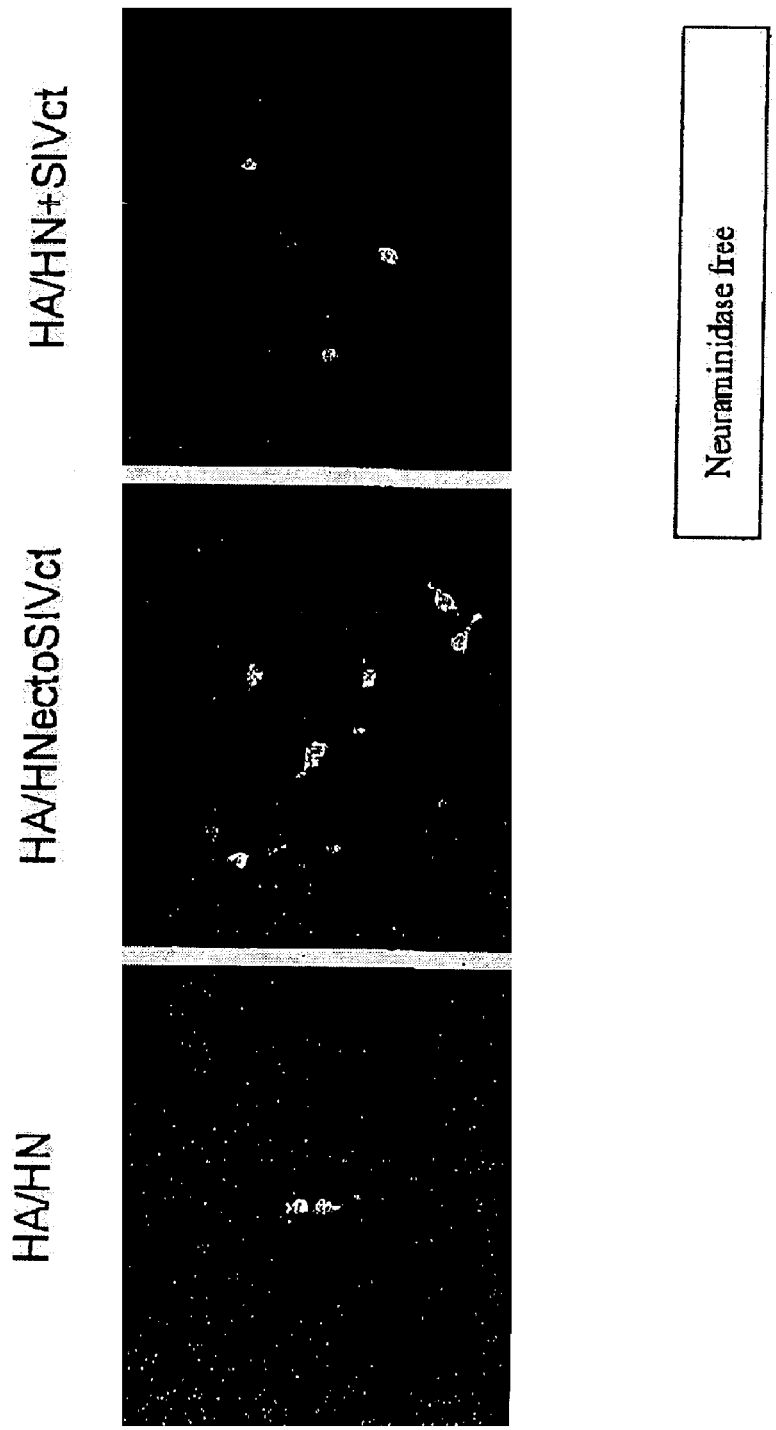
FIG. 25 depicts photographs showing gene transfer via viral vectors pseudotyped by influenza virus envelope and various HN proteins.

The gene transfer vector (pGL3C/CMVL.U3G2/RREc/s/CMVF EGFP/3LTRΔU3), packaging vector (pCAGGS/SIVagm gag-tat/rev), HA protein expression plasmid (pCAGGS-HA), and Sendai virus HN protein expression plasmid (pCAGGS-HN, pCAGGS-SIVct/HN, pCAGGS-SIVct+HN) were co-transfected in various combinations into cells. Then, genes were successfully introduced into 293T cells (FIG. 25). The neuraminidase is responsible for the cleavage of the linkage with sialic acid in the budding of influenza virus, and therefore was required for the preparation of the HA pseudotype. Thus, various HN expression plasmids were tested for the neuraminidase activity of Sendai virus HN protein; coexistence of HN protein led to the production of the desired vector. The result demonstrated that it was possible to provide novel HA/HN pseudotype lentivirus vector. The prepared HA/HN-pseudotyped vector could be enriched by centrifugation (16,000× g),

EXAMPLE 18

Figure 26:
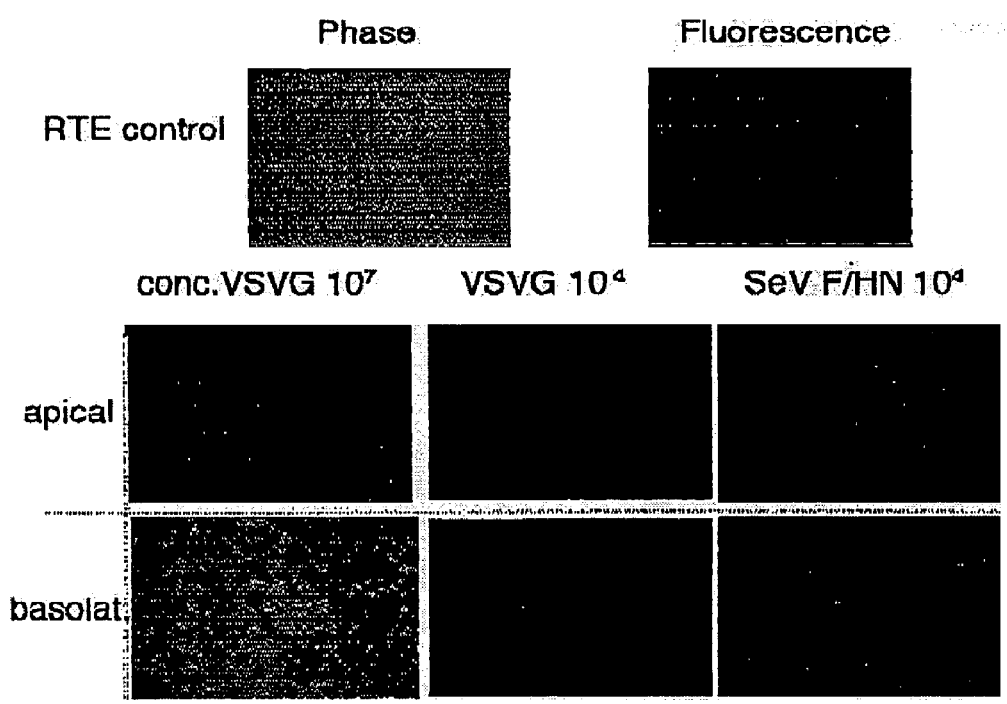
FIG. 26 depicts photographs showing pseudotyped SIV vectors transduced RTE through apical side.

Evaluation of Pseudotyped Vectors using Rat Tracheal Epithelial (RTE) Cells Culture Primary culture of rat tracheal epithelial cells mimics airway tissue. The performance of F/HN-pseudotyped vector (Fct4.SIVct+HN) was tested by preparing primary culture of rat tracheal epithelial cells and by examining the efficiency of gene transfer with the vector into the differentiated cells. This system has been often used to assess the efficiency of gene transfer to tissues of respiratory tract. The apical surface of RTE cells differentiated on particular permeable support has served as a model of air tract surface. A pseudotype vector that had been pseudotyped by using pCAGGS-Fct4 and pCAGGS-SIVct+HN as F protein and HN protein expression plasmids, respectively (see Example 12), was prepared and used. First, RTE cells were isolated and cultured at a cell density of $2 \times 10^5$ cells/ml on permeable support. After culture for 5 to 7 days, the transepithelial resistance was measured, indicating the measured value of 1,500Ω or higher. Thus, it was concluded that the isolated cells were in the differentiated state. An EGFP-expression SIV vector that had been pseudotyped by F/HN was loaded to the culture cells from the apical or basolateral side, and the efficiency of gene transfer was assessed three days after infection The result for gene transfer efficiency of each vector is shown in FIG. 26. When the cultured cells were infected at $10^4$ T.U. with a control vector that had been pseudotyped by VSV-G, no apical infection was detected and the infectivity was also too low in basolateral infection. Even when a viral sample (Conc.) enriched to $10^7$ T.U. by centrifugation was used for infection, no infected cell was detected in the case of apical infection. In contrast, when the vector pseudotyped by SeV F/HN is infected at $10^4$ T.U., high efficient gene transfer was achieved in both apical infection and basolateral infection and the efficiencies were comparable to each other.

In addition, other SIV vectors were constructed by pseudotyping with various combinations of proteins, and the efficiency of gene transfer for each vector was evaluated (Table 12) by infecting them to RTE from the apical side in the same way as described above. In the Table, "titer" refers to the titer at the production; "Conc." refers to enrichment by centrifugation. One EGFP-expression SIV vector (G plus HN in the Table) was pseudotyped by VSV-G/SeV HN proteins, corresponding to (6) in Table 5, and another EGFP-expression SIV vector (G plus F in the Table) was pseudotyped by VSV-G/SeV F proteins, corresponding to (7) in Table 5. Both EGFP-expression SIV vectors could be enriched by centrifugation (24,500×g), and the VSV-G/SeV HN-pseudotyped vector transferred genes into RTE cells with high efficiency. The VSV-G-pseudotyped vector used as a control (which corresponds to (1) in Table 5) did not transfer genes into RTE cells from the apical side. The row F+HN in this Table shows the result obtained with the SIV vector pseudotyped by Fct4 and SIVct+HN prepared as mentioned above.

TABLE 12

Evaluation of pseudotyped SIV with RTE

| Type | Loading env | | titer | Conc. | RTE Transduction |
|---|---|---|---|---|---|
| VSV-G | G | | $10^6$ | yes | − |
| VSV-G | G | HN | $10^6$ | yes | + |
| Co-loading | | F | $10^6$ | yes | Not tested |
| F + HN | Fct4 SIVct + HN | | $10^4$ | Interference | ++ |

INDUSTRIAL APPLICABILITY

The present invention provides retroviral vectors pseudotyped by membrane proteins having hemagglutinin activity. The vectors of the present invention can preferably be used for gene therapy, etc. In particular, the vectors are useful for in vivo administration to the airways and for ex vivo administration to target hematopoietic stem cells,

The invention claimed is:

1. A composition containing a pseudotype retroviral vector, said composition being free from non-retroviral replicative viruses, wherein the pseudotype retroviral vector comprises:
   (a) an HN protein derived from Sendai virus and an amphotropic envelope protein;
   (b) an HN protein derived from Sendai virus and a VSV-G protein; or
   (c) an HN protein and an F protein each derived from Sendai virus, wherein (i) the HN protein comprises an amino acid sequence derived from a cytoplasmic domain of a retroviral envelope protein at the N-terminus and (ii) a portion or the whole of a cytoplasmic domain of the F protein has been deleted.

2. The composition according to claim 1, wherein the pseudotype retroviral vector further comprises a membrane protein having hemagglutinin activity derived from HA protein of orthomyxovirus.

3. The composition according to claim 1, wherein the vector comprises the HN protein and the F protein of (c).

4. The composition according to claim 1, wherein the vector comprises the HN protein and the amphotropic envelope protein of (a).

5. The composition according to claim 1, wherein the vector comprises the HN protein and the VSV-G protein of (b).

6. The composition according to claim 1, wherein the retroviral vector is derived from an oncovirus.

7. The composition according to claim 1, wherein the retroviral vector is derived from a lentivirus.

8. The composition according to claim 7, wherein the lentivirus is derived from a simian immunodeficiency virus.

9. The composition according to claim 1, wherein the vector comprises a foreign gene in an expressible manner.

10. The composition according to claim 9, wherein the vector is used for transferring genes into a cell having mucus.

11. The composition according to claim 10, wherein the cell having mucus is a mucosal epithelial cell.

12. The composition according to claim 11, wherein the mucosal epithelial cell is a mucosal epithelial cell of nasal cavity or pulmonary bronchial tube.

13. The composition according to claim 9, wherein the vector is used for transferring genes into a hemocyte or hematopoietic cell.

14. The composition according to claim 13, wherein the hemocyte or hematopoietic cell is a hematopoietic stem cell.

15. A method for introducing a foreign gene into cells, the method comprising the step of contacting cells with the composition according to claim 9, wherein (i) the step of contacting is performed in vitro, or (ii) the cells are mucosal epithelial cells of nasal cavity or pulmonary bronchial tube and the contact is performed by intranasal administration.

16. A packaging cell for producing the composition according to claim 1, the cell comprising, in an expressible manner, DNAs encoding (i) a gag protein and a pol protein of a retrovirus and (ii) the proteins of any one of (a) to (c) recited in claim 1.

17. A method for producing the composition according to claim 1, the method comprising the step of (i) transcribing a retrovirus-derived gene transfer vector DNA in a packaging cell which comprises, in an expressible manner, DNAs encoding the proteins of any one of (a) to (c) recited in claim 1, and (ii) recovering a culture medium of the packaging cell.

18. The composition according to claim 3, wherein the HN protein comprises the sequence of SEQ ID NO: 40 or 41.

19. The composition according to claim 3, wherein the F protein ends at the end of SEQ ID NO: 42, 43, or 44.

20. The composition according to claim 3, wherein the F protein has a cytoplasmic domain of a retroviral envelope protein.

21. The composition according to claim 20, wherein (i) the retroviral envelope protein is an envelope protein of a simian immunodeficiency virus, and (ii) the cytoplasmic domain of the envelope protein of the simian immunodeficiency virus is connected to the F protein so as to have the sequence of SEQ ID NO: 45, 46, or 47.

22. The method according to claim 15, wherein the cells are mucosal epithelial cells of nasal cavity or pulmonary bronchial tube, and the step of contacting is performed by intranasal administration.

23. The method according to claim 15, wherein the cells are hemocytes or hematopoietic cells, and the step of contacting is performed in vitro.

24. The method according to claim 23, wherein the cells are isolated hematopoietic stem cells, and the step of contacting is performed in vitro.

25. The composition according to claim 3, wherein a portion or the whole of a cytoplasmic domain of the F protein has been deleted leaving 0 to 4 amino acid residues of the cytoplasrnic domain.

26. The composition according to claim 25, wherein a portion or the whole of a cytoplasmic domain of the F protein has been deleted leaving 4 amino acid residues of the cytoplasmic domain.

27. The packaging cell according to claim 16, wherein the cell further comprises in an expressible manner a DNA encoding a membrane protein having hemagglutinin activity derived from HA protein of orthomyxovirus.

28. The packaging cell according to claim 16, wherein the proteins of (ii) are the proteins of (c) recited in claim 1.

29. The packaging cell according to claim 28, wherein a portion or the whole of a cytoplasmic domain of the F protein has been deleted leaving 0 to 4 amino acid residues of the cytoplasmic domain.

30. The packaging cell according to claim 28, wherein the HN protein comprises the sequence of SEQ ID NO: 40 or 41.

31. The packaging cell according to claim 29, wherein the F protein ends at the end of SEQ ID NO: 42, 43, or 44.

32. The packaging cell according to claim 29, wherein the F protein has a cytoplasmic domain of a retroviral envelope protein.

33. The packaging cell according to claim 32, wherein (i) the retroviral envelope protein is an envelope protein of a simian immunodeficiency virus, and (ii) the cytoplasmic domain of the envelope protein of the simian immunodeficiency virus is connected to the F protein so as to have the sequence of SEQ ID NO: 45, 46, or 47.

34. The method according to claim 17, wherein the cell further comprises in an expressible manner a DNA encoding a membrane protein having hemagglutinin activity derived from HA protein of orthomyxovirus.

35. The method according to claim 17, wherein the proteins of any one of (a) to (c) are the proteins of (c) recited in claim 1.

36. The method according to claim 35, wherein a portion or the whole of a cytoplasmic domain of the F protein has been deleted leaving 0 to 4 amino acid residues of the cytoplasmic domain.

37. The method according to claim 35, wherein the sequence of SEQ ID NO: 40 or 41.

38. The method according to claim 35, wherein the F protein ends at the end of SEQ ID NO: 42, 43, or 44.

39. The method according to claim 35, wherein the F protein has a cytoplasmic domain of a retroviral envelope protein.

40. The method according to claim 39, wherein (i) the retroviral envelope protein is an envelope protein of a simian immunodeficiency virus, and (ii) the cytoplasmic domain of the envelope protein of the simian immunodeficiency virus is connected to the F protein so as to have the sequence of SEQ ID NO: 45, 46, or 47.

41. A composition containing a pseudotype retroviral vector, wherein the pseudotype retroviral vector comprises a Sendai virus HN protein modified to comprise the amino acid sequence of amino acids 1-45 of SEQ ID NO: 40 or 41 at the N-terminus, and a Sendai virus F protein modified to delete a portion or the whole of a cytoplasmic domain of the F protein.

42. The composition according to claim 41, wherein the Sendai virus HN protein comprises the amino acid sequence of SEQ ID NO: 40 or 41.

43. The composition according to claim 41, wherein the retroviral vector is derived from a lentivirus.

44. The composition according to claim 3, wherein the retroviral vector is derived from a lentivirus.

45. The composition according to claim 4, wherein the retroviral vector is derived from a lentivirus.

46. The composition according to claim 5, wherein the retroviral vector is derived from a lentivirus.

47. The composition according to claim 43, wherein the lentivirus is a simian immunodeficiency virus.

48. The composition according to claim 44, wherein the lentivirus is a simian immunodeficiency virus.

49. The composition according to claim 45, wherein the lentivirus is a simian immunodeficiency virus.

50. The composition according to claim 46, wherein the lentivirus is a simian immunodeficiency virus.

51. The composition according to claim 47, wherein the simian immunodeficiency virus is a SIVagm.

52. The composition according to claim 48, wherein the simian immunodeficiency virus is a SIVagm.

53. The composition according to claim 49, wherein the simian immunodeficiency virus is a SIVagm.

54. The composition according to claim 50, wherein the simian immunodeficiency virus is a SIVagm.

* * * * *

UNITED STATES PATENT AND TRADEMARK OFFICE
CERTIFICATE OF CORRECTION

PATENT NO. : 7,510,706 B2
APPLICATION NO. : 10/306949
DATED : March 31, 2009
INVENTOR(S) : Yoshikazu Yonemitsu et al.

It is certified that error appears in the above-identified patent and that said Letters Patent is hereby corrected as shown below:

Column 70, lines 56-57, Claim 25, replace "cytoplasrnic" with --cytoplasmic--; and Column 71, lines 29-30, Claim 37, replace "wherein the sequence" with --wherein the HN protein comprises the sequence--.

Signed and Sealed this

Twenty-third Day of June, 2009

JOHN DOLL
*Acting Director of the United States Patent and Trademark Office*

SEQUENCE LISTING

<160> NUMBER OF SEQ ID NOS: 49

<210> SEQ ID NO 1
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 1
gcagatctca accaggaggc gaggctgcat tttggg                    36

<210> SEQ ID NO 2
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 2
gcgaattcta cttactggtg ctgtaaagga gccaaa                    36

<210> SEQ ID NO 3
<211> LENGTH: 40
<212> TYPE: DNA
<213> ORGANISM: Artificial Sequence
<220> FEATURE:
<223> OTHER INFORMATION: artificially synthesized sequence

<400> SEQUENCE: 3
atcggaattc ttttattgta agatggattg gttttaaat                 40

<210> SEQ ID NO 4
<211> LENGTH: 48
<212> TYPE: DNA
<213> ORGANISM: Artificial Sequence
<220> FEATURE:
<223> OTHER INFORMATION: artificially synthesized sequence

<400> SEQUENCE: 4
cgggatccgc ggccgcggat atggatctgt ggagatagag gaacatat       48

<210> SEQ ID NO 5
<211> LENGTH: 29
<212> TYPE: DNA
<213> ORGANISM: Artificial Sequence
<220> FEATURE:
<223> OTHER INFORMATION: artificially synthesized sequence

<400> SEQUENCE: 5
tcgagactag tgacttggtg agtaggctt                            29

<210> SEQ ID NO 6
<211> LENGTH: 29
<212> TYPE: DNA
<213> ORGANISM: Artificial Sequence
<220> FEATURE:
<223> OTHER INFORMATION: artificially synthesized sequence

<400> SEQUENCE: 6
tcgaaagcct actcaccaag tcactactc                            29

<210> SEQ ID NO 7
<211> LENGTH: 19
<212> TYPE: DNA
<213> ORGANISM: Artificial Sequence
<220> FEATURE:
<223> OTHER INFORMATION: artificially synthesized sequence

<400> SEQUENCE: 7
aatttctcga gcggccgca                                       19

<210> SEQ ID NO 8

<211> LENGTH: 19
<212> TYPE: DNA
<213> ORGANISM: Artificial Sequence
<220> FEATURE:
<223> OTHER INFORMATION: artificially synthesized sequence

<400> SEQUENCE: 8
aatttgcggc cgctcgaga                                           19

<210> SEQ ID NO 9
<211> LENGTH: 35
<212> TYPE: DNA
<213> ORGANISM: Artificial Sequence
<220> FEATURE:
<223> OTHER INFORMATION: artificially synthesized sequence

<400> SEQUENCE: 9
gcggtacctg gatgggattt attactccga tagga                         35

<210> SEQ ID NO 10
<211> LENGTH: 40
<212> TYPE: DNA
<213> ORGANISM: Artificial Sequence
<220> FEATURE:
<223> OTHER INFORMATION: artificially synthesized sequence

<400> SEQUENCE: 10
gcgaattcga tagggcttga aacatgggta ctatttctgc                    40

<210> SEQ ID NO 11
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 11
gcgaattccc gtttgtgcta gggttcttag gcttct                        36

<210> SEQ ID NO 12
<211> LENGTH: 40
<212> TYPE: DNA
<213> ORGANISM: Artificial Sequence
<220> FEATURE:
<223> OTHER INFORMATION: artificially synthesized sequence

<400> SEQUENCE: 12
tccccgcgga tatggatctg tggagataga ggaacatatc                    40

<210> SEQ ID NO 13
<211> LENGTH: 44
<212> TYPE: DNA
<213> ORGANISM: Artificial Sequence
<220> FEATURE:
<223> OTHER INFORMATION: artificially synthesized sequence

<400> SEQUENCE: 13
gcgcggccgc ggatccgtcg acgcactttt taaaagaaaa ggga               44

<210> SEQ ID NO 14
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 14

```
gcgagctcta atgcaggcaa gtttattagc tttcta                                    36

<210> SEQ ID NO 15
<211> LENGTH: 40
<212> TYPE: DNA
<213> ORGANISM: Artificial Sequence
<220> FEATURE:
<223> OTHER INFORMATION: artificially synthesized sequence

<400> SEQUENCE: 15
ggaattcccg cggtagttat taatagtaat caattacggg                                40

<210> SEQ ID NO 16
<211> LENGTH: 40
<212> TYPE: DNA
<213> ORGANISM: Artificial Sequence
<220> FEATURE:
<223> OTHER INFORMATION: artificially synthesized sequence

<400> SEQUENCE: 16
cgggatccgc ggccgcttac ttgtacagct cgtccatgcc                                40

<210> SEQ ID NO 17
<211> LENGTH: 40
<212> TYPE: DNA
<213> ORGANISM: Artificial Sequence
<220> FEATURE:
<223> OTHER INFORMATION: artificially synthesized sequence

<400> SEQUENCE: 17
tatataagca gagctcgctg gcttgtaact cagtctctta                                40

<210> SEQ ID NO 18
<211> LENGTH: 40
<212> TYPE: DNA
<213> ORGANISM: Artificial Sequence
<220> FEATURE:
<223> OTHER INFORMATION: artificially synthesized sequence

<400> SEQUENCE: 18
tatataagtg cagtacgctg gcttgtaact cagtctctta                                40

<210> SEQ ID NO 19
<211> LENGTH: 40
<212> TYPE: DNA
<213> ORGANISM: Artificial Sequence
<220> FEATURE:
<223> OTHER INFORMATION: artificially synthesized sequence

<400> SEQUENCE: 19
tataaaaagc gaagccgctg gcttgtaact cagtctctta                                40

<210> SEQ ID NO 20
<211> LENGTH: 40
<212> TYPE: DNA
<213> ORGANISM: Artificial Sequence
<220> FEATURE:
<223> OTHER INFORMATION: artificially synthesized sequence

<400> SEQUENCE: 20
gcgaattcga tagggcttga aacatgggta ctatttctgc                                40

<210> SEQ ID NO 21
<211> LENGTH: 40
<212> TYPE: DNA
```

<213> ORGANISM: Artificial Sequence
<220> FEATURE:
<223> OTHER INFORMATION: artificially synthesized sequence

<400> SEQUENCE: 21
cggggtacct caatattggc cattagccat attattcatt                    40

<210> SEQ ID NO 22
<211> LENGTH: 40
<212> TYPE: DNA
<213> ORGANISM: Artificial Sequence
<220> FEATURE:
<223> OTHER INFORMATION: artificially synthesized sequence

<400> SEQUENCE: 22
agttacaagc cagcgagctc tgcttatata gacctcccac                    40

<210> SEQ ID NO 23
<211> LENGTH: 99
<212> TYPE: DNA
<213> ORGANISM: Artificial Sequence
<220> FEATURE:
<223> OTHER INFORMATION: artificially synthesized sequence

<400> SEQUENCE: 23
atgcgagctc gtcgacgcac tttttaaaag aaaagggagg actggatggg atttattact    60
ccgataggac gctggcttgt aactcagtct cttactagg                    99

<210> SEQ ID NO 24
<211> LENGTH: 36
<212> TYPE: DNA
<213> ORGANISM: Artificial Sequence
<220> FEATURE:
<223> OTHER INFORMATION: artificially synthesized sequence

<400> SEQUENCE: 24
gcgagctcta atgcaggcaa gtttattagc tttcta                       36

<210> SEQ ID NO 25
<211> LENGTH: 67
<212> TYPE: DNA
<213> ORGANISM: Artificial Sequence
<220> FEATURE:
<223> OTHER INFORMATION: artificially synthesized sequence

<400> SEQUENCE: 25
tcgagatgtg gtctgagtta aaaatcagga gcaacgacgg aggtgaagga ccagacgcca    60
acgaccc                                                        67

<210> SEQ ID NO 26
<211> LENGTH: 67
<212> TYPE: DNA
<213> ORGANISM: Artificial Sequence
<220> FEATURE:
<223> OTHER INFORMATION: artificially synthesized sequence

<400> SEQUENCE: 26 ccggggggtcg ttggcgtctg gtccttcacc tccgtcgttg ctcctgattt taactcaga    60 ccacatc                                                        67

<210> SEQ ID NO 27
<211> LENGTH: 59
<212> TYPE: DNA
<213> ORGANISM: Artificial Sequence

```
<220> FEATURE:
<223> OTHER INFORMATION: artificially synthesized sequence

<400> SEQUENCE: 27
ccggggaaag ggggtgcaac acatccatat ccagccatct ctacctgttt atggacaga      59

<210> SEQ ID NO 28
<211> LENGTH: 59
<212> TYPE: DNA
<213> ORGANISM: Artificial Sequence
<220> FEATURE:
<223> OTHER INFORMATION: artificially synthesized sequence

<400> SEQUENCE: 28
accctctgtc cataaacagg tagagatggc tggatatgga tgtgttgcac cccctttcc      59

<210> SEQ ID NO 29
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 29
gggttaggtg gttgctgatt ctctcattca cccagtggg                           39

<210> SEQ ID NO 30
<211> LENGTH: 39
<212> TYPE: DNA
<213> ORGANISM: Artificial Sequence
<220> FEATURE:
<223> OTHER INFORMATION: artificially synthesized sequence

<400> SEQUENCE: 30
gatccccact gggtgaatga gagaatcagc aaccaccta                           39

<210> SEQ ID NO 31
<211> LENGTH: 34
<212> TYPE: DNA
<213> ORGANISM: Artificial Sequence
<220> FEATURE:
<223> OTHER INFORMATION: artificially synthesized sequence

<400> SEQUENCE: 31
gagactcgag atgtggtctg agttaaaaat cagg                                34

<210> SEQ ID NO 32
<211> LENGTH: 63
<212> TYPE: DNA
<213> ORGANISM: Artificial Sequence
<220> FEATURE:
<223> OTHER INFORMATION: artificially synthesized sequence

<400> SEQUENCE: 32
agaggtagac cagtacgagt cacgtttgcc cctatcacca tccctaaccc tctgtccata     60
aac                                                                  63

<210> SEQ ID NO 33
<211> LENGTH: 31
<212> TYPE: DNA
<213> ORGANISM: Artificial Sequence
<220> FEATURE:
<223> OTHER INFORMATION: artificially synthesized sequence

<400> SEQUENCE: 33
```
ccgctcgagc atgacagcat atatccagag a    31

<210> SEQ ID NO 34
<211> LENGTH: 40
<212> TYPE: DNA
<213> ORGANISM: Artificial Sequence
<220> FEATURE:
<223> OTHER INFORMATION: artificially synthesized sequence

<400> SEQUENCE: 34
atagtttagc ggccgctcat ctgatcttcg gctctaatgt    40

<210> SEQ ID NO 35
<211> LENGTH: 40
<212> TYPE: DNA
<213> ORGANISM: Artificial Sequence
<220> FEATURE:
<223> OTHER INFORMATION: artificially synthesized sequence

<400> SEQUENCE: 35
atagtttagc ggccgctcaa cggtcatctg gattacccat    40

<210> SEQ ID NO 36
<211> LENGTH: 40
<212> TYPE: DNA
<213> ORGANISM: Artificial Sequence
<220> FEATURE:
<223> OTHER INFORMATION: artificially synthesized sequence

<400> SEQUENCE: 36
atagtttagc ggccgctcac cttctgagtc tataaagcac    40

<210> SEQ ID NO 37
<211> LENGTH: 73
<212> TYPE: DNA
<213> ORGANISM: Artificial Sequence
<220> FEATURE:
<223> OTHER INFORMATION: artificially synthesized sequence

<400> SEQUENCE: 37
atagtttagc ggccgcctat ggagatagag gaacatatcc ctgcctaacc cttctgatct    60
tcggctctaa tgt    73

<210> SEQ ID NO 38
<211> LENGTH: 73
<212> TYPE: DNA
<213> ORGANISM: Artificial Sequence
<220> FEATURE:
<223> OTHER INFORMATION: artificially synthesized sequence

<400> SEQUENCE: 38
atagtttagc ggccgcctat ggagatagag gaacatatcc ctgcctaacc ctacggtcat    60
ctggattacc cat    73

<210> SEQ ID NO 39
<211> LENGTH: 73
<212> TYPE: DNA
<213> ORGANISM: Artificial Sequence
<220> FEATURE:
<223> OTHER INFORMATION: artificially synthesized sequence

<400> SEQUENCE: 39
atagtttagc ggccgcctat ggagatagag gaacatatcc ctgcctaacc ctccttctga    60
gtctataaag cac    73

```
<210> SEQ ID NO 40
<211> LENGTH: 54
<212> TYPE: PRT
<213> ORGANISM: Artificial Sequence
<220> FEATURE:
<223> OTHER INFORMATION: artificially synthesized sequence

<400> SEQUENCE: 40

Trp Ser Glu Leu Lys Ile Arg Ser Asn Asp Gly Gly Glu Gly Pro Glu
 1               5                  10                  15

Asp Ala Asn Asp Pro Arg Gly Lys Gly Val Gln His Ile His Ile Gln
            20                  25                  30

Pro Ser Leu Pro Val Tyr Gly Gln Arg Val Arg Val Arg Trp Leu Leu
        35                  40                  45

Ile Leu Ser Phe Thr Gln
        50

<210> SEQ ID NO 41
<211> LENGTH: 54
<212> TYPE: PRT
<213> ORGANISM: Artificial Sequence
<220> FEATURE:
<223> OTHER INFORMATION: artificially synthesized sequence

<400> SEQUENCE: 41

Trp Ser Glu Leu Lys Ile Arg Ser Asn Asp Gly Gly Glu Gly Pro Glu
 1               5                  10                  15

Asp Ala Asn Asp Pro Arg Gly Lys Gly Val Gln His Ile His Ile Gln
            20                  25                  30

Pro Ser Leu Pro Val Tyr Gly Gln Arg Val Arg Val Arg Asp Gly Asp
        35                  40                  45

Arg Gly Lys Arg Asp Ser
        50

<210> SEQ ID NO 42
<211> LENGTH: 15
<212> TYPE: PRT
<213> ORGANISM: Artificial Sequence
<220> FEATURE:
<223> OTHER INFORMATION: artificially synthesized sequence

<400> SEQUENCE: 42

Val Val Ile Ile Val Ile Ile Ile Val Leu Tyr Arg Leu Arg Arg
 1               5                  10                  15

<210> SEQ ID NO 43
<211> LENGTH: 25
<212> TYPE: PRT
<213> ORGANISM: Artificial Sequence
<220> FEATURE:
<223> OTHER INFORMATION: artificially synthesized sequence

<400> SEQUENCE: 43

Val Val Ile Ile Val Ile Ile Ile Val Leu Tyr Arg Leu Arg Arg Ser
 1               5                  10                  15

Met Leu Met Gly Asn Pro Asp Asp Arg
            20                  25

<210> SEQ ID NO 44
<211> LENGTH: 38
<212> TYPE: PRT
<213> ORGANISM: Artificial Sequence
```

<220> FEATURE:
<223> OTHER INFORMATION: artificially synthesized sequence

<400> SEQUENCE: 44

Val Val Ile Ile Val Ile Ile Ile Val Leu Tyr Arg Leu Arg Arg Ser
1               5                   10                  15

Met Leu Met Gly Asn Pro Asp Asp Arg Ile Pro Arg Asp Thr Tyr Thr
            20                  25                  30

Leu Glu Pro Lys Ile Arg
        35

<210> SEQ ID NO 45
<211> LENGTH: 26
<212> TYPE: PRT
<213> ORGANISM: Artificial Sequence
<220> FEATURE:
<223> OTHER INFORMATION: artificially synthesized sequence

<400> SEQUENCE: 45

Val Val Ile Ile Val Ile Ile Ile Val Leu Tyr Arg Leu Arg Arg Arg
1               5                   10                  15

Val Arg Gln Gly Tyr Val Pro Leu Ser Pro
            20                  25

<210> SEQ ID NO 46
<211> LENGTH: 36
<212> TYPE: PRT
<213> ORGANISM: Artificial Sequence
<220> FEATURE:
<223> OTHER INFORMATION: artificially synthesized sequence

<400> SEQUENCE: 46

Val Val Ile Ile Val Ile Ile Ile Val Leu Tyr Arg Leu Arg Arg Ser
1               5                   10                  15

Met Leu Met Gly Asn Pro Asp Asp Arg Arg Val Arg Gln Gly Tyr Val
            20                  25                  30

Pro Leu Ser Pro
        35

<210> SEQ ID NO 47
<211> LENGTH: 49
<212> TYPE: PRT
<213> ORGANISM: Artificial Sequence
<220> FEATURE:
<223> OTHER INFORMATION: artificially synthesized sequence

<400> SEQUENCE: 47

Val Val Ile Ile Val Ile Ile Ile Val Leu Tyr Arg Leu Arg Arg Ser
1               5                   10                  15

Met Leu Met Gly Asn Pro Asp Asp Arg Ile Pro Arg Asp Thr Tyr Thr
            20                  25                  30

Leu Glu Pro Lys Ile Arg Arg Val Arg Gln Gly Tyr Val Pro Leu Ser
        35                  40                  45

Pro

<210> SEQ ID NO 48
<211> LENGTH: 35
<212> TYPE: DNA
<213> ORGANISM: Artificial Sequence
<220> FEATURE:
<223> OTHER INFORMATION: artificially synthesized sequence

<400> SEQUENCE: 48

```
gagagcggcc gcccaaaatg aaggcaaaac tactg                          35

<210> SEQ ID NO 49
<211> LENGTH: 30
<212> TYPE: DNA
<213> ORGANISM: Artificial Sequence
<220> FEATURE:
<223> OTHER INFORMATION: artificially synthesized sequence

<400> SEQUENCE: 49
gatgcggccg ctcagatgca tattctgcac                                30
```